(12) United States Patent
Gadde et al.

(10) Patent No.: US 12,033,738 B2
(45) Date of Patent: Jul. 9, 2024

(54) NEGATIVE PRESSURE WOUND THERAPY SYSTEM USING EULERIAN VIDEO MAGNIFICATION

(71) Applicant: Smith & Nephew PLC, Watford (GB)

(72) Inventors: Yeswanth Gadde, Pocklington (GB); Allan Kenneth Frazer Grugeon Hunt, Beverley (GB); Marcus Damian Phillips, Wakefield (GB)

(73) Assignee: Smith & Nephew PLC, Watford (GB)

( * ) Notice: Subject to any disclaimer, the term of this patent is extended or adjusted under 35 U.S.C. 154(b) by 268 days.

(21) Appl. No.: 16/613,768

(22) PCT Filed: May 11, 2018

(86) PCT No.: PCT/EP2018/062207
§ 371 (c)(1),
(2) Date: Nov. 14, 2019

(87) PCT Pub. No.: WO2018/210693
PCT Pub. Date: Nov. 22, 2018

(65) Prior Publication Data
US 2020/0078499 A1    Mar. 12, 2020

Related U.S. Application Data

(60) Provisional application No. 62/506,524, filed on May 15, 2017.

(51) Int. Cl.
*A61M 1/00*      (2006.01)
*A61F 13/00*      (2024.01)
(Continued)

(52) U.S. Cl.
CPC .............. *G16H 20/30* (2018.01); *A61F 13/05* (2024.01); *A61M 1/73* (2021.05); *A61M 1/74* (2021.05);
(Continued)

(58) Field of Classification Search
CPC .. A61M 1/90; A61M 1/74; A61M 2205/3306; A61M 2205/3313;
(Continued)

(56) References Cited

U.S. PATENT DOCUMENTS

| 3,896,802 A | 7/1975 | Williams |
| 4,334,530 A | 6/1982 | Hassell |

(Continued)

FOREIGN PATENT DOCUMENTS

| CA | 3059516 A1 | 10/2018 |
| CN | 204133473 U | 2/2015 |

(Continued)

OTHER PUBLICATIONS

Dargaville, Tim R., et al. "Sensors and imaging for wound healing: a review." Biosensors and Bioelectronics 41 (2013): 30-42. (Year: 2013).*

(Continued)

*Primary Examiner* — Adam Marcetich
*Assistant Examiner* — Rachel O'Connell
(74) *Attorney, Agent, or Firm* — Knobbe, Martens, Olson & Bear, LLP

(57) ABSTRACT

Embodiments of tissue monitoring in combination with negative pressure wound therapy systems and methods are disclosed. In some embodiments, a monitoring and therapy system comprises collecting video images of a tissue site and amplifying said video images via Eulerian Video Magnification. Depending upon the changes detected via Eulerian Video magnification, negative pressure wound therapy may be delivered to the tissue site, stopped, or altered in some manner.

9 Claims, 18 Drawing Sheets

(51) Int. Cl.
*A61F 13/05* (2024.01)
*G16H 20/30* (2018.01)
*G16H 20/40* (2018.01)
*G16H 30/40* (2018.01)

(52) U.S. Cl.
CPC .............. *A61M 1/916* (2021.05); *A61M 1/95* (2021.05); *A61M 1/96* (2021.05); *A61M 1/98* (2021.05); *G16H 20/40* (2018.01); *G16H 30/40* (2018.01); *A61M 1/982* (2021.05); *A61M 2205/3306* (2013.01); *A61M 2205/3313* (2013.01); *A61M 2205/3569* (2013.01); *A61M 2205/3592* (2013.01); *A61M 2210/04* (2013.01); *A61M 2230/04* (2013.01)

(58) Field of Classification Search
CPC .. A61M 2205/3569; A61M 2205/3592; A61M 2210/04; A61M 2230/04; A61M 1/966; A61M 2205/3344; G16H 20/40; G16H 30/40; A61F 13/00068; A61B 5/0077; A61B 5/0261
See application file for complete search history.

(56) References Cited

U.S. PATENT DOCUMENTS

| | | | |
|---|---|---|---|
| 5,090,410 A | 2/1992 | Saper et al. |
| 5,253,654 A | 10/1993 | Thomas et al. |
| 5,635,201 A | 6/1997 | Fabo |
| 5,642,096 A | 6/1997 | Leyerer et al. |
| 5,678,448 A | 10/1997 | Fullen et al. |
| 5,690,610 A | 11/1997 | Ito et al. |
| 5,836,990 A | 11/1998 | Li |
| 6,095,992 A | 8/2000 | Augustine |
| 6,178,342 B1 | 1/2001 | Borgos et al. |
| 6,381,482 B1 | 4/2002 | Jayaraman et al. |
| 6,517,484 B1 | 2/2003 | Wilk et al. |
| 6,551,252 B2 | 4/2003 | Sackner et al. |
| 6,731,987 B1 | 5/2004 | McAdams et al. |
| 7,077,832 B2 | 7/2006 | Fleischmann |
| 7,088,591 B2 | 8/2006 | Kishimoto et al. |
| 7,201,063 B2 | 4/2007 | Taylor et al. |
| 7,206,623 B2 | 4/2007 | Blank et al. |
| 7,289,205 B2 | 10/2007 | Yaroslavsky et al. |
| 7,316,652 B2 | 1/2008 | Dalgaard et al. |
| 7,429,255 B2 | 9/2008 | Thompson |
| 7,520,875 B2 | 4/2009 | Bernabei |
| 7,521,292 B2 | 4/2009 | Rogers et al. |
| 7,569,742 B2 | 8/2009 | Haggstrom et al. |
| 7,625,117 B2 | 12/2009 | Haslett et al. |
| 7,687,678 B2 | 3/2010 | Jacobs |
| 7,838,717 B2 | 11/2010 | Haggstrom et al. |
| 7,846,141 B2 | 12/2010 | Weston |
| 7,877,866 B1 | 2/2011 | Greenberg et al. |
| 7,884,258 B2 | 2/2011 | Boehringer et al. |
| 7,904,133 B2 | 3/2011 | Gehman et al. |
| 7,922,676 B2 | 4/2011 | Daskal et al. |
| 7,942,869 B2 | 5/2011 | Houbolt et al. |
| 7,945,302 B2 | 5/2011 | McAdams |
| 8,019,401 B1 | 9/2011 | Smith et al. |
| 8,032,210 B2 | 10/2011 | Finneran et al. |
| 8,060,174 B2 | 11/2011 | Simpson et al. |
| 8,079,247 B2 | 12/2011 | Russell et al. |
| 8,111,165 B2 | 2/2012 | Ortega et al. |
| 8,116,841 B2 | 2/2012 | Bly et al. |
| 8,182,425 B2 | 5/2012 | Stamatas et al. |
| 8,207,392 B2 | 6/2012 | Haggstrom et al. |
| 8,238,996 B2 | 8/2012 | Burnes |
| 8,241,231 B2 | 8/2012 | Bausewein et al. |
| 8,332,053 B1 | 12/2012 | Patterson et al. |
| 8,333,874 B2 | 12/2012 | Currie et al. |
| 8,366,692 B2 | 2/2013 | Weston |
| 8,480,641 B2 | 7/2013 | Jacobs |
| 8,579,872 B2 | 11/2013 | Coulthard et al. |
| 8,644,911 B1 | 2/2014 | Panasyuk et al. |
| 8,663,106 B2 | 3/2014 | Stivoric et al. |
| 8,682,442 B2 | 3/2014 | McAdams |
| 8,783,948 B2 | 7/2014 | Panda et al. |
| 8,788,009 B2 | 7/2014 | Greene et al. |
| 8,800,386 B2 | 8/2014 | Taylor |
| 8,818,478 B2 | 8/2014 | Scheffler et al. |
| 8,829,263 B2 | 9/2014 | Haggstrom et al. |
| 8,848,187 B2 | 9/2014 | Uematsu et al. |
| 8,894,590 B2 | 11/2014 | Lamoise et al. |
| 8,925,392 B2 | 1/2015 | Esposito et al. |
| 8,934,957 B2 | 1/2015 | Dias et al. |
| 8,934,965 B2 | 1/2015 | Rogers et al. |
| 8,943,897 B2 | 2/2015 | Beauvais et al. |
| 8,945,030 B2 | 2/2015 | Weston |
| 8,948,839 B1 | 2/2015 | Longinotti-Buitoni et al. |
| 8,974,428 B2 | 3/2015 | Shuler et al. |
| 8,997,588 B2 | 4/2015 | Taylor |
| 9,000,251 B2 | 4/2015 | Murphy et al. |
| 9,042,075 B2 | 5/2015 | Borini et al. |
| 9,192,531 B2 | 11/2015 | Wu |
| 9,192,700 B2 | 11/2015 | Weston et al. |
| 9,204,806 B2 | 12/2015 | Stivoric et al. |
| 9,220,455 B2 | 12/2015 | Sarrafzadeh et al. |
| 9,226,402 B2 | 12/2015 | Hsu |
| 9,282,897 B2 | 3/2016 | Ross, Jr. et al. |
| 9,314,175 B2 | 4/2016 | Jacofsky et al. |
| 9,320,473 B2 | 4/2016 | Shuler |
| 9,372,123 B2 | 6/2016 | Li et al. |
| 9,378,450 B1 | 6/2016 | Mei et al. |
| 9,386,947 B2 | 7/2016 | Johnson |
| 9,393,354 B2 | 7/2016 | Freedman et al. |
| 9,402,988 B2 | 8/2016 | Buchanan et al. |
| 9,408,573 B2 | 8/2016 | Welch et al. |
| 9,427,179 B2 | 8/2016 | Mestrovic et al. |
| 9,439,599 B2 | 9/2016 | Thompson et al. |
| 9,483,726 B2 | 11/2016 | Mei et al. |
| 9,494,474 B2 | 11/2016 | Servati et al. |
| 9,511,215 B2 | 12/2016 | Skiba |
| 9,516,758 B2 | 12/2016 | Arora et al. |
| 9,526,439 B2 | 12/2016 | Connelly et al. |
| 9,554,484 B2 | 1/2017 | Rogers et al. |
| 9,572,507 B2 | 2/2017 | Moore et al. |
| 9,582,072 B2 | 2/2017 | Connor |
| 9,585,620 B2 | 3/2017 | Paquet et al. |
| 9,587,991 B2 | 3/2017 | Padiy |
| 9,592,007 B2 | 3/2017 | Nuovo et al. |
| 9,600,922 B2 * | 3/2017 | Tsukagoshi ............ G06T 15/08 |
| 9,603,560 B2 | 3/2017 | Monty et al. |
| 9,610,388 B2 | 4/2017 | Aceto et al. |
| 9,613,911 B2 | 4/2017 | Rogers et al. |
| 9,629,584 B2 | 4/2017 | Macia Barber et al. |
| 9,675,238 B2 | 6/2017 | Iida et al. |
| 9,687,195 B2 | 6/2017 | Sims et al. |
| 9,717,565 B2 | 8/2017 | Blair |
| 9,829,471 B2 | 11/2017 | Hammond et al. |
| 9,907,103 B2 | 2/2018 | Chen et al. |
| 9,999,711 B2 | 6/2018 | Weston et al. |
| 10,004,643 B2 | 6/2018 | Luckemeyer et al. |
| 10,046,096 B2 | 8/2018 | Askem et al. |
| 10,080,524 B1 | 9/2018 | Xi |
| 10,086,117 B2 | 10/2018 | Locke et al. |
| 10,117,705 B2 | 11/2018 | Chernov et al. |
| 10,152,789 B2 | 12/2018 | Carnes et al. |
| 10,182,740 B2 | 1/2019 | Tonar et al. |
| 10,201,644 B2 | 2/2019 | Haggstrom et al. |
| 10,207,031 B2 | 2/2019 | Toth |
| 10,209,213 B2 | 2/2019 | Kang et al. |
| 10,285,620 B2 | 5/2019 | Jung et al. |
| 10,288,590 B2 | 5/2019 | Hammond et al. |
| 10,321,862 B2 | 6/2019 | Dalene et al. |
| 10,398,353 B2 | 9/2019 | Addison et al. |
| 10,568,586 B2 | 2/2020 | Begin et al. |
| 10,857,038 B2 | 12/2020 | Zamierowski et al. |
| 11,026,847 B2 | 6/2021 | Piotrowski et al. |
| 11,234,643 B2 | 2/2022 | Nahmias et al. |
| 11,389,108 B2 | 7/2022 | Stroebech et al. |
| 11,647,922 B2 | 5/2023 | Scherer |
| 2002/0016536 A1 | 2/2002 | Benni |

(56) References Cited

U.S. PATENT DOCUMENTS

| | | |
|---|---|---|
| 2002/0135752 A1 | 9/2002 | Sokolov et al. |
| 2003/0033032 A1 | 2/2003 | Lind et al. |
| 2003/0208148 A1 | 11/2003 | Sullivan |
| 2003/0210810 A1 | 11/2003 | Gee, Jr. et al. |
| 2003/0216630 A1 | 11/2003 | Jersey-Willuhn et al. |
| 2004/0136579 A1 | 7/2004 | Gutenev |
| 2004/0230132 A1 | 11/2004 | Shehada |
| 2005/0088832 A1 | 4/2005 | Su et al. |
| 2005/0240107 A1 | 10/2005 | Alfano et al. |
| 2005/0280531 A1 | 12/2005 | Fadem et al. |
| 2006/0052678 A1 | 3/2006 | Drinan et al. |
| 2006/0058690 A1 | 3/2006 | Bartnik et al. |
| 2006/0181791 A1 | 8/2006 | Van Beek et al. |
| 2006/0234383 A1 | 10/2006 | Gough |
| 2006/0241495 A1 | 10/2006 | Kurtz |
| 2007/0055209 A1 | 3/2007 | Patel et al. |
| 2007/0173892 A1 | 7/2007 | Fleischer et al. |
| 2007/0191754 A1 | 8/2007 | Aali |
| 2007/0260421 A1 | 11/2007 | Berner, Jr. et al. |
| 2007/0293748 A1 | 12/2007 | Engvall et al. |
| 2008/0081973 A1 | 4/2008 | Hoarau |
| 2008/0167535 A1 | 7/2008 | Stivoric et al. |
| 2008/0194928 A1 | 8/2008 | Bandic et al. |
| 2008/0258717 A1 | 10/2008 | Igney et al. |
| 2008/0287747 A1 | 11/2008 | Mestrovic et al. |
| 2008/0319282 A1 | 12/2008 | Tran |
| 2008/0319283 A1 | 12/2008 | Cotton et al. |
| 2009/0149800 A1 | 6/2009 | Durand |
| 2009/0177051 A1 | 7/2009 | Arons et al. |
| 2009/0177110 A1 | 7/2009 | Lyden et al. |
| 2009/0209830 A1 | 8/2009 | Nagle et al. |
| 2009/0234206 A1 | 9/2009 | Gaspard et al. |
| 2009/0245601 A1 | 10/2009 | Cohen et al. |
| 2010/0022990 A1* | 1/2010 | Karpowicz ............ A61M 1/80 604/543 |
| 2010/0025831 A1 | 2/2010 | Yamazaki et al. |
| 2010/0101583 A1* | 4/2010 | Chen ............... A61B 5/02405 128/207.14 |
| 2010/0166252 A1 | 7/2010 | Ahmed et al. |
| 2010/0168727 A1 | 7/2010 | Hancock et al. |
| 2010/0268111 A1 | 10/2010 | Drinan et al. |
| 2010/0305473 A1 | 12/2010 | Yuzhakov |
| 2011/0004088 A1 | 1/2011 | Grossman |
| 2011/0015591 A1 | 1/2011 | Hanson et al. |
| 2011/0054283 A1 | 3/2011 | Shuler |
| 2011/0092958 A1* | 4/2011 | Jacobs ............... A61F 13/0216 604/543 |
| 2011/0130697 A1 | 6/2011 | Nagle et al. |
| 2011/0140703 A1 | 6/2011 | Chiao et al. |
| 2011/0190639 A1 | 8/2011 | Peltie et al. |
| 2011/0218757 A1 | 9/2011 | Callsen et al. |
| 2011/0242532 A1 | 10/2011 | McKenna |
| 2011/0245682 A1 | 10/2011 | Robinson et al. |
| 2011/0301441 A1 | 12/2011 | Bandic et al. |
| 2012/0029306 A1 | 2/2012 | Paquet et al. |
| 2012/0029307 A1 | 2/2012 | Paquet et al. |
| 2012/0029410 A1 | 2/2012 | Koenig et al. |
| 2012/0084064 A1* | 4/2012 | Dzenis ................. G16H 50/50 703/11 |
| 2012/0112347 A1 | 5/2012 | Eckhardt et al. |
| 2012/0165717 A1 | 6/2012 | Al Khaburi et al. |
| 2012/0190956 A1 | 7/2012 | Connolly |
| 2012/0190989 A1 | 7/2012 | Kaiser et al. |
| 2012/0265120 A1 | 10/2012 | Beisang, III et al. |
| 2012/0271265 A1 | 10/2012 | Langdon |
| 2012/0277559 A1 | 11/2012 | Kohl-Bareis et al. |
| 2012/0316538 A1 | 12/2012 | Heiser et al. |
| 2012/0330252 A1 | 12/2012 | Stokes et al. |
| 2013/0041235 A1 | 2/2013 | Rogers et al. |
| 2013/0064772 A1 | 3/2013 | Swiss et al. |
| 2013/0121544 A1 | 5/2013 | Sarrafzadeh et al. |
| 2013/0123722 A1 | 5/2013 | Pratt et al. |
| 2013/0151223 A1 | 6/2013 | Zamierowski et al. |
| 2013/0190655 A1 | 7/2013 | Jackson et al. |
| 2013/0200268 A1 | 8/2013 | Rafferty et al. |
| 2013/0261409 A1 | 10/2013 | Pathak et al. |
| 2013/0271278 A1 | 10/2013 | Duesterhoft et al. |
| 2013/0274563 A1 | 10/2013 | Duesterhoft et al. |
| 2013/0274629 A1 | 10/2013 | Duesterhoft et al. |
| 2013/0317367 A1 | 11/2013 | Shuler |
| 2013/0338480 A1* | 12/2013 | Hann ..................... A61M 5/158 600/409 |
| 2014/0012108 A1 | 1/2014 | McPeak |
| 2014/0018637 A1 | 1/2014 | Bennett et al. |
| 2014/0024905 A1 | 1/2014 | Sarrafzadeh et al. |
| 2014/0031663 A1 | 1/2014 | Gallego et al. |
| 2014/0072190 A1* | 3/2014 | Wu ........................ G06T 7/0016 382/128 |
| 2014/0075658 A1 | 3/2014 | McGuin |
| 2014/0107495 A1 | 4/2014 | Marinelli et al. |
| 2014/0107498 A1 | 4/2014 | Bower et al. |
| 2014/0147611 A1 | 5/2014 | Ackerman, Jr. et al. |
| 2014/0203797 A1 | 7/2014 | Stivoric et al. |
| 2014/0206947 A1 | 7/2014 | Isserow et al. |
| 2014/0232516 A1 | 8/2014 | Stivoric et al. |
| 2014/0235166 A1 | 8/2014 | Molettiere et al. |
| 2014/0243709 A1 | 8/2014 | Gibson et al. |
| 2014/0296749 A1 | 10/2014 | Reid, Jr. et al. |
| 2014/0298927 A1 | 10/2014 | Allin et al. |
| 2014/0298928 A1* | 10/2014 | Duesterhoft ........... A61B 5/445 73/865.8 |
| 2014/0303463 A1 | 10/2014 | Robinson et al. |
| 2014/0313303 A1 | 10/2014 | Davis et al. |
| 2014/0324120 A1 | 10/2014 | Bogie et al. |
| 2014/0340857 A1 | 11/2014 | Hsu et al. |
| 2014/0343478 A1 | 11/2014 | Brennan et al. |
| 2014/0350882 A1 | 11/2014 | Everett et al. |
| 2015/0018792 A1 | 1/2015 | Marsiquet et al. |
| 2015/0025343 A1 | 1/2015 | Gareau et al. |
| 2015/0138330 A1 | 5/2015 | Krishnamoorthi |
| 2015/0141767 A1 | 5/2015 | Rogers et al. |
| 2015/0148760 A1* | 5/2015 | Dodd ............... A61B 17/06166 604/319 |
| 2015/0150479 A1 | 6/2015 | Yoshino et al. |
| 2015/0182166 A1 | 7/2015 | Evans et al. |
| 2015/0223716 A1 | 8/2015 | Korkala et al. |
| 2015/0257644 A1 | 9/2015 | Cao |
| 2015/0265191 A1 | 9/2015 | Harding et al. |
| 2015/0292968 A1 | 10/2015 | Vogt et al. |
| 2015/0310598 A1* | 10/2015 | Rooney ................. A61K 49/106 382/131 |
| 2015/0313476 A1 | 11/2015 | Pisani et al. |
| 2015/0313533 A1 | 11/2015 | Rapp et al. |
| 2015/0324634 A1 | 11/2015 | Brosens-Kessels et al. |
| 2015/0327777 A1 | 11/2015 | Kostic et al. |
| 2015/0335254 A1 | 11/2015 | Fastert et al. |
| 2015/0335288 A1 | 11/2015 | Toth et al. |
| 2015/0351970 A1 | 12/2015 | Dagger et al. |
| 2015/0359485 A1 | 12/2015 | Berg et al. |
| 2015/0374309 A1 | 12/2015 | Farkas et al. |
| 2016/0015962 A1 | 1/2016 | Shokoueinejad Maragheh |
| 2016/0022223 A1 | 1/2016 | Grundfest et al. |
| 2016/0029900 A1 | 2/2016 | LaPlante et al. |
| 2016/0030132 A1 | 2/2016 | Cheung et al. |
| 2016/0038045 A1 | 2/2016 | Shapiro |
| 2016/0038083 A1 | 2/2016 | Ding et al. |
| 2016/0051147 A1 | 2/2016 | Cohen et al. |
| 2016/0058380 A1 | 3/2016 | Lee et al. |
| 2016/0066854 A1 | 3/2016 | Mei et al. |
| 2016/0069743 A1 | 3/2016 | McQuilkin et al. |
| 2016/0074234 A1 | 3/2016 | Abichandi et al. |
| 2016/0081580 A1 | 3/2016 | Bergelin et al. |
| 2016/0081601 A1 | 3/2016 | Ballam et al. |
| 2016/0100790 A1 | 4/2016 | Cantu et al. |
| 2016/0100987 A1 | 4/2016 | Hartwell et al. |
| 2016/0101282 A1 | 4/2016 | Bergelin et al. |
| 2016/0129186 A1* | 5/2016 | Douglas ................. G16H 40/63 601/84 |
| 2016/0129469 A1 | 5/2016 | Kulinsky et al. |
| 2016/0143534 A1 | 5/2016 | Hyde et al. |
| 2016/0157779 A1 | 6/2016 | Baxi et al. |
| 2016/0165719 A1 | 6/2016 | Li et al. |
| 2016/0166438 A1 | 6/2016 | Rovaniemi |

(56) References Cited

U.S. PATENT DOCUMENTS

| | | | |
|---|---|---|---|
| 2016/0198965 A1* | 7/2016 | Mestha | A61B 5/0013 600/473 |
| 2016/0213269 A1 | 7/2016 | Lam et al. | |
| 2016/0228049 A1 | 8/2016 | Nackaerts et al. | |
| 2016/0232807 A1 | 8/2016 | Ghaffari et al. | |
| 2016/0242331 A1 | 8/2016 | Park et al. | |
| 2016/0249810 A1 | 9/2016 | Darty et al. | |
| 2016/0262625 A1* | 9/2016 | Lawrenson | A61B 5/0077 |
| 2016/0262672 A1 | 9/2016 | Hammond et al. | |
| 2016/0262687 A1 | 9/2016 | Vaidyanathan et al. | |
| 2016/0270700 A1 | 9/2016 | Baxi et al. | |
| 2016/0287177 A1 | 10/2016 | Huppert et al. | |
| 2016/0302729 A1 | 10/2016 | Starr et al. | |
| 2016/0310023 A1 | 10/2016 | Chachisvilis et al. | |
| 2016/0317057 A1 | 11/2016 | Li et al. | |
| 2016/0331263 A1 | 11/2016 | Cailler et al. | |
| 2016/0331322 A1 | 11/2016 | Son et al. | |
| 2016/0338591 A1 | 11/2016 | Lachenbruch et al. | |
| 2016/0354001 A1 | 12/2016 | Buckley et al. | |
| 2016/0367189 A1 | 12/2016 | Aimone et al. | |
| 2016/0367192 A1 | 12/2016 | Iyengar et al. | |
| 2016/0367406 A1 | 12/2016 | Barnett | |
| 2017/0000407 A1 | 1/2017 | Saxby et al. | |
| 2017/0007853 A1 | 1/2017 | Alford et al. | |
| 2017/0014556 A1 | 1/2017 | Haggstrom et al. | |
| 2017/0027498 A1 | 2/2017 | Larson et al. | |
| 2017/0079530 A1 | 3/2017 | DiMaio et al. | |
| 2017/0079740 A1 | 3/2017 | Hufnagel et al. | |
| 2017/0086519 A1 | 3/2017 | Vigano et al. | |
| 2017/0086709 A1 | 3/2017 | Khine et al. | |
| 2017/0095208 A1 | 4/2017 | Oberleitner et al. | |
| 2017/0119258 A1* | 5/2017 | Kotanko | A61B 5/6824 |
| 2017/0146474 A1 | 5/2017 | Bedell et al. | |
| 2017/0156594 A1 | 6/2017 | Stivoric et al. | |
| 2017/0156621 A1 | 6/2017 | Bettinger et al. | |
| 2017/0156658 A1 | 6/2017 | Maharbiz et al. | |
| 2017/0164865 A1 | 6/2017 | Rafferty et al. | |
| 2017/0164876 A1 | 6/2017 | Hyde et al. | |
| 2017/0172439 A1 | 6/2017 | Zhu et al. | |
| 2017/0202711 A1 | 7/2017 | Cernasov et al. | |
| 2017/0224271 A1 | 8/2017 | Lachenbruch et al. | |
| 2017/0231015 A1 | 8/2017 | Jang et al. | |
| 2017/0258972 A1 | 9/2017 | Weston | |
| 2017/0304510 A1 | 10/2017 | Askem et al. | |
| 2017/0319075 A1 | 11/2017 | Homan et al. | |
| 2017/0326004 A1 | 11/2017 | Long et al. | |
| 2017/0367644 A1 | 12/2017 | Sharman et al. | |
| 2018/0008177 A1 | 1/2018 | Shimuta et al. | |
| 2018/0055359 A1 | 3/2018 | Shamim et al. | |
| 2018/0055697 A1 | 3/2018 | Mihali et al. | |
| 2018/0056087 A1 | 3/2018 | Ribiero et al. | |
| 2018/0070880 A1 | 3/2018 | Trembly et al. | |
| 2018/0074547 A1 | 3/2018 | Smadi et al. | |
| 2018/0116877 A1 | 5/2018 | Ineichen | |
| 2018/0132287 A1 | 5/2018 | Cheng et al. | |
| 2018/0192514 A1 | 7/2018 | Seo | |
| 2018/0200414 A1 | 7/2018 | Askem et al. | |
| 2018/0206758 A1 | 7/2018 | Feldkamp et al. | |
| 2018/0235484 A1 | 8/2018 | Mozdzierz | |
| 2018/0296397 A1 | 10/2018 | Askem et al. | |
| 2018/0317774 A1 | 11/2018 | Sgroi, Jr. | |
| 2019/0001032 A1 | 1/2019 | Weston et al. | |
| 2019/0021911 A1 | 1/2019 | Askem et al. | |
| 2019/0060126 A1 | 2/2019 | Ribble et al. | |
| 2019/0076298 A1 | 3/2019 | Quintanar et al. | |
| 2019/0083025 A1 | 3/2019 | Aung et al. | |
| 2019/0117379 A1 | 4/2019 | Quiros et al. | |
| 2019/0133812 A1 | 5/2019 | Seres et al. | |
| 2019/0134280 A1 | 5/2019 | Toth | |
| 2019/0159938 A1 | 5/2019 | Askem et al. | |
| 2019/0175098 A1 | 6/2019 | Burns | |
| 2019/0192066 A1 | 6/2019 | Schoess et al. | |
| 2019/0231939 A1 | 8/2019 | Askem et al. | |
| 2019/0290496 A1 | 9/2019 | Brownhill et al. | |
| 2019/0388142 A1 | 12/2019 | Chernov et al. | |
| 2020/0000394 A1 | 1/2020 | Hutchinson et al. | |
| 2020/0147407 A1 | 5/2020 | Efremkin | |
| 2020/0330258 A1 | 10/2020 | Hansen et al. | |
| 2021/0212855 A1 | 7/2021 | Hansen et al. | |
| 2022/0079814 A1 | 3/2022 | Chen et al. | |

FOREIGN PATENT DOCUMENTS

| | | |
|---|---|---|
| CN | 105232229 | 1/2016 |
| CN | 105395184 | 3/2016 |
| CN | 106102322 | 11/2016 |
| DE | 10 2012 211015 | 1/2014 |
| DE | 10 2013 013013 | 2/2015 |
| EP | 2 454 990 | 5/2012 |
| EP | 2 565 630 | 3/2013 |
| EP | 2 574 275 | 4/2013 |
| EP | 1 854 342 | 6/2014 |
| EP | 1 734 858 | 7/2014 |
| EP | 2 773 393 A2 | 9/2014 |
| EP | 2 451 349 | 4/2016 |
| EP | 2 941 195 | 12/2016 |
| EP | 3 231 478 | 10/2017 |
| EP | 3 409 190 | 12/2018 |
| EP | 3 499 510 | 6/2019 |
| GB | 1476894 | 6/1977 |
| GB | 2316171 | 2/1998 |
| GB | 2563602 | 12/2018 |
| JP | 2009-225863 | 10/2009 |
| KR | 10 2012 0119523 | 10/2012 |
| KR | 101224629 B1 | 1/2013 |
| KR | 10 2014 0024743 | 3/2014 |
| KR | 10 2014 0058041 | 5/2014 |
| KR | 10 2016 0071044 | 6/2016 |
| KR | 20190105898 A | 9/2019 |
| NL | 1 027 236 | 4/2006 |
| WO | WO 2000/021433 | 4/2000 |
| WO | WO 2000/043046 | 7/2000 |
| WO | WO-02083046 A1 | 10/2002 |
| WO | WO 2003/067229 | 8/2003 |
| WO | WO-03105689 A1 | 12/2003 |
| WO | WO 2006/041997 | 4/2006 |
| WO | WO 2007/030379 | 3/2007 |
| WO | WO-2007144810 A1 | 12/2007 |
| WO | WO 2008/006150 | 1/2008 |
| WO | WO 2008/010604 | 1/2008 |
| WO | WO 2009/052607 | 4/2009 |
| WO | WO 2009/120951 | 10/2009 |
| WO | WO 2009/141777 | 11/2009 |
| WO | WO 2010/020919 | 2/2010 |
| WO | WO-2010015863 A1 | 2/2010 |
| WO | WO 2010/105053 | 9/2010 |
| WO | WO 2011/082420 | 7/2011 |
| WO | WO 2011/113070 | 9/2011 |
| WO | WO 2011/123848 | 10/2011 |
| WO | WO 2012/141999 | 10/2012 |
| WO | WO 2013/026999 | 2/2013 |
| WO | WO 2013/044226 | 3/2013 |
| WO | WO 2013/155193 | 10/2013 |
| WO | WO 2014/036577 | 3/2014 |
| WO | WO-2014116816 A1 | 7/2014 |
| WO | WO 2015/112095 | 7/2015 |
| WO | WO 2015/168720 | 11/2015 |
| WO | WO 2016/025438 | 2/2016 |
| WO | WO 2016/030752 | 3/2016 |
| WO | WO 2016/058032 | 4/2016 |
| WO | WO-2016073777 A1 | 5/2016 |
| WO | WO 2016/100218 | 6/2016 |
| WO | WO 2016/109744 | 7/2016 |
| WO | WO 2016/110564 | 7/2016 |
| WO | WO-2016164904 A1 | 10/2016 |
| WO | WO 2016/187136 | 11/2016 |
| WO | WO 2016/205872 | 12/2016 |
| WO | WO 2016/205881 | 12/2016 |
| WO | WO 2017/021006 | 2/2017 |
| WO | WO 2017/021965 | 2/2017 |
| WO | WO 2017/033058 | 3/2017 |
| WO | WO 2017/037479 | 3/2017 |
| WO | WO 2017/041014 | 3/2017 |
| WO | WO 2017/041386 | 3/2017 |

(56) References Cited

FOREIGN PATENT DOCUMENTS

| WO | WO 2017/041387 | 3/2017 |
|---|---|---|
| WO | WO-2017041385 A1 | 3/2017 |
| WO | WO-2017079387 A1 | 5/2017 |
| WO | WO 2017/119996 | 7/2017 |
| WO | WO 2017/205728 | 11/2017 |
| WO | WO 2017/214188 | 12/2017 |
| WO | WO 2018/035612 | 3/2018 |
| WO | WO 2018/064569 | 4/2018 |
| WO | WO-2018060417 A1 | 4/2018 |
| WO | WO 2018/115461 | 6/2018 |
| WO | WO 2018/144938 | 8/2018 |
| WO | WO 2018/144941 | 8/2018 |
| WO | WO 2018/144943 | 8/2018 |
| WO | WO 2018/144946 | 8/2018 |
| WO | WO 2018/162728 | 9/2018 |
| WO | WO 2018/162732 | 9/2018 |
| WO | WO 2018/162735 | 9/2018 |
| WO | WO 2018/162736 | 9/2018 |
| WO | WO 2018/185138 | 10/2018 |
| WO | WO 2018/189265 | 10/2018 |
| WO | WO 2018/209090 | 11/2018 |
| WO | WO 2018/210692 | 11/2018 |
| WO | WO 2018/210693 | 11/2018 |
| WO | WO 2018/211458 | 11/2018 |
| WO | WO 2018/234443 | 12/2018 |
| WO | WO 2019/020550 | 1/2019 |
| WO | WO 2019/020551 | 1/2019 |
| WO | WO 2019/020666 | 1/2019 |
| WO | WO 2019/030384 | 2/2019 |
| WO | WO 2019/048624 | 3/2019 |
| WO | WO 2019/048626 | 3/2019 |
| WO | WO 2019/048638 | 3/2019 |
| WO | WO 2019/063481 | 4/2019 |
| WO | WO 2019/063488 | 4/2019 |
| WO | WO 2019/067264 | 4/2019 |
| WO | WO 2019/072531 | 4/2019 |
| WO | WO 2019/076967 | 4/2019 |
| WO | WO 2019/096828 | 5/2019 |
| WO | WO 2019/140441 | 7/2019 |
| WO | WO 2019/140444 | 7/2019 |
| WO | WO 2019/140448 | 7/2019 |
| WO | WO 2019/140449 | 7/2019 |
| WO | WO-2019193141 A1 | 10/2019 |
| WO | WO-2019216883 A1 | 11/2019 |

OTHER PUBLICATIONS

International Search Report and Written Opinion, re PCT Application No. PCT/EP2018/062207, dated Aug. 29, 2018.
"Little Miss Plasters", kidstravelclub.co.uk., accessed Aug. 26, 2016, in 2 pages. URL: http://www.kidstravelclub.co.uk/little-miss-girls-childrens-plasters.
Aubakir, B. et al., "Vital Sign Monitoring Utilizing Eulerian Video Magnification and Thermography", 2016 38th Annual International Conference of the IEEE Engineering in Medicine and Biology Society, Aug. 16, 2016, pp. 3527-3530, in 4 pages.
Bandodkar, A. et al., "Battery-free, skin-interfaced microfluidic/electronic systems for simultaneous electrochemical, colorimetric, and volumetric analysis of sweat", Science Advances, vol. 5(1), Jan. 18, 2019, in 16 pages. URL: http://advances.sciencemag.org/content/5/1/eaav3294.
Cauwe, M. et al., "Technology development for a low-cost, roll-to-roll chip embedding solution based on PET foils", 18th European Microelectronics and Packaging Conference (EMPC), IEEE, Sep. 12, 2011, in 6 pages.
Farooqui, M. et al., "Low Cost Inkjet Printed Smart Bandage for Wireless Monitoring of Chronic Wounds", Scientific Reports, vol. 6, Jun. 29, 2016, in 14 pages.
Geng, Y. et al., "A Hybrid Low Power Biopatch for Body Surface Potential Measurement", IEEE Journal of Biomedical and Health Informatics, vol. 17(3), May 1, 2013, XP011506375.
Iannetta, R.A. et al., "Successful case histories of polymer based circuitry on flexible film substrates", Electro/94 International Conference Proceedings Combined Volumes, IEEE, May 10-12, 1994, XP010149465.
Jinto, G. et al., "Reliability of Plastic-Encapsulated Electronic Components in Supersaturated Steam Environments", IEEE Transactions on Components, Packaging, and Manufacturing Technology, vol. 5, No. 10, Oct. 2015, in 9 pages.
Lu, B. et al., "A study of the autofluorescence of parylene materials for [mu]TAS applications", Lab on Chip, vol. 10, No. 14, Jul. 2010, pp. 1826-1834, in 9 pages.
McLeod, A. et al., "Motion Magnification for Endoscopic Surgery", Progress in Biomedical Optics and Imaging, SPIE—International Society for Optical Engineering, Mar. 12, 2014, vol. 9036, in 8 pages.
Mostafalu, P. et al., "Wireless Flexible Smart Bandage for Continuous Monitoring of Wound Oxygenation", IEEE Transactions on Biomedical Circuits and Systems, vol. 9, No. 5, Oct. 2015, pp. 670-677, in 8 pages.
Narusawa, H., "The corona discharge causes short destruction that had bad influence on a power switching circuit", Adphox Corporation, Jan. 1, 2009, in 12 pages. URL: http://www.adphox.co.jp/keisokuki/ke-english-corona/CORONA_DISCHARGE_EN.pdf.
Raviglione, A. et al., "Real-Time Smart Textile-Based System to Monitor Pressure Offloading of Diabetic Foot Ulcers", Journal of Diabetes Science and Technology, vol. 11, Sep. 2017, in 5 pages.
Rose, D. et al., "Adhesive RFID Sensor Patch for Monitoring of Sweat Electrolytes", IEEE Transactions on Biomedical Engineering, vol. 62(6), Jun. 2015 (first published Nov. 11, 2015), in 9 pages.
Wakita, J. et al., "Variations in Optical Absorption and Fluorescence Spectra for Polyimide Thin Films Caused by Structural Isomerism", J. Photopolym. Sci. Technol. Jan. 1, 2003, in 1 page.
Willis, B., "Conformal Coating Inspection & Coating Faults", Vision Engineering, Jul. 21, 2016, in 35 pages. URL: http://www.visioneng.com/wp-content/uploads/2017/11/Confirmal-Coating-Inspection-and-Defects.21JUL16.pdf.
Willis, B., "Guide to Conformal Coating & Cleaning Defects Contents", Mar. 1, 2014, in 31 pages. URL: http://coatingguide.smartgroup.org/Files%20pdf/Coating%20Defects%20V2%2014March2014.pdf.
International Preliminary Report on Patentability for Application No. PCT/EP2018/062207, dated Nov. 28, 2019, 16 pages.
Mehmood N., et al., "Applications of Modern Sensors And Wireless Technology In Effective Wound Management: Modern Sensors And Wireless Technology," Journal of Biomedical Materials Research Part B, vol. 102, May 1, 2014, XP055739544, pp. 885-895.

* cited by examiner

PICO™

| Setting | Nominal Set point | Pressure lower set-point (more vacuum) CALDATA_MIN_PRESSURE | Pressure upper set-point (less vacuum) CALDATA_MAX_PRESSURE |
|---|---|---|---|
| 1 | -40mmHg | -45mmHg | -35mmHg |
| 2 | -50mmHg | -55mmHg | -45mmHg |
| 3 | -60mmHg | -70mmHg | -50mmHg |
| 4 | -80mmHg | -90mmHg | -70mmHg |
| 5 | -100mmHg | -110mmHg | -90mmHg |
| 6 | -120mmHg | -130mmHg | -110mmHg |
| 7 | -150mmHg | -165mmHg | -135mmHg |

FIG. 11A

| RENASYS™ | |
|---|---|
| Setting | Set point for PI loop |
| 1 | -40mmHg |
| 2 | -50mmHg |
| 3 | -60mmHg |
| 4 | -80mmHg |
| 5 | -100mmHg |
| 6 | -120mmHg |
| 7 | -150mmHg |
| 8 | -175mmHg |
| 9 | -200mmHg |
| 10 | -235mmHg |
| 11 | -280mmHg |

FIG. 11B

NEGATIVE PRESSURE WOUND THERAPY SYSTEM USING EULERIAN VIDEO MAGNIFICATION

CROSS-REFERENCE TO RELATED APPLICATIONS

This application is a U.S. national stage application of International Patent Application No. PCT/EP2018/062207, filed May 11, 2018, which claims the benefit of U.S. Provisional Application No. 62/506,524, filed May 15, 2017; the disclosure of which is hereby incorporated by reference in its entirety.

BACKGROUND

Technical Field

Embodiments described herein relate to apparatuses, systems, and methods for the treatment of wounds, for example using dressings in combination with wound monitoring and negative pressure wound therapy.

Description of the Related Art

The treatment of open or chronic wounds that are too large to spontaneously close or otherwise fail to heal by means of applying negative pressure to the site of the wound is well known in the art. Negative pressure wound therapy (NPWT) systems currently known in the art commonly involve placing a cover that is impermeable or semi-permeable to fluids over the wound, using various means to seal the cover to the tissue of the patient surrounding the wound, and connecting a source of negative pressure (such as a vacuum pump) to the cover in a manner so that negative pressure is created and maintained under the cover. It is believed that such negative pressures promote wound healing by facilitating the formation of granulation tissue at the wound site and assisting the body's normal inflammatory process while simultaneously removing excess fluid, which may contain adverse cytokines and/or bacteria. However, further improvements in NPWT are needed to fully realize the benefits of treatment.

Many different types of wound dressings are known for aiding in NPWT systems. These different types of wound dressings include many different types of materials and layers, for example, gauze, pads, foam pads or multi-layer wound dressings. One example of a multi-layer wound dressing is the PICO dressing, available from Smith & Nephew, which includes a wound contact layer and a superabsorbent layer beneath a backing layer to provide a canister-less system for treating a wound with NPWT. The wound dressing may be sealed to a suction port providing connection to a length of tubing, which may be used to pump fluid out of the dressing and/or to transmit negative pressure from a pump to the wound dressing. Additionally, RENASYS-F, RENASYS-G, RENASYS-AB, and RENASYS-F/AB, available from Smith & Nephew, are additional examples of NPWT wound dressings and systems. Another example of a multi-layer wound dressing is the ALLEVYN Life dressing, available from Smith & Nephew, which includes a moist wound environment dressing that is used to treat the wound without the use of negative pressure.

However, prior art dressings for use in negative pressure wound therapy or other wound therapy provide little visualization or information of the condition of the wound site beneath the dressing. This can require the dressing to be changed prematurely before the desired level of wound healing has occurred or, for absorbent dressings, prior to the full absorbent capacity of the dressing being reached to allow the clinician to inspect the healing and status of the wound. Some current dressings have limited and/or unsatisfactory methods or features of providing information of conditions of the wound.

Further, existing techniques may provide inadequate information about the state of tissue before a wound exists, such as before formation of a pressure ulcer. Therefore, improved methods and techniques for evaluating/detecting changes within wounds and tissue are needed.

SUMMARY

Certain disclosed embodiments relate to devices, methods, and systems for monitoring tissues. It will be understood by one of skill in the art that application of the devices, methods, and systems described herein are not limited to a particular tissue or a particular injury.

In some embodiments, a wound therapy system comprises a source of negative pressure configured to be in fluidic communication with a wound dressing placed over a wound, the source of negative pressure configured to provide negative pressure under the wound dressing, a visualization sensor positioned above the wound, the visualization sensor configured to collect video data of the wound, and a controller in communication with both the source of negative pressure and the visualization sensor, the controller configured to: determine a treatment factor from the video data, and cause the source of negative pressure to increase or decrease a level of provided negative pressure if the treatment factor differs from a threshold.

In some embodiments, the controller may be further configured to amplify the video data by Eulerian video magnification. The treatment factor may be determined from differences between region values measured in the video data. The video data may comprise RGB color data. The visualization sensor may be configured to communicate wirelessly with the controller. The controller may be configured to communicate wirelessly with the source of negative pressure. The controller may be configured to transmit a signal to the source of negative pressure to increase negative pressure if the treatment parameter is below the desired value. The controller may be configured to cause the source of negative pressure to decrease the level of provided negative pressure if the treatment parameter is above the threshold. The controller may be configured to compare the treatment parameter to a plurality of thresholds. The controller may be configured to perform the comparison using a lookup table. The treatment parameter may indicate blood flow in the wound. The threshold may correspond to a desired level of blood flow in the wound.

Further embodiments are described below.

BRIEF DESCRIPTION OF THE DRAWINGS

FIG. 11A is an embodiment of a treatment lookup table using a PICO™ pump.

FIG. 11B is an embodiment of a treatment lookup table using a RENASYS™ pump.

DETAILED DESCRIPTION

Figure 1:
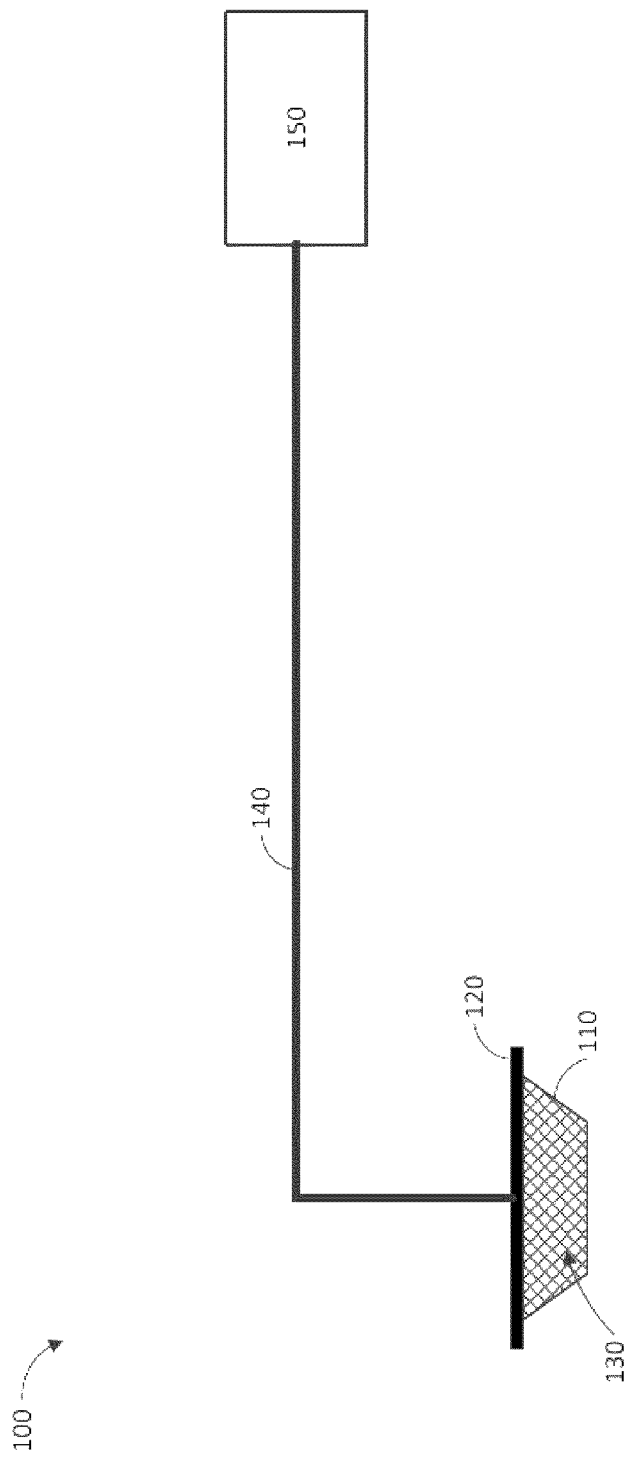
FIG. 1 illustrates a reduced pressure wound therapy system according to some embodiments.

Embodiments disclosed herein relate to apparatuses and methods of monitoring and treating biological tissue with sensor-enabled substrates. The embodiments disclosed herein are not limited to treatment or monitoring of a particular type of tissue or injury, instead the sensor-enabled technologies disclosed herein are broadly applicable to any type of therapy that may benefit from sensor-enabled substrates. Some implementations utilize sensors and data collection relied upon by health care providers to make both diagnostic and patient management decisions.

Some embodiments disclosed herein relate to the use of sensors mounted on or embedded within substrates configured to be used in the treatment of both intact and damaged human or animal tissue. Such sensors may collect information about the surrounding tissue and transmit such information to a computing device or a caregiver to be utilized in further treatment. In certain embodiments, such sensors may be attached to the skin anywhere on the body, including areas for monitoring arthritis, temperature, or other areas that may be prone to problems and require monitoring. Sensors disclosed herein may also incorporate markers, such as radiopaque markers, to indicate the presence of the device, for example prior to performing an MRI or other technique.

The sensor embodiments disclosed herein may be used in combination with clothing. Non-limiting examples of clothing for use with embodiments of the sensors disclosed herein include shirts, pants, trousers, dresses, undergarments, outer-garments, gloves, shoes, hats, and other suitable garments. In certain embodiments, the sensor embodiments disclosed herein may be welded into or laminated into/onto the particular garments. The sensor embodiments may be printed directly onto the garment and/or embedded into the fabric. Breathable and printable materials such as microporous membranes may also be suitable.

Sensor embodiments disclosed herein may be incorporated into cushioning or bed padding, such as within a hospital bed, to monitor patient characteristics, such as any characteristic disclosed herein. In certain embodiments, a disposable film containing such sensors could be placed over the hospital bedding and removed/replaced as needed.

In some implementations, the sensor embodiments disclosed herein may incorporate energy harvesting, such that the sensor embodiments are self-sustaining. For example, energy may be harvested from thermal energy sources, kinetic energy sources, chemical gradients, or any suitable energy source.

The sensor embodiments disclosed herein may be utilized in rehabilitation devices and treatments, including sports medicine. For example, the sensor embodiments disclosed herein may be used in braces, sleeves, wraps, supports, and other suitable items. Similarly, the sensor embodiments disclosed herein may be incorporated into sporting equipment, such as helmets, sleeves, and/or pads. For example, such sensor embodiments may be incorporated into a protective helmet to monitor characteristics such as acceleration, which may be useful in concussion diagnosis.

The sensor embodiments disclosed herein may be used in coordination with surgical devices, for example, the NAVIO surgical system by Smith & Nephew Inc. In implementations, the sensor embodiments disclosed herein may be in communication with such surgical devices to guide placement of the surgical devices. In some implementations, the sensor embodiments disclosed herein may monitor blood flow to or away from the potential surgical site or ensure that there is no blood flow to a surgical site. Further surgical data may be collected to aid in the prevention of scarring and monitor areas away from the impacted area.

To further aid in surgical techniques, the sensors disclosed herein may be incorporated into a surgical drape to provide information regarding tissue under the drape that may not be immediately visible to the naked eye. For example, a sensor embedded flexible drape may have sensors positioned advantageously to provide improved area-focused data collection. In certain implementations, the sensor embodiments disclosed herein may be incorporated into the border or interior of a drape to create fencing to limit/control the surgical theater.

Sensor embodiments as disclosed herein may also be utilized for pre-surgical assessment. For example, such sensor embodiments may be used to collect information about a potential surgical site, such as by monitoring skin and the underlying tissues for a possible incision site. For example, perfusion levels or other suitable characteristics may be monitored at the surface of the skin and deeper in the tissue to assess whether an individual patient may be at risk for surgical complications. Sensor embodiments such as those disclosed herein may be used to evaluate the presence of microbial infection and provide an indication for the use of antimicrobials. Further, sensor embodiments disclosed herein may collect further information in deeper tissue, such as identifying pressure ulcer damage and/or the fatty tissue levels.

The sensor embodiments disclosed herein may be utilized in cardiovascular monitoring. For example, such sensor embodiments may be incorporated into a flexible cardiovascular monitor that may be placed against the skin to monitor characteristics of the cardiovascular system and communicate such information to another device and/or a caregiver. For example, such a device may monitor pulse rate, oxygenation of the blood, and/or electrical activity of the heart. Similarly, the sensor embodiments disclosed herein may be utilized for neurophysiological applications, such as monitoring electrical activity of neurons.

The sensor embodiments disclosed herein may be incorporated into implantable devices, such as implantable orthopedic implants, including flexible implants. Such sensor embodiments may be configured to collect information regarding the implant site and transmit this information to an external source. In some embodiments, an internal source may also provide power for such an implant.

The sensor embodiments disclosed herein may also be utilized for monitoring biochemical activity on the surface of the skin or below the surface of the skin, such as lactose buildup in muscle or sweat production on the surface of the skin. In some embodiments, other characteristics may be monitored, such as glucose concentration, urine concentration, tissue pressure, skin temperature, skin surface conductivity, skin surface resistivity, skin hydration, skin maceration, and/or skin ripping.

Sensor embodiments as disclosed herein may be incorporated into Ear, Nose, and Throat (ENT) applications. For example, such sensor embodiments may be utilized to monitor recovery from ENT-related surgery, such as wound monitoring within the sinus passage.

As described in greater detail below, the sensor embodiments disclosed herein may encompass sensor printing technology with encapsulation, such as encapsulation with a polymer film Such a film may be constructed using any polymer described herein, such as polyurethane. Encapsulation of the sensor embodiments may provide waterproofing of the electronics and protection from local tissue, local fluids, and other sources of potential damage.

In certain embodiments, the sensors disclosed herein may be incorporated into an organ protection layer such as disclosed below. Such a sensor-embedded organ protection layer may both protect the organ of interest and confirm that the organ protection layer is in position and providing protection. Further, a sensor-embedded organ protection layer may be utilized to monitor the underlying organ, such as by monitoring blood flow, oxygenation, and other suitable markers of organ health. In some embodiments, a sensor-enabled organ protection layer may be used to monitor a transplanted organ, such as by monitoring the fat and muscle content of the organ. Further, sensor-enabled organ protection layers may be used to monitor an organ during and after transplant, such as during rehabilitation of the organ.

The sensor embodiments disclosed herein may be incorporated into treatments for wounds (disclosed in greater detail below) or in a variety of other applications. Non-limiting examples of additional applications for the sensor embodiments disclosed herein include: monitoring and treatment of intact skin, cardiovascular applications such as monitoring blood flow, orthopedic applications such as monitoring limb movement and bone repair, neurophysiological applications such as monitoring electrical impulses, and any other tissue, organ, system, or condition that may benefit from improved sensor-enabled monitoring.

Wound Therapy

Some embodiments disclosed herein relate to wound therapy for a human or animal body. Therefore, any reference to a wound herein can refer to a wound on a human or animal body, and any reference to a body herein can refer to a human or animal body. The disclosed technology embodiments may relate to preventing or minimizing damage to physiological tissue or living tissue, or to the treatment of damaged tissue (for example, a wound as described herein) wound with or without reduced pressure, including for example a source of negative pressure and wound dressing components and apparatuses. The apparatuses and components comprising the wound overlay and packing materials or internal layers, if any, are sometimes collectively referred to herein as dressings. In some embodiments, the wound dressing can be provided to be utilized without reduced pressure.

Some embodiments disclosed herein relate to wound therapy for a human or animal body. Therefore, any reference to a wound herein can refer to a wound on a human or animal body, and any reference to a body herein can refer to a human or animal body. The disclosed technology embodiments may relate to preventing or minimizing damage to physiological tissue or living tissue, or to the treatment of damaged tissue (for example, a wound as described herein).

As used herein the expression "wound" may include an injury to living tissue may be caused by a cut, blow, or other impact, typically one in which the skin is cut or broken. A wound may be a chronic or acute injury. Acute wounds occur as a result of surgery or trauma. They move through the stages of healing within a predicted timeframe. Chronic wounds typically begin as acute wounds. The acute wound can become a chronic wound when it does not follow the healing stages resulting in a lengthened recovery. It is believed that the transition from acute to chronic wound can be due to a patient being immuno-compromised.

Chronic wounds may include for example: venous ulcers (such as those that occur in the legs), which account for the majority of chronic wounds and mostly affect the elderly, diabetic ulcers (for example, foot or ankle ulcers), peripheral arterial disease, pressure ulcers, or epidermolysis bullosa (EB).

Examples of other wounds include, but are not limited to, abdominal wounds or other large or incisional wounds, either as a result of surgery, trauma, sterniotomies, fasciotomies, or other conditions, dehisced wounds, acute wounds, chronic wounds, subacute and dehisced wounds, traumatic wounds, flaps and skin grafts, lacerations, abrasions, contusions, burns, diabetic ulcers, pressure ulcers, stoma, surgical wounds, trauma and venous ulcers or the like.

Wounds may also include a deep tissue injury. Deep tissue injury is a term proposed by the National Pressure Ulcer Advisory Panel (NPUAP) to describe a unique form of pressure ulcers. These ulcers have been described by clinicians for many years with terms such as purple pressure ulcers, ulcers that are likely to deteriorate and bruises on bony prominences.

Wound may also include tissue at risk of becoming a wound as discussed herein. For example, tissue at risk may include tissue over a bony protuberance (at risk of deep tissue injury/insult) or pre-surgical tissue (for example, knee tissue) that may has the potential to be cut (for example, for joint replacement/surgical alteration/reconstruction).

Some embodiments relate to methods of treating a wound with the technology disclosed herein in conjunction with one or more of the following: advanced footwear, turning a patient, offloading (such as, offloading diabetic foot ulcers), treatment of infection, systemix, antimicrobial, antibiotics, surgery, removal of tissue, affecting blood flow, physiotherapy, exercise, bathing, nutrition, hydration, nerve stimulation, ultrasound, electrostimulation, oxygen therapy, microwave therapy, active agents ozone, antibiotics, antimicrobials, or the like.

Alternatively or additionally, a wound may be treated using topical negative pressure and/or traditional advanced wound care, which is not aided by the using of applied negative pressure (may also be referred to as non-negative pressure therapy).

Advanced wound care may include use of an absorbent dressing, an occlusive dressing, use of an antimicrobial and/or debriding agents in a wound dressing or adjunct, a pad (for example, a cushioning or compressive therapy, such as stockings or bandages), or the like.

In some embodiments, treatment of such wounds can be performed using traditional wound care, wherein a dressing can be applied to the wound to facilitate and promote healing of the wound.

Some embodiments relate to methods of manufacturing a wound dressing comprising providing a wound dressing as disclosed herein.

The wound dressings that may be utilized in conjunction with the disclosed technology include any known dressing in the art. The technology is applicable to negative pressure therapy treatment as well as non-negative pressure therapy treatment.

In some embodiments, a wound dressing comprises one or more absorbent layer(s). The absorbent layer may be a foam or a superabsorbent.

In some embodiments, wound dressings may comprise a dressing layer including a polysaccharide or modified polysaccharide, a polyvinylpyrrolidone, a polyvinyl alcohol, a polyvinyl ether, a polyurethane, a polyacrylate, a polyacrylamide, collagen, or gelatin or mixtures thereof. Dressing layers comprising the polymers listed are known in the art as being useful for forming a wound dressing layer for either negative pressure therapy or non-negative pressure therapy.

In some embodiments, the polymer matrix may be a polysaccharide or modified polysaccharide.

In some embodiments, the polymer matrix may be a cellulose. Cellulose material may include hydrophilically modified cellulose such as methyl cellulose, carboxymethyl cellulose (CMC), carboxymethyl cellulose (CEC), ethyl cellulose, propyl cellulose, hydroxyethyl cellulose, hydroxypropyl cellulose, hydroxypropylmethyl cellulose, carboxyethyl sulphonate cellulose, cellulose alkyl sulphonate, or mixtures thereof.

In certain embodiments, cellulose material may be cellulose alkyl sulphonate. The alkyl moiety of the alkyl sulphonate substituent group may have an alkyl group having 1 to 6 carbon atoms, such as methyl, ethyl, propyl, or butyl. The alkyl moiety may be branched or unbranched, and hence suitable propyl sulphonate substituents may be 1- or 2-methyl-ethylsulphonate. Butyl sulphonate substituents may be 2-ethyl-ethylsulphonate, 2,2-dimethyl-ethylsulphonate, or 1,2-dimethyl-ethylsulphonate. The alkyl sulphonate substituent group may be ethyl sulphonate. The cellulose alkyl sulphonate is described in WO10061225, US2016/114074, US2006/0142560, or U.S. Pat. No. 5,703,225, the disclosures of which are hereby incorporated by reference in their entirety.

Cellulose alkyl sulfonates may have varying degrees of substitution, the chain length of the cellulose backbone structure, and the structure of the alkyl sulfonate substituent. Solubility and absorbency are largely dependent on the degree of substitution: as the degree of substitution is increased, the cellulose alkyl sulfonate becomes increasingly soluble. It follows that, as solubility increases, absorbency increases.

In some embodiments, a wound dressing also comprises a top or cover layer.

The thickness of the wound dressing disclosed herein may be between 1 to 20, or 2 to 10, or 3 to 7 mm.

In some embodiments, the disclosed technology may be used in conjunction with a non-negative pressure dressing.

A non-negative pressure wound dressing suitable for providing protection at a wound site may comprise:
an absorbent layer for absorbing wound exudate and
an obscuring element for at least partially obscuring a view of wound exudate absorbed by the absorbent layer in use.

The obscuring element may be partially translucent.

The obscuring element may be a masking layer.

The non-negative pressure wound dressing may further comprise a region in or adjacent the obscuring element for allowing viewing of the absorbent layer. For example, the obscuring element layer may be provided over a central region of the absorbent layer and not over a border region of the absorbent layer. In some embodiments, the obscuring element is of hydrophilic material or is coated with a hydrophilic material.

The obscuring element may comprise a three-dimensional knitted spacer fabric. The spacer fabric is known in the art and may include a knitted spacer fabric layer.

The obscuring element may further comprise an indicator for indicating the need to change the dressing.

In some embodiments, the obscuring element is provided as a layer at least partially over the absorbent layer, further from a wound site than the absorbent layer in use.

The non-negative pressure wound dressing may further comprise a plurality of openings in the obscuring element for allowing fluid to move therethrough. The obscuring element may comprise, or may be coated with, a material having size-exclusion properties for selectively permitting or preventing passage of molecules of a predetermined size or weight.

The obscuring element may be configured to at least partially mask light radiation having wavelength of 600 nm and less.

The obscuring element may be configured to reduce light absorption by 50% or more.

The obscuring element may be configured to yield a CIE L* value of 50 or more, and optionally 70 or more. In some embodiments, the obscuring element may be configured to yield a CIE L* value of 70 or more.

In some embodiments, the non-negative pressure wound dressing may further comprise at least one of a wound contact layer, a foam layer, an odor control element, a pressure-resistant layer and a cover layer.

In some embodiments, the cover layer is present, and the cover layer is a translucent film Typically, the translucent film has a moisture vapour permeability of 500 g/m2/24 hours or more.

The translucent film may be a bacterial barrier.

In some embodiments, the non-negative pressure wound dressing as disclosed herein comprises the wound contact layer and the absorbent layer overlies the wound contact layer. The wound contact layer carries an adhesive portion for forming a substantially fluid tight seal over the wound site.

The non-negative pressure wound dressing as disclosed herein may comprise the obscuring element and the absorbent layer being provided as a single layer.

In some embodiments, the non-negative pressure wound dressing disclosed herein comprises the foam layer, and the obscuring element is of a material comprising components that may be displaced or broken by movement of the obscuring element.

In some embodiments, the non-negative pressure wound dressing comprises an odor control element, and in another embodiment the dressing does not include an odor control element. When present, the odor control element may be dispersed within or adjacent the absorbent layer or the obscuring element. Alternatively, when present the odor control element may be provided as a layer sandwiched between the foam layer and the absorbent layer.

In some embodiments, the disclosed technology for a non-negative pressure wound dressing comprises a method of manufacturing a wound dressing, comprising: providing an absorbent layer for absorbing wound exudate; and providing an obscuring element for at least partially obscuring a view of wound exudate absorbed by the absorbent layer in use.

In some embodiments, the non-negative pressure wound dressing is may be suitable for providing protection at a wound site, comprising: an absorbent layer for absorbing wound exudate; and a shielding layer provided over the absorbent layer, and further from a wound-facing side of the wound dressing than the absorbent layer. The shielding layer may be provided directly over the absorbent layer. In some embodiments, the shielding layer comprises a three-dimensional spacer fabric layer.

The shielding layer increases the area over which a pressure applied to the dressing is transferred by 25% or more or the initial area of application. For example the shielding layer increases the area over which a pressure applied to the dressing is transferred by 50% or more, and optionally by 100% or more, and optionally by 200% or more.

The shielding layer may comprise 2 or more sub-layers, wherein a first sub-layer comprises through holes and a further sub-layer comprises through holes and the through holes of the first sub-layer are offset from the through holes of the further sub-layer.

The non-negative pressure wound dressing as disclosed herein may further comprise a permeable cover layer for allowing the transmission of gas and vapour therethrough, the cover layer provided over the shielding layer, wherein through holes of the cover layer are offset from through holes of the shielding layer.

The non-negative pressure wound dressing may be suitable for treatment of pressure ulcers.

A more detailed description of the non-negative pressure dressing disclosed hereinabove is provided in WO2013007973, the entirety of which is hereby incorporated by reference.

In some embodiments, the non-negative pressure wound dressing may be a multi-layered wound dressing comprising: a fibrous absorbent layer for absorbing exudate from a wound site; and a support layer configured to reduce shrinkage of at least a portion of the wound dressing.

In some embodiments, the multi-layered wound dressing disclosed herein, further comprises a liquid impermeable film layer, wherein the support layer is located between the absorbent layer and the film layer.

The support layer disclosed herein may comprise a net. The net may comprise a geometric structure having a plurality of substantially geometric apertures extending therethrough. The geometric structure may for example comprise a plurality of bosses substantially evenly spaced and joined by polymer strands to form the substantially geometric apertures between the polymer strands.

The net may be formed from high density polyethylene.
The apertures may have an area from 0.005 to 0.32 mm2.
The support layer may have a tensile strength from 0.05 to 0.06 Nm.
The support layer may have a thickness of from 50 to 150 µm.

In some embodiments, the support layer is located directly adjacent the absorbent layer. Typically, the support layer is bonded to fibers in a top surface of the absorbent layer. The support layer may further comprise a bonding layer, wherein the support layer is heat laminated to the fibers in the absorbent layer via the bonding layer. The bonding layer may comprise a low melting point adhesive such as ethylene-vinyl acetate adhesive.

In some embodiments, the multi-layered wound dressing disclosed herein further comprises an adhesive layer attaching the film layer to the support layer.

In some embodiments, the multi-layered wound dressing disclosed herein further comprises a wound contact layer located adjacent the absorbent layer for positioning adjacent a wound. The multi-layered wound dressing may further comprise a fluid transport layer between the wound contact layer and the absorbent layer for transporting exudate away from a wound into the absorbent layer.

A more detailed description of the multi-layered wound dressing disclosed hereinabove is provided in GB patent application filed on 28 Oct. 2016 with application number GB1618298.2, the entirety of which is hereby incorporated by reference.

In some embodiments, the disclosed technology may be incorporated in a wound dressing comprising a vertically lapped material comprising: a first layer of an absorbing layer of material, and a second layer of material, wherein the first layer being constructed from at least one layer of non-woven textile fibers, the non-woven textile fibers being folded into a plurality of folds to form a pleated structure. In some embodiments, the wound dressing further comprises a second layer of material that is temporarily or permanently connected to the first layer of material.

Typically the vertically lapped material has been slitted.

In some embodiments, the first layer has a pleated structure having a depth determined by the depth of pleats or by the slitting width. The first layer of material may be a moldable, lightweight, fiber-based material, blend of material or composition layer.

The first layer of material may comprise one or more of manufactured fibers from synthetic, natural or inorganic polymers, natural fibers of a cellulosic, proteinaceous or mineral source.

The wound dressing may comprise two or more layers of the absorbing layer of material vertically lapped material stacked one on top of the other, wherein the two or more layers have the same or different densities or composition.

The wound dressing may in some embodiments comprise only one layer of the absorbing layer of material vertically lapped material.

The absorbing layer of material is a blend of natural or synthetic, organic or inorganic fibers, and binder fibers, or bicomponent fibers typically PET with a low melt temperature PET coating to soften at specified temperatures and to act as a bonding agent in the overall blend.

In some embodiments, the absorbing layer of material may be a blend of 5 to 95% thermoplastic polymer, and 5 to 95 wt % of a cellulose or derivative thereof.

In some embodiments, the wound dressing disclosed herein has a second layer comprises a foam or a dressing fixative.

The foam may be a polyurethane foam. The polyurethane foam may have an open or closed pore structure.

The dressing fixative may include bandages, tape, gauze, or backing layer.

In some embodiments, the wound dressing as disclosed herein comprises the absorbing layer of material connected directly to a second layer by lamination or by an adhesive, and the second layer is connected to a dressing fixative layer. The adhesive may be an acrylic adhesive, or a silicone adhesive.

In some embodiments, the wound dressing as disclosed herein further comprises layer of a superabsorbent fiber, or a viscose fiber or a polyester fiber.

In some embodiments, the wound dressing as disclosed herein further comprises a backing layer. The backing layer may be a transparent or opaque film. Typically the backing layer comprises a polyurethane film (typically a transparent polyurethane film).

A more detailed description of the multi-layered wound dressing disclosed hereinabove is provided in GB patent applications filed on 12 Dec. 2016 with application number GB1621057.7; and 22 Jun. 2017 with application number GB1709987.0, the entirety of each of which is hereby incorporated by reference.

In some embodiments, the non-negative pressure wound dressing may comprise an absorbent component for a wound dressing, the component comprising a wound contacting layer comprising gel forming fibers bound to a foam layer, wherein the foam layer is bound directly to the wound contact layer by an adhesive, polymer based melt layer, by flame lamination or by ultrasound.

The absorbent component may be in a sheet form.

The wound contacting layer may comprise a layer of woven or non-woven or knitted gel forming fibers.

The foam layer may be an open cell foam, or closed cell foam, typically an open cell foam. The foam layer is a hydrophilic foam.

The wound dressing may comprise the component that forms an island in direct contact with the wound surrounded by periphery of adhesive that adheres the dressing to the wound. The adhesive may be a silicone or acrylic adhesive, typically a silicone adhesive.

The wound dressing may be covered by a film layer on the surface of the dressing furthest from the wound.

A more detailed description of the wound dressing of this type hereinabove is provided in EP2498829, the entirety of which is hereby incorporated by reference.

In some embodiments, the non-negative pressure wound dressing may comprise a multi layered wound dressing for use on wounds producing high levels of exudate, characterized in that the dressing comprising: a transmission layer having an MVTR of at least 300 gm2/24 hours, an absorbent core comprising gel forming fibers capable of absorbing and retaining exudate, a wound contacting layer comprising gel forming fibers which transmits exudate to the absorbent core and a keying layer positioned on the absorbent core, the absorbent core and wound contacting layer limiting the lateral spread of exudate in the dressing to the region of the wound.

The wound dressing may be capable of handling at least 6 g (or 8 g and 15 g) of fluid per 10 cm2 of dressing in 24 hours.

The wound dressing may comprise gel forming fibers that are chemically modified cellulosic fibers in the form of a fabric. The fibers may include carboxymethylated cellulose fibers, typically sodium carboxymethylcellulose fiber.

The wound dressing may comprise a wound contact layer with a lateral wicking rate from 5 mm per minute to 40 mm per minute. The wound contact layer may have a fiber density between 25 gm2 and 55 gm2, such as 35 gm2.

The absorbent core may have an absorbency of exudate of at least 10 g/g, and typically a rate of lateral wicking of less the 20 mm per minute.

The absorbent core may have a blend in the range of up to 25% cellulosic fibers by weight and 75% to 100% gel forming fibers by weight.

Alternatively, the absorbent core may have a blend in the range of up to 50% cellulosic fibers by weight and 50% to 100% gel forming fibers by weight. For example the blend is in the range of 50% cellulosic fibers by weight and 50% gel forming fibers by weight.

The fiber density in the absorbent core may be between 150 gm2 and 250 gm2, or about 200 gm2.

The wound dressing when wet may have shrinkage that is less than 25% or less than 15% of its original size/dimension.

The wound dressing may comprise a transmission layer and the layer is a foam. The transmission layer may be a polyurethane foam laminated to a polyurethane film.

The wound dressing may comprise one or more layers selected from the group comprising a soluble medicated film layer; an odor-absorbing layer; a spreading layer and an additional adhesive layer.

The wound dressing may be 2 mm and 4 mm thick.

The wound dressing may be characterized in that the keying layer bonds the absorbent core to a neighboring layer. In some embodiments, the keying layer may be positioned on either the wound facing side of the absorbent core or the non-wound facing side of the absorbent core. In some embodiments, the keying layer is positioned between the absorbent core and the wound contact layer. The keying layer is a polyamide web.

A more detailed description of the wound dressing of this type hereinabove is provided in EP1718257, the entirety of which is hereby incorporated by reference.

In some embodiments, the non-negative pressure wound dressing may be a compression bandage. Compression bandages are known for use in the treatment of oedema and other venous and lymphatic disorders, e.g., of the lower limbs.

A compression bandage systems typically employ multiple layers including a padding layer between the skin and the compression layer or layers. The compression bandage may be useful for wounds such as handling venous leg ulcers.

The compression bandage in some embodiments may comprise a bandage system comprising an inner skin facing layer and an elastic outer layer, the inner layer comprising a first ply of foam and a second ply of an absorbent nonwoven web, the inner layer and outer layer being sufficiently elongated so as to be capable of being wound about a patient's limb. A compression bandage of this type is disclosed in WO99/58090, the entirety of which is hereby incorporated by reference.

In some embodiments, the compression bandage system comprises: a) an inner skin facing, elongated, elastic bandage comprising: (i) an elongated, elastic substrate, and (ii) an elongated layer of foam, said foam layer being affixed to a face of said substrate and extending 33% or more across said face of substrate in transverse direction and 67% or more across said face of substrate in longitudinal direction; and b) an outer, elongated, self-adhering elastic bandage; said bandage having a compressive force when extended; wherein, in use, said foam layer of the inner bandage faces the skin and the outer bandage overlies the inner bandage. A compression bandage of this type is disclosed in WO2006/110527, the entirety of which is hereby incorporated by reference.

In some embodiments other compression bandage systems such as those disclosed in U.S. Pat. No. 6,759,566 and US 2002/0099318, the entirety of each of which is hereby incorporated by reference.

Negative Pressure Wound Dressing

In some embodiments, treatment of such wounds can be performed using negative pressure wound therapy, wherein a reduced or negative pressure can be applied to the wound to facilitate and promote healing of the wound. It will also be appreciated that the wound dressing and methods as disclosed herein may be applied to other parts of the body, and are not necessarily limited to treatment of wounds.

It will be understood that embodiments of the present disclosure are generally applicable to use in topical negative pressure ("TNP") therapy systems. Briefly, negative pressure wound therapy assists in the closure and healing of many forms of "hard to heal" wounds by reducing tissue oedema; encouraging blood flow and granular tissue formation; removing excess exudate and may reduce bacterial load (and thus infection risk). In addition, the therapy allows for less disturbance of a wound leading to more rapid healing. TNP therapy systems may also assist on the healing of surgically closed wounds by removing fluid and by helping to stabilize the tissue in the apposed position of closure. A further beneficial use of TNP therapy can be found in grafts and flaps where removal of excess fluid is important and close proximity of the graft to tissue is required in order to ensure tissue viability.

Negative pressure therapy can be used for the treatment of open or chronic wounds that are too large to spontaneously close or otherwise fail to heal by means of applying negative pressure to the site of the wound. Topical negative pressure (TNP) therapy or negative pressure wound therapy (NPWT) involves placing a cover that is impermeable or semi-permeable to fluids over the wound, using various means to seal the cover to the tissue of the patient surrounding the wound, and connecting a source of negative pressure (such as a vacuum pump) to the cover in a manner so that negative pressure is created and maintained under the cover. It is believed that such negative pressures promote wound healing by facilitating the formation of granulation tissue at the wound site and assisting the body's normal inflammatory process while simultaneously removing excess fluid, which may contain adverse cytokines or bacteria.

Some of the dressings used in NPWT can include many different types of materials and layers, for example, gauze, pads, foam pads or multi-layer wound dressings. One example of a multi-layer wound dressing is the PICO dressing, available from Smith & Nephew, includes a wound contact layer and a superabsorbent layer beneath a backing layer to provide a canister-less system for treating a wound with NPWT. The wound dressing may be sealed to a suction port providing connection to a length of tubing, which may be used to pump fluid out of the dressing or to transmit negative pressure from a pump to the wound dressing. Additionally, RENASYS-F, RENASYS-G, RENASYS-AB, and RENASYS-F/AB, available from Smith & Nephew, are additional examples of NPWT wound dressings and systems. Another example of a multi-layer wound dressing is the ALLEVYN Life dressing, available from Smith & Nephew, which includes a moist wound environment dressing that is used to treat the wound without the use of negative pressure.

As is used herein, reduced or negative pressure levels, such as −X mmHg, represent pressure levels relative to normal ambient atmospheric pressure, which can correspond to 760 mmHg (or 1 atm, 29.93 inHg, 101.325 kPa, 14.696 psi, etc.). Accordingly, a negative pressure value of −X mmHg reflects absolute pressure that is X mmHg below 760 mmHg or, in other words, an absolute pressure of (760-X) mmHg. In addition, negative pressure that is "less" or "smaller" than X mmHg corresponds to pressure that is closer to atmospheric pressure (such as, −40 mmHg is less than −60 mmHg). Negative pressure that is "more" or "greater" than −X mmHg corresponds to pressure that is further from atmospheric pressure (such as, −80 mmHg is more than −60 mmHg). In some embodiments, local ambient atmospheric pressure is used as a reference point, and such local atmospheric pressure may not necessarily be, for example, 760 mmHg.

The negative pressure range for some embodiments of the present disclosure can be approximately −80 mmHg, or between about −20 mmHg and −200 mmHg Note that these pressures are relative to normal ambient atmospheric pressure, which can be 760 mmHg Thus, −200 mmHg would be about 560 mmHg in practical terms. In some embodiments, the pressure range can be between about −40 mmHg and −150 mmHg. Alternatively a pressure range of up to −75 mmHg, up to −80 mmHg or over −80 mmHg can be used. Also in other embodiments a pressure range of below −75 mmHg can be used. Alternatively, a pressure range of over approximately −100 mmHg, or even −150 mmHg, can be supplied by the negative pressure apparatus.

In some embodiments of wound closure devices described herein, increased wound contraction can lead to increased tissue expansion in the surrounding wound tissue. This effect may be increased by varying the force applied to the tissue, for example by varying the negative pressure applied to the wound over time, possibly in conjunction with increased tensile forces applied to the wound via embodiments of the wound closure devices. In some embodiments, negative pressure may be varied over time for example using a sinusoidal wave, square wave, or in synchronization with one or more patient physiological indices (such as, heartbeat). Examples of such applications where additional disclosure relating to the preceding may be found include U.S. Pat. No. 8,235,955, titled "Wound treatment apparatus and method," issued on Aug. 7, 2012; and U.S. Pat. No. 7,753,894, titled "Wound cleansing apparatus with stress," issued Jul. 13, 2010. The disclosures of both of these patents are hereby incorporated by reference in their entirety.

Embodiments of the wound dressings, wound dressing components, wound treatment apparatuses and methods described herein may also be used in combination or in addition to those described in International Application No. PCT/IB2013/001469, filed May 22, 2013, published as WO 2013/175306 A2 on Nov. 28, 2013, titled "APPARATUSES AND METHODS FOR NEGATIVE PRESSURE WOUND THERAPY," U.S. patent application Ser. No. 14/418,908, filed Jan. 30, 2015, published as US 2015/0190286 A1 on Jul. 9, 2015, titled "WOUND DRESSING AND METHOD OF TREATMENT," the disclosures of which are hereby incorporated by reference in their entireties. Embodiments of the wound dressings, wound dressing components, wound treatment apparatuses and methods described herein may also be used in combination or in addition to those described in U.S. patent application Ser. No. 13/092,042, filed Apr. 21, 2011, published as US2011/0282309, titled "WOUND DRESSING AND METHOD OF USE," and U.S. patent application Ser. No. 14/715,527, filed May 18, 2015, published as US2016/0339158 A1 on Nov. 24, 2016, titled "FLUIDIC CONNECTOR FOR NEGATIVE PRESSURE WOUND THERAPY," the disclosure of each of which is hereby incorporated by reference in its entirety, including further details relating to embodiments of wound dressings, the wound dressing components and principles, and the materials used for the wound dressings.

Additionally, some embodiments related to TNP wound treatment comprising a wound dressing in combination with a pump or associated electronics described herein may also be used in combination or in addition to those described in International Application PCT/EP2016/059329 filed Apr. 26, 2016, published as WO 2016/174048 on Nov. 3, 2016, entitled "REDUCED PRESSURE APPARATUS AND METHODS," the disclosure of which is hereby incorporated by reference in its entirety.

In some embodiments of wound closure devices described herein, increased wound contraction can lead to increased tissue expansion in the surrounding wound tissue. This effect may be increased by varying the force applied to the tissue, for example by varying the negative pressure applied to the wound over time, possibly in conjunction with increased tensile forces applied to the wound via embodiments of the wound closure devices. Further, there may be additional effects on tissues in close proximity to the filler, for example, the tissue is under compression due to the reactive force of the elastic filler pressing on the tissue. Such compression may result in local hypoxia due to occlusion of the blood vessels. In the wider peripheral tissue, this expansion may lead to blood vessel expansion. Further details are provided in "NPWT settings and dressing choices made easy" by Malmsjo and Borgquist, published in Wounds International in May 2010, hereby incorporated by reference in its entirety. For example, in a wound that is not at risk for ischemia, the increased and decreased blood flow caused by pressure from the wound dressing is likely advantageous for wound healing. The increase in blood flow may improve oxygen and nutrient supply to the tissue, and improve penetration of antibiotics and the removal of waste. Additionally, the reduction in blood flow may stimulate angiogenesis, thereby promoting granulation tissue formation.

Wound Healing

One of skill in the art will understand that the embodiments described herein, particularly with reference to Eulerian Video Magnification (EVM), are not merely applicable to situations involving NPWT. Rather, such embodiments may be broadly applicable to situations that do not necessarily require NPWT, such as evaluating intact tissue or providing additional treatments to wounds.

Wounds may be generally categorized as open or closed, often depending upong how the wound is caused. As described above, the techniques may be applied to both open and to closed wounds, depending on the particulars of the embodiment. Open wounds may be caused by a variety of events, including: incisions, lacerations, abrasions, punctures, penetration, amputation, and other means. Closed wounds may be caused by damage to a blood vessel resulting in formation of a hematoma, and/or by internal injuries caused by crushing. Further, wounds may involve various layers of tissue, for example, shallower wounds may only involve the topmost layers of the skin, while deeper wounds may involve underlying subcutaneous tissue layers such as the hypodermis, including underlying connective tissues and fatty layers. In certain embodiments, wounds may even encompass underlying internal organs, deep beneath the skin. Certain wounds, such as those caused by pressure injuries, may start to occur within the deeper tissue layers without become evident on the surface of the skin until much later.

In addition to NPWT treatments described above, wounds may be treated by a wide variety of techniques and materials. For example, wounds may be treated by debridement to remove dead and/or necrotic tissue. Wounds may be treated with a with various type of dressings, including dry and wet dressings, chemically-impregnated dressings, foam dressing, hydrogel dressings, hydrocolloid dressings, film dressings, and other suitable dressings. Wounds may further be treated with bioactive molecules such as antimicrobials, growth factors, anti-inflammatories, analgesics and other suitable treatments. Such treatments may be incorporated into the aforementioned dressings.

Further details regarding wounds and wound treatment, in particular wounds caused by pressure injuries may be found in the article "Pressure Injuries (Pressure Ulcers) and Wound Care" by Kirman et al, published in Medscape March 2017, and hereby incorporated by reference in its entirety. For example, the most common candidates for pressure ulcers include: elderly persons, persons who are chronically ill (such as those with cancer, stroke, or diabetes), persons who are immobile (e.g, as a consequence of fracture, arthritis, or pain), persons who are weak or debilitated, patients with altered mental status (e.g., from the effects of narcotics, anesthesia, or coma), and/or persons with decreased sensation or paralysis. Potential secondary factors include: illness or debilitation that increases pressure ulcer formation, fever (increases metabolic demands), predisposing ischemia, diaphoresis which promotes skin maceration, incontinence which causes skin irritation and contamination, edema, jaundice, pruritus, and xerosis (dry skin). Additionally, prevention of pressure ulcer injuries may include: scheduled body turning, appropriate bed positioning, protection of bony prominences, skin care, control of spascity and prevention of contractures, use of support surfaces/specialty beds, nutritional support, and maintenance of current levels of activity, mobility and range of motion.

Negative Pressure System

FIG. 1 illustrates an embodiment of a negative or reduced pressure wound treatment (or TNP) system 100 comprising a wound filler 130 placed inside a wound cavity 110, the wound cavity sealed by a wound cover 120. The wound filler 130 in combination with the wound cover 120 can be referred to as wound dressing. A single or multi lumen tube or conduit 140 is connected the wound cover 120 with a pump assembly 150 configured to supply reduced pressure. The wound cover 120 can be in fluidic communication with the wound cavity 110. In any of the system embodiments disclosed herein, as in the embodiment illustrated in FIG. 1, the pump assembly can be a canisterless pump assembly (meaning that exudate is collected in the wound dressing or is transferred via tube 140 for collection to another location). However, any of the pump assembly embodiments disclosed herein can be configured to include or support a canister. Additionally, in any of the system embodiments disclosed herein, any of the pump assembly embodiments can be mounted to or supported by the dressing, or adjacent to the dressing.

The wound filler 130 can be any suitable type, such as hydrophilic or hydrophobic foam, gauze, inflatable bag, and so on. The wound filler 130 can be conformable to the wound cavity 110 such that it substantially fills the cavity. The wound cover 120 can provide a substantially fluid impermeable seal over the wound cavity 110. The wound cover 120 can have a top side and a bottom side, and the bottom side adhesively (or in any other suitable manner) seals with wound cavity 110. The conduit 140 or lumen or any other conduit or lumen disclosed herein can be formed from polyurethane, PVC, nylon, polyethylene, silicone, or any other suitable material.

Some embodiments of the wound cover 120 can have a port (not shown) configured to receive an end of the conduit 140. For example, the port can be Renays Soft Port available from Smith & Nephew. In other embodiments, the conduit 140 can otherwise pass through or under the wound cover 120 to supply reduced pressure to the wound cavity 110 so as to maintain a target or desired level of reduced pressure in the wound cavity. The conduit 140 can be any suitable article configured to provide at least a substantially sealed fluid flow pathway between the pump assembly 150 and the wound cover 120, so as to supply the reduced pressure provided by the pump assembly 150 to wound cavity 110.

The wound cover 120 and the wound filler 130 can be provided as a single article or an integrated single unit. In some embodiments, no wound filler is provided and the wound cover by itself may be considered the wound dressing. The wound dressing may then be connected, via the conduit 140, to a source of negative pressure, such as the pump assembly 150. The pump assembly 150 can be miniaturized and portable, although larger conventional pumps such can also be used.

The wound cover 120 can be located over a wound site to be treated. The wound cover 120 can form a substantially sealed cavity or enclosure over the wound site. In some embodiments, the wound cover 120 can be configured to have a film having a high water vapor permeability to enable the evaporation of surplus fluid, and can have a superabsorbing material contained therein to safely absorb wound exudate. It will be appreciated that throughout this specification reference is made to a wound. In this sense it is to be understood that the term wound is to be broadly construed and encompasses open and closed wounds in which skin is torn, cut or punctured or where trauma causes a contusion, or any other surficial or other conditions or imperfections on the skin of a patient or otherwise that benefit from reduced pressure treatment. A wound is thus broadly defined as any damaged region of tissue where fluid may or may not be produced. Examples of such wounds include, but are not limited to, acute wounds, chronic wounds, surgical incisions and other incisions, subacute and dehisced wounds, traumatic wounds, flaps and skin grafts, lacerations, abrasions, contusions, burns, diabetic ulcers, pressure ulcers, stoma, surgical wounds, trauma and venous ulcers or the like. The components of the TNP system described herein can be particularly suited for incisional wounds that exude a small amount of wound exudate.

Some embodiments of the system are designed to operate without the use of an exudate canister. Some embodiments can be configured to support an exudate canister. In some embodiments, configuring the pump assembly 150 and tubing 140 so that the tubing 140 can be quickly and easily removed from the pump assembly 150 can facilitate or improve the process of dressing or pump changes, if necessary. Any of the pump embodiments disclosed herein can be configured to have any suitable connection between the tubing and the pump.

The pump assembly 150 can be configured to deliver negative pressure of approximately −80 mmHg, or between about −20 mmHg and 200 mmHg in some implementations. Note that these pressures are relative to normal ambient atmospheric pressure thus, −200 mmHg would be about 560 mmHg in practical terms. The pressure range can be between about −40 mmHg and −150 mmHg. Alternatively a pressure range of up to −75 mmHg, up to −80 mmHg or over −80 mmHg can be used. Also a pressure range of below −75 mmHg can be used. Alternatively a pressure range of over approximately −100 mmHg, or even 150 mmHg, can be supplied by the pump assembly 150.

In operation, the wound filler 130 is inserted into the wound cavity 110 and wound cover 120 is placed so as to seal the wound cavity 110. The pump assembly 150 provides a source of a negative pressure to the wound cover 120, which is transmitted to the wound cavity 110 via the wound filler 130. Fluid (e.g., wound exudate) is drawn through the conduit 140, and can be stored in a canister. In some embodiments, fluid is absorbed by the wound filler 130 or one or more absorbent layers (not shown).

Wound dressings that may be utilized with the pump assembly and other embodiments of the present application include Renasys-F, Renasys-G, Renasys AB, and Pico Dressings available from Smith & Nephew. Further description of such wound dressings and other components of a negative pressure wound therapy system that may be used with the pump assembly and other embodiments of the present application are found in U.S. Patent Publication Nos. 2011/0213287, 2011/0282309, 2012/0116334, 2012/0136325, and 2013/0110058, which are incorporated by reference in their entirety. In other embodiments, other suitable wound dressings can be utilized.

Pump Assembly and Canister

Figure 2A:
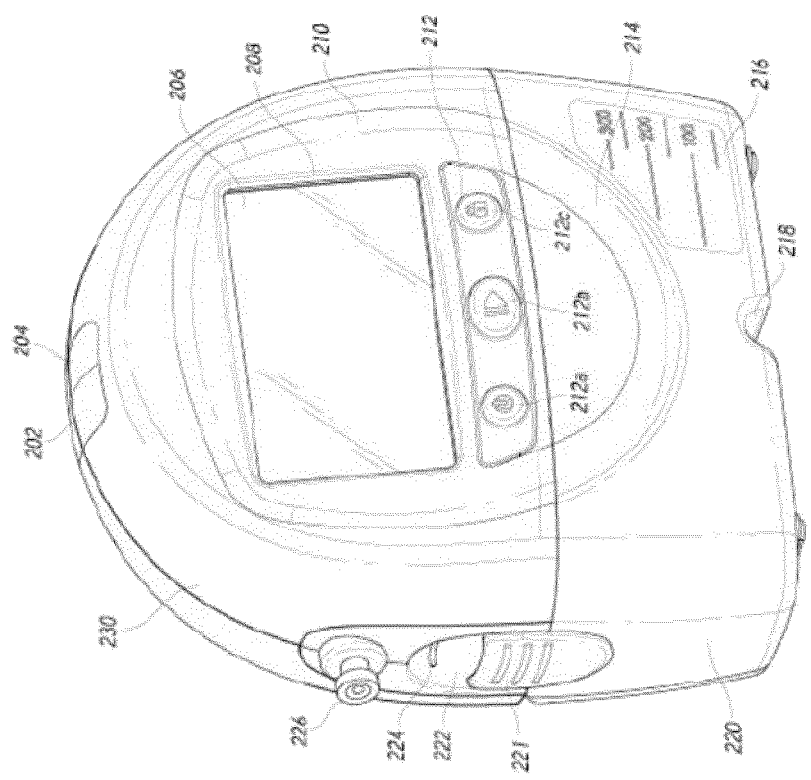
FIGS. 2A, 2B, and 2C illustrate a pump assembly and canister according to some embodiments.

FIG. 2A illustrates a front view of a pump assembly 230 and canister 220 according to some embodiments. As is illustrated, the pump assembly 230 and the canister are connected, thereby forming a negative pressure wound therapy device. The pump assembly 230 can be similar to or the same as the pump assembly 150 in some embodiments.

The pump assembly 230 includes one or more indicators, such as visual indicator 202 configured to indicate alarms and visual indicator 204 configured to indicate status of the TNP system. The indicators 202 and 204 can be configured to alert a user, such as patient or medical care provider, to a variety of operating or failure conditions of the system, including alerting the user to normal or proper operating conditions, pump failure, power supplied to the pump or power failure, detection of a leak within the wound cover or flow pathway, suction blockage, or any other similar or suitable conditions or combinations thereof. The pump assembly 230 can comprise additional indicators. The pump assembly can use a single indicator or multiple indicators. Any suitable indicator can be used such as visual, audio, tactile indicator, and so on. The indicator 202 can be configured to signal alarm conditions, such as canister full, power low, conduit 140 disconnected, seal broken in the wound seal 120, and so on. The indicator 202 can be configured to display red flashing light to draw user's attention. The indicator 204 can be configured to signal status of the TNP system, such as therapy delivery is ok, leak detected, and so on. The indicator 204 can be configured to display one or more different colors of light, such as green, yellow, etc. For example, green light can be emitted when the TNP system is operating properly and yellow light can be emitted to indicate a warning.

The pump assembly 230 includes a display or screen 206 mounted in a recess 208 formed in a case of the pump assembly. The display 206 can be a touch screen display. The display 206 can support playback of audiovisual (AV) content, such as instructional videos. As explained below, the display 206 can be configured to render a number of screens or graphical user interfaces (GUIs) for configuring, controlling, and monitoring the operation of the TNP system. The pump assembly 230 comprises a gripping portion 210 formed in the case of the pump assembly. The gripping portion 210 can be configured to assist the user to hold the pump assembly 230, such as during removal of the canister 220. The canister 220 can be replaced with another canister, such as when the canister 220 has been filled with fluid.

The pump assembly 230 includes one or more keys or buttons configured to allow the user to operate and monitor the operation of the TNP system. As is illustrated, there buttons 212a, 212b, and 212c (collectively referred to as buttons 212) are included. Button 212a can be configured as a power button to turn on/off the pump assembly 230. Button 212b can be configured as a play/pause button for the delivery of negative pressure therapy. For example, pressing the button 212b can cause therapy to start, and pressing the button 212b afterward can cause therapy to pause or end. Button 212c can be configured to lock the display 206 or the buttons 212. For instance, button 212c can be pressed so that the user does not unintentionally alter the delivery of the therapy. Button 212c can be depressed to unlock the controls. In other embodiments, additional buttons can be used or one or more of the illustrated buttons 212a, 212b, or 212c can be omitted. Multiple key presses or sequences of key presses can be used to operate the pump assembly 230.

The pump assembly 230 includes one or more latch recesses 222 formed in the cover. In the illustrated embodiment, two latch recesses 222 can be formed on the sides of the pump assembly 230. The latch recesses 222 can be configured to allow attachment and detachment of the canister 220 using one or more canister latches 221. The pump assembly 230 comprises an air outlet 224 for allowing air removed from the wound cavity 110 to escape. Air entering the pump assembly can be passed through one or more suitable filters, such as antibacterial filters. This can maintain reusability of the pump assembly. The pump assembly 230 includes one or more strap mounts 226 for connecting a carry strap to the pump assembly 230 or for attaching a cradle. In the illustrated embodiment, two strap mounts 226 can be formed on the sides of the pump assembly 230. In some embodiments, various of these features are omitted or various additional features are added to the pump assembly 230.

The canister 220 is configured to hold fluid (e.g., exudate) removed from the wound cavity 110. The canister 220 includes one or more latches 221 for attaching the canister to the pump assembly 230. In the illustrated embodiment, the canister 220 comprises two latches 221 on the sides of the canister. The exterior of the canister 220 can formed from frosted plastic so that the canister is substantially opaque and the contents of the canister and substantially hidden from plain view. The canister 220 comprises a gripping portion 214 formed in a case of the canister. The gripping portion 214 can be configured to allow the user to hold the pump assembly 220, such as during removal of the canister from the apparatus 230. The canister 220 includes a substantially transparent window 216, which can also include graduations of volume. For example, the illustrated 300 mL canister 220 includes graduations of 50 mL, 100 mL, 150 mL, 200 mL, 250 mL, and 300 mL. Other embodiments of the canister can hold different volume of fluid and can include different graduation scale. For example, the canister can be an 800 mL canister. The canister 220 comprises a tubing channel 218 for connecting to the conduit 140. In some embodiments, various of these features, such as the gripping portion 214, are omitted or various additional features are added to the canister 220. Any of the disclosed canisters may include or may omit a solidifier.

Figure 2B:
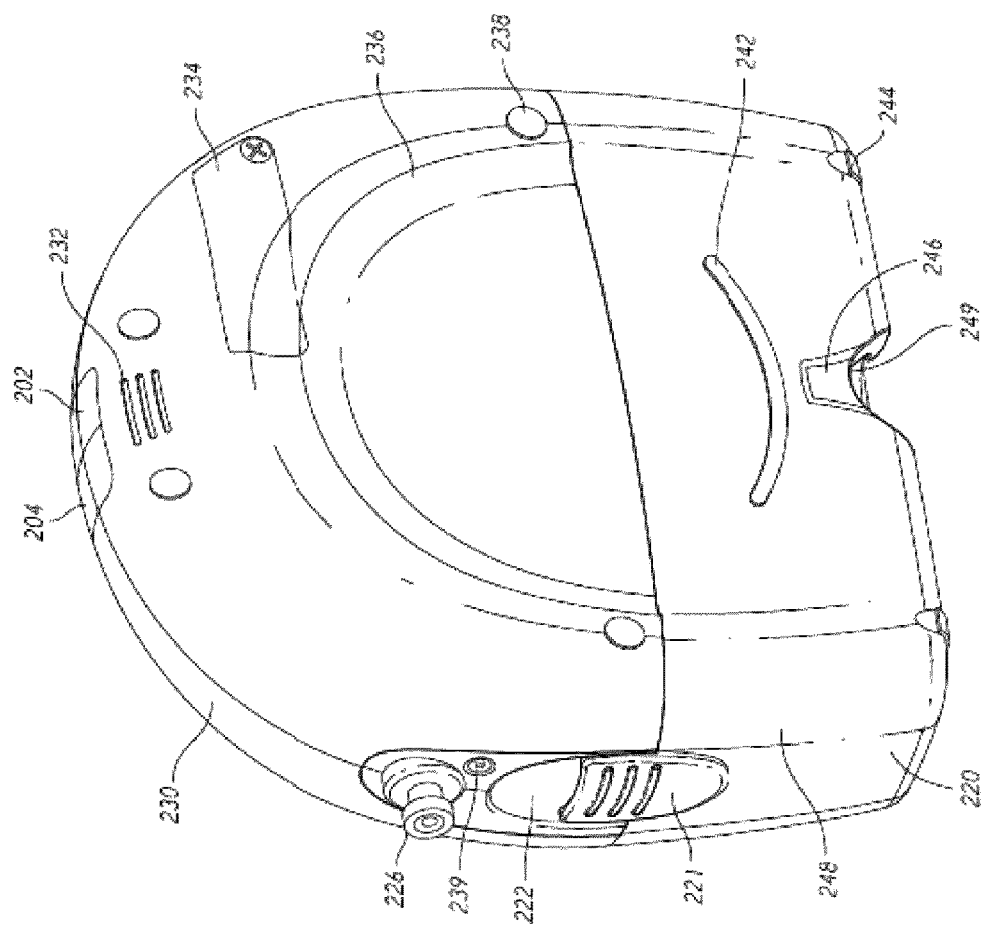

FIG. 2B illustrates a rear view of the pump assembly 230 and canister 220 according to some embodiments. The pump assembly 230 comprises a speaker port 232 for producing sound. The pump assembly 230 includes a filter access door 234 with a screw for removing the access door 234, accessing, and replacing one or more filters, such as antibacterial or odor filters. The pump assembly 230 comprises a gripping portion 236 formed in the case of the pump assembly. The gripping portion 236 can be configured to allow the user to hold the pump assembly 230, such as during removal of the canister 220. The pump assembly 230 includes one or more covers 238 configured to as screw covers or feet or protectors for placing the pump assembly 230 on a surface. The covers 230 can be formed out of rubber, silicone, or any other suitable material. The pump assembly 230 comprises a power jack 239 for charging and recharging an internal battery of the pump assembly. The power jack 239 can be a direct current (DC) jack. In some embodiments, the pump assembly can comprise a disposable power source, such as batteries, so that no power jack is needed.

The canister 220 includes one or more feet 244 for placing the canister on a surface. The feet 244 can be formed out of rubber, silicone, or any other suitable material and can be angled at a suitable angle so that the canister 220 remains stable when placed on the surface. The canister 220 comprises a tube mount relief 246 configured to allow one or more tubes to exit to the front of the device. The canister 220 includes a stand or kickstand 248 for supporting the canister when it is placed on a surface. As explained below, the kickstand 248 can pivot between an opened and closed position. In closed position, the kickstand 248 can be latched to the canister 220. In some embodiments, the kickstand 248 can be made out of opaque material, such as plastic. In other embodiments, the kickstand 248 can be made out of transparent material. The kickstand 248 includes a gripping portion 242 formed in the kickstand. The gripping portion 242 can be configured to allow the user to place the kickstand 248 in the closed position. The kickstand 248 comprises a hole 249 to allow the user to place the kickstand in the open position. The hole 249 can be sized to allow the user to extend the kickstand using a finger.

Figure 2C:
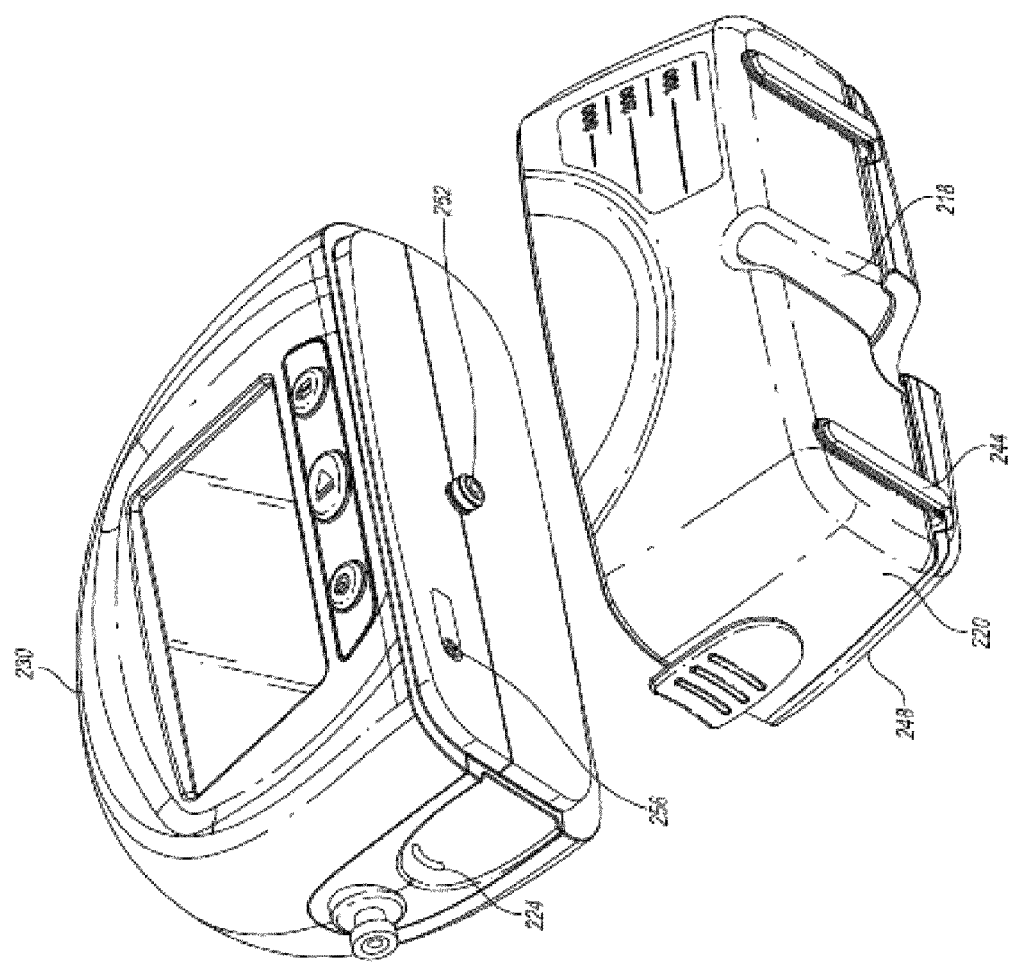

FIG. 2C illustrates a view of the pump assembly 230 separated from the canister 220 according to some embodiments. The pump assembly 230 includes a vacuum attachment, connector, or inlet 252 through which a vacuum pump communicates negative pressure to the canister 220. The pump assembly aspirates fluid, such as gas, from the wound via the inlet 252. The pump assembly 230 comprises a USB access door 256 configured to allow access to one or more USB ports. In some embodiments, the USB access door is omitted and USB ports are accessed through the door 234. The pump assembly 230 can include additional access doors configured to allow access to additional serial, parallel, or hybrid data transfer interfaces, such as SD, Compact Disc (CD), DVD, FireWire, Thunderbolt, PCI Express, and the like. In other embodiments, one or more of these additional ports are accessed through the door 234.

Pump Assembly Electronics and Components

Figure 3A:
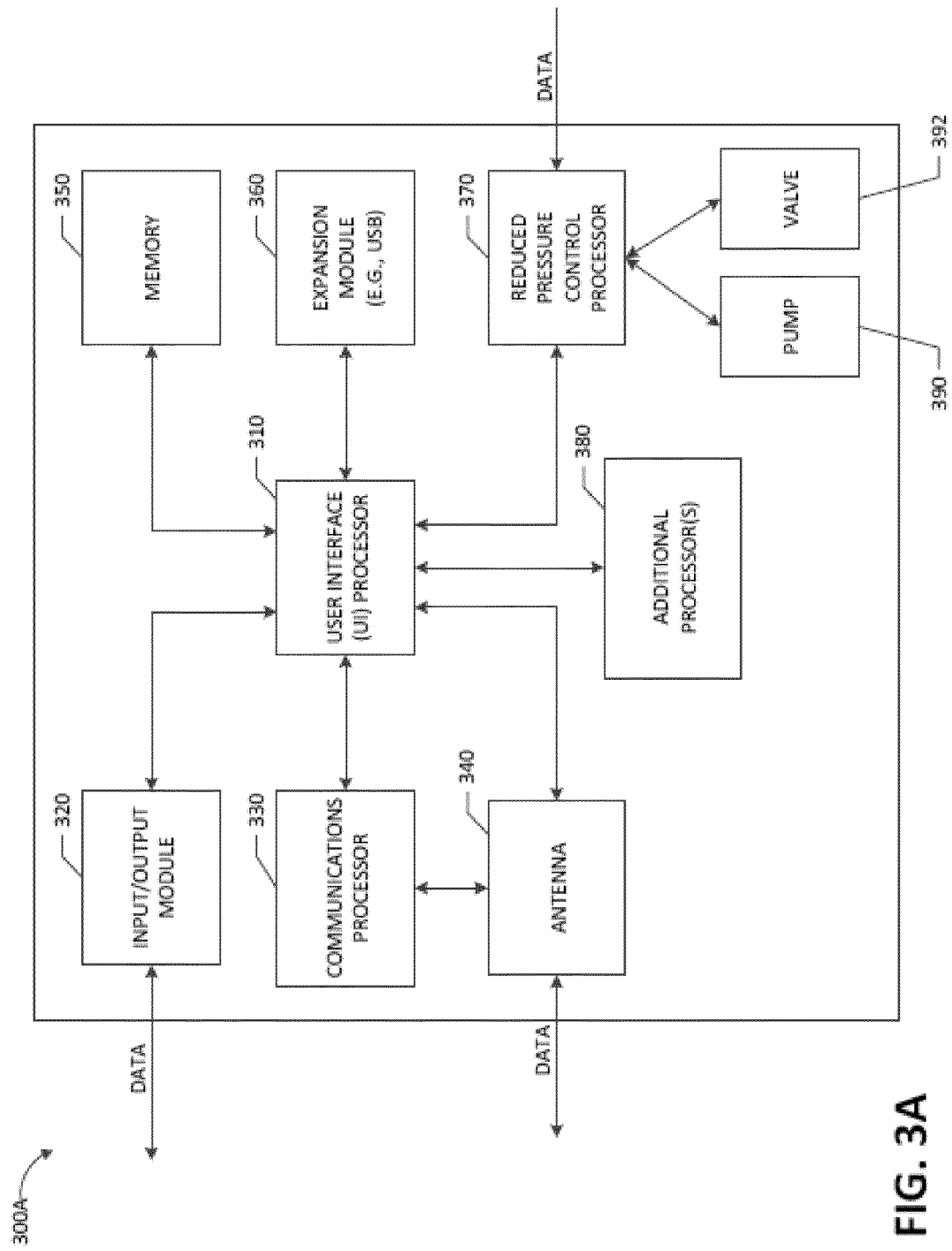
FIG. 3A illustrates an electrical component schematic of a pump assembly according to some embodiments.

FIG. 3A illustrates an electrical component schematic 300A of a pump assembly, such as the pump assembly 230, according to some embodiments. Electrical components can operate to accept user input, provide output to the user, operate the pump assembly and the TNP system, provide network connectivity, and so on. Electrical components can be mounted on one or more printed circuit boards (PCBs). As is illustrated, the pump assembly can include multiple processors.

The pump assembly can comprise a user interface processor or controller 310 configured to operate one or more components for accepting user input and providing output to the user, such as the display 206, buttons 212, etc. Input to the pump assembly and output from the pump assembly can controlled by an input/output (I/O) module 320. For example, the I/O module can receive data from one or more ports, such as serial, parallel, hybrid ports, and the like. The processor 310 also receives data from and provides data to one or more expansion modules 360, such as one or more USB ports, SD ports, Compact Disc (CD) drives, DVD drives, FireWire ports, Thunderbolt ports, PCI Express ports, and the like. The processor 310, along with other controllers or processors, stores data in one or more memory modules 350, which can be internal or external to the processor 310. Any suitable type of memory can be used, including volatile or non-volatile memory, such as RAM, ROM, magnetic memory, solid-state memory, magnetoresistive random-access memory (MRAM), and the like.

In some embodiments, the processor 310 can be a general purpose controller, such as a low-power processor. In other embodiments, the processor 310 can be an application specific processor. The processor 310 can be configured as a "central" processor in the electronic architecture of the pump assembly, and the processor 310 can coordinate the activity of other processors, such as a reduced pressure control processor 370, communications processor 330, and one or more additional processors 380 (e.g., processor for controlling the display 206, processor for controlling the buttons 212, etc.). The processor 310 can run a suitable operating system, such as a Linux, Windows CE, VxWorks, etc.

The reduced pressure control processor 370 can be configured to control the operation of a reduced pressure source, such as a pump 390, and a valve 392. The pump 390 can be a suitable pump, such as a diaphragm pump, peristaltic pump, rotary pump, rotary vane pump, scroll pump, screw pump, liquid ring pump, diaphragm pump operated by a piezoelectric transducer, voice coil pump, and the like. The valve 392 can be a suitable valve, such as a solenoid valve, diaphragm valve, and the like, and be positioned, for instance, downstream (or before) an exhaust for the pump assembly or in a fluid flow path between the pump assembly and a wound dressing. The valve 392 can be a single valve or composed of multiple different valves.

The reduced pressure control processor 370 can measure pressure in a fluid flow path, using data received from one or more pressure sensors, calculate the rate of fluid flow, and control the pump 390 and the valve 392. The reduced pressure control processor 370 can control a pump motor of the pump 390 so that a desired level of negative pressure is achieved in the wound cavity 110. The desired level of negative pressure can be pressure set or selected by the user. In various embodiments, the reduced pressure control processor 370 controls the pump (e.g., pump motor) using pulse-width modulation (PWM). A control signal for driving the pump 390 can be a 0-100% duty cycle PWM signal. Moreover, the reduced pressure control processor 370 can control opening and closing of the valve 392 so that a desired level of negative pressure is achieved in the wound cavity 110. The desired level of negative pressure can be pressure set or selected by the user or set automatically according to a mode of operation or setting for the pump assembly. In various embodiments, the reduced pressure control processor 370 controls the opening and closing of the valve 392 using PWM. A control signal for controlling or driving the valve 392 can be a 0-100% duty cycle PWM signal.

The reduced pressure control processor 370 can perform flow rate calculations and detect various conditions in a flow path. The reduced pressure control processor 370 can communicate information to the processor 310. The reduced pressure control processor 370 can include internal memory or can utilize memory 350. The reduced pressure control processor 370 can be a low-power processor.

A communications processor 330 can be configured to provide wired or wireless connectivity. The communications processor 330 can utilize one or more antennas 340 for sending and receiving data. The communications processor 330 can provide one or more of the following types of connections: Global Positioning System (GPS) technology, cellular connectivity (e.g., 2G, 3G, LTE, 4G), WiFi connectivity, Internet connectivity, and the like. Connectivity can be used for various activities, such as pump assembly location tracking, asset tracking, compliance monitoring, remote selection, uploading of logs, alarms, and other operational data, and adjustment of therapy settings, upgrading of software or firmware, and the like. The communications processor 330 can provide dual GPS/cellular functionality. Cellular functionality can, for example, be 3G functionality. The pump assembly can include a SIM card, and SIM-based positional information can be obtained.

The communications processor 330 can communicate information to the processor 310. The communications processor 330 can include internal memory or can utilize memory 350. The communications processor 330 can be a low-power processor.

In some embodiments, using the connectivity provided by the communications processor 330, the device can upload any of the data stored, maintained, or tracked by the pump assembly. The device can also download various operational data, such as therapy selection and parameters, firmware and software patches and upgrades, and the like.

Figure 3B:
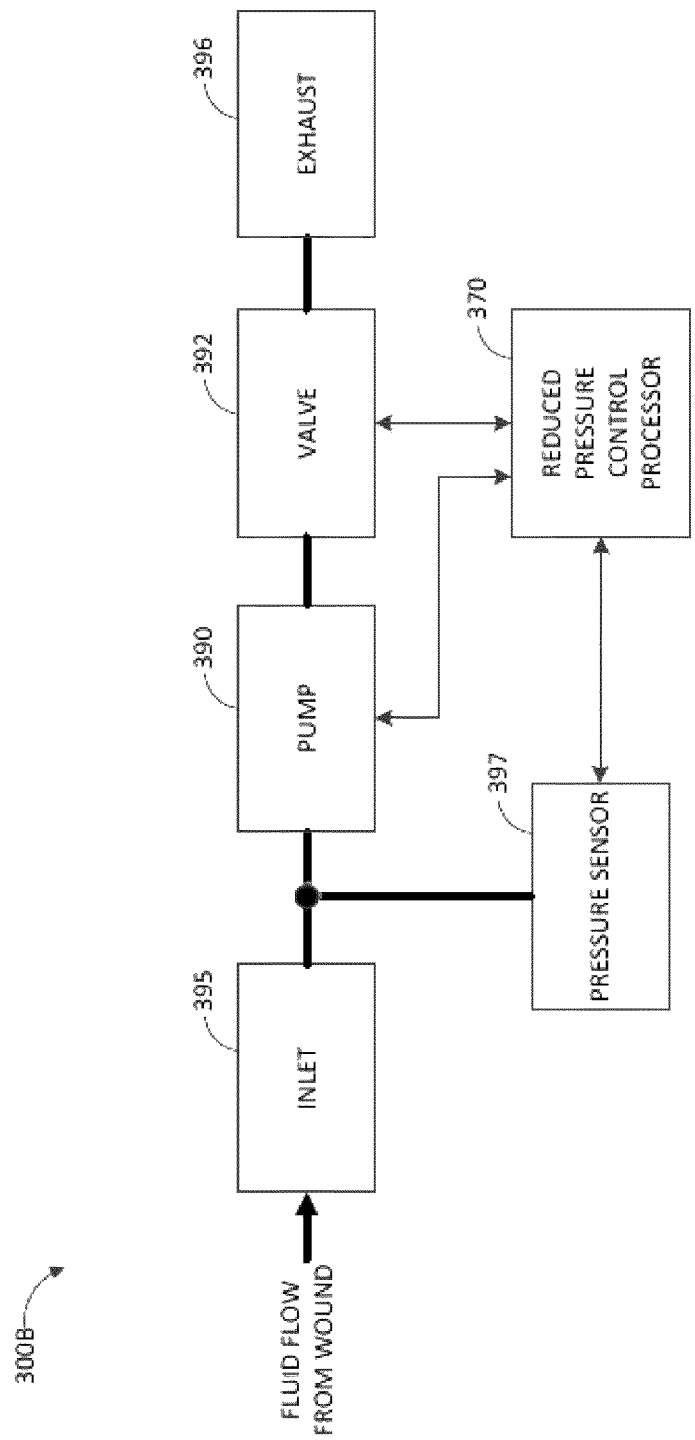
FIG. 3B illustrates a block diagram of components of a pump assembly according to some embodiments.

FIG. 3B illustrates a block diagram of certain components 300B of a pump assembly, such as the pump assembly 230, according to some embodiments. The components 300B include an inlet 395 (which can be like the inlet 252), the pump 390, the valve 392, an exhaust 396, a pressure sensor 397, and the reduced pressure control processor 370.

The pump 390 can provide negative pressure in a fluid flow path connecting the pump 390 (via the inlet 395) to a wound dressing placed over the wound, such that the negative pressure is provided to the inlet 395 and then to a wound dressing (for example, through a canister). The valve 392 can open (for example, partially or fully) to admit air, gas, or other fluid, which thereby provides positive pressure in the fluid flow path. In some implementations, the pump 390 under control of the reduced pressure control processor 370 can additionally or alternatively provide positive pressure in the fluid flow path, such as by operating the pump 390 in reverse. Additionally or alternatively, another pump different from the pump 390 and controllable by the reduced pressure control processor 370 can be included to provide positive pressure in the fluid flow path.

In some embodiments, the reduced pressure control processor 370 can measure the pressure in the fluid flow path near or at the inlet 395 (or at any other location in the fluid flow path, such as at the wound), using data received from one or more pressure sensors, such as the pressure sensor 397, calculate the rate of fluid flow, and control the pump 390 and the valve 392. The reduced pressure control processor 370 can, for instance, control one or more pump actuators, such as a pump motor of the pump 390, or one or more valve actuators, such as a solenoid of the valve 392, so that a desired level of negative (or positive) pressure is achieved at the wound. The desired level of negative pressure (or pressure setpoint) can be a pressure set or selected by the user or set automatically according to a mode of operation or setting for the pump assembly.

The components 300B can further include one or more additional sensors (not shown), such as a tachometer, positioned to detect or determine a level of activity of the pump 390 (for example, the pump motor) and provide indications responsive to the level of activity of the pump 390 to the reduced pressure control processor 370. For example, a tachometer can be separate from the pump 390 (for example, external to the pump) and positioned near or coupled to the pump 390, and the tachometer can detect a rotation (such as a partial rotation, complete rotation, or multiple partial or complete rotations) of a pump motor of the pump 390.

In some implementations, at least two pressure sensors can be positioned in or fluidically connected to the fluid flow path to permit differential measurement of the pressure. For example, a first pressure sensor can be positioned downstream of the wound dressing (such as at or near an inlet of the pump assembly) and a second pressure sensor can be positioned to detect pressure at or near the wound dressing or at or near a canister. This configuration can be accomplished by incorporating, in addition to one or more lumens forming a first fluid flow path connecting the pump assembly to the wound, a second fluid flow path that includes one or more lumens connecting the pump assembly to the wound dressing and through which the second pressure sensor can monitor pressure at or near the wound dressing or at or near the canister. The first and second fluid flow paths can be fluidically isolated from each other. When the at least two pressure sensors are used, the rate of change of pressure (for example, in peak-to-peak pressure or maximum pressure) in the first and second fluid flow paths can be determined and the difference in pressure detected between the first and second pressure sensors can be determined. These values can be used separately or together to detect various operational conditions, such as leaks, blockages, canister full, presence of blood in the first fluid flow path or the second fluid flow path, etc. Moreover, multiple redundant pressure sensors can be provided to protect against failure of one or more of the pressure sensors in some implementations.

Delivery of Negative Pressure Wound Therapy

In some embodiments, the pump assembly controls the vacuum pump to deliver negative pressure therapy to a wound according to a selected or programmed protocol. Pump control can be performed by the reduced pressure control processor 370 alone or in combination with the processor 310.

For example, the user can select continuous operation at a desired pressure (or negative pressure setpoint). The pump assembly can activate the vacuum pump to reduce or draw down the pressure at the wound (e.g., under the dressing) to reach the setpoint. As explained below, the drawdown can be performed by increasing the negative pressure at the wound limited by a maximum change in negative pressure per unit time called compression, until the setpoint (or another selected pressure value as explained below) has been achieved. Wound drawdown can be defined as the period of time immediately after therapy has been initiated during which the wound has not yet achieved the setpoint. As explained below, at the end of this period when the setpoint is achieved, the flow rate in the fluid flow path should be below a leak (or high flow) threshold and above a low vacuum threshold, otherwise an appropriate alarm will be activated.

As another example, the user can select intermittent operation between two desired pressures (or high and low pressure setpoints). The pump assembly can activate the vacuum pump to reduce or draw down the pressure at the wound to reach the high setpoint. Subsequently, the pump assembly can allow pressure at the wound to increase to reach the low setpoint. As explained below, decreasing and increasing negative pressure can be performed in accordance with the compression setting.

As yet another example, compression can be used anytime there is a change in the pressure setpoint (which can include stopping delivery of negative pressure). In some embodiments, different compression settings can be used for setpoint changes that result in decreasing or increasing pressure at the wound. In various embodiments, compression setting can be adjusted while a pressure setpoint is being achieved.

Figure 4:
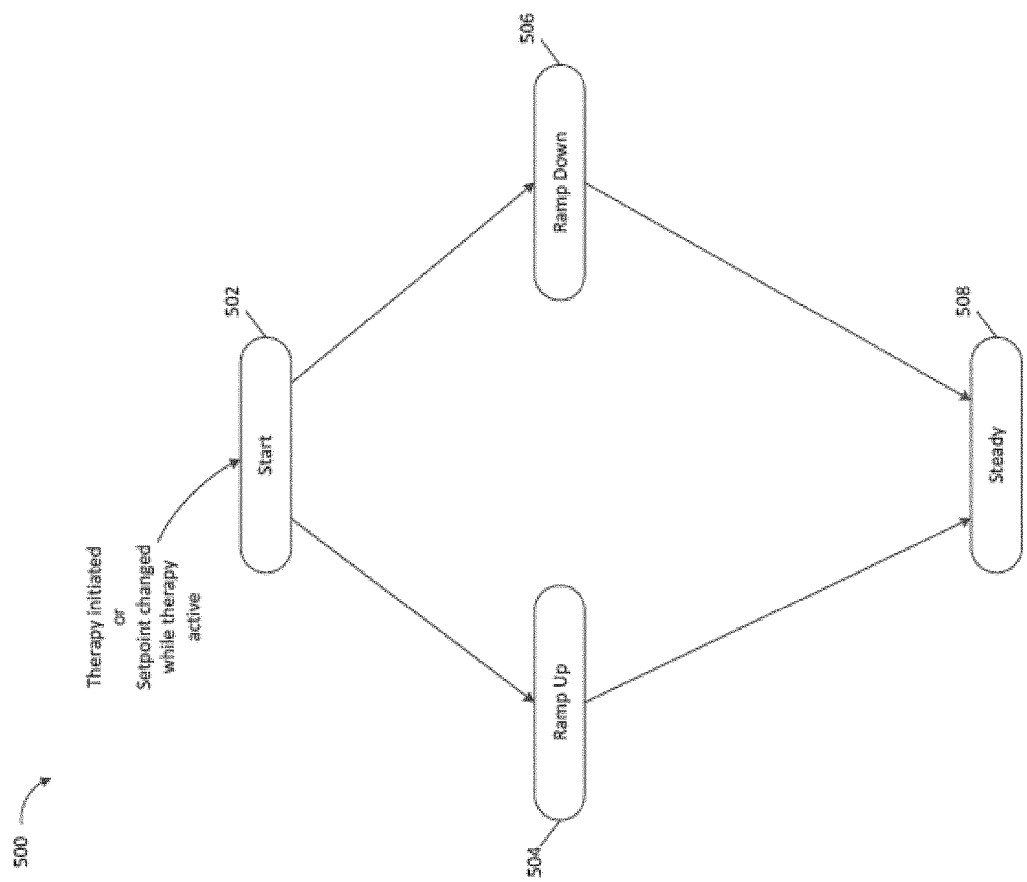
FIG. 4 illustrates a process of providing negative pressure wound therapy according to some embodiments.

FIG. 4 illustrates a process 500 for providing negative pressure wound therapy according to some embodiments. The process 500 can be executed by the reduced pressure control processor 370 alone or in combination with the processor 310 and utilize one or more components described herein or other systems not shown. The process 500 can be periodically executed, such as for example every 100 milliseconds (or 10 times per second) or at any other suitable frequency. Alternatively or additionally, the process 500 can be continuously executed.

The process 500 can begin in block 502, which it can transition to when therapy is initiated or when the setpoint is changed while therapy is being delivered. In block 502, the process 500 compares wound pressure, which can be determined as explained below, to the setpoint. For example, the process 500 can subtract the wound pressure from the setpoint or vice versa. If the wound pressure is below the setpoint, the process 500 can transition to block 504. Conversely, if the wound pressure exceeds or is equal to the setpoint, the process 500 can transition to block 506.

In block 504 (pressure ramp up), the process 500 can increment a pump ramp setpoint by an amount that depends on the compression setting as explained below. The vacuum pump will then attempt to draw down (or make more negative) the wound pressure to reach the current value of the pump ramp setpoint. For example, a suitable pump drive signal, such as voltage or current signal, can be generated and supplied to the pump motor so as to increase the speed of the pump motor to achieve wound draw down. For purposes of efficiency, the pump motor can be driven using PWM or any other suitable method. The process 500 can continue incrementing the pump ramp setpoint until it reaches the setpoint selected by the user. The process 500 can transition to block 508 when the wound pressure has nearly reached or reached the setpoint, which can correspond to reaching steady state pressure under the wound dressing. For example, the process 500 can transition to block 508 when the wound pressure is within a ramp up threshold pressure of the setpoint, such as within 2 mmHg of the setpoint or within any other suitable value. In some embodiments, the pump ramp setpoint can be adaptively set to a higher negative pressure than the setpoint. For example, as is explained below, the device can detect presence of one or more leaks which result in a higher level of flow. Because this can cause loss of pressure at the wound, the device can compensate such loss of pressure by increasing the pump ramp setpoint above the setpoint. For instance, the device can set the pump ramp setpoint to be 1%, 2%, 5%, etc. more negative than the setpoint. In certain embodiments, the pump ramp setpoint can be adaptively set to a lower negative pressure (or more positive pressure) than the setpoint.

In block 506 (pressure ramp down), the process 500 can set the pump ramp setpoint to the setpoint selected by the user (or to another set value as explained above). The process 500 can deactivate the pump so that the wound pressure is allowed to decay, such as due to one or more leaks in the fluid flow path, to reach or almost reach the setpoint. This can be performed in accordance with the compression setting, such as for example, deactivating the pump for a first period of time and then activating the pump for a second period of time so that pressure at the wound increases according to the compression setting.

Self-Contained Wound Dressing

Figure 5A:
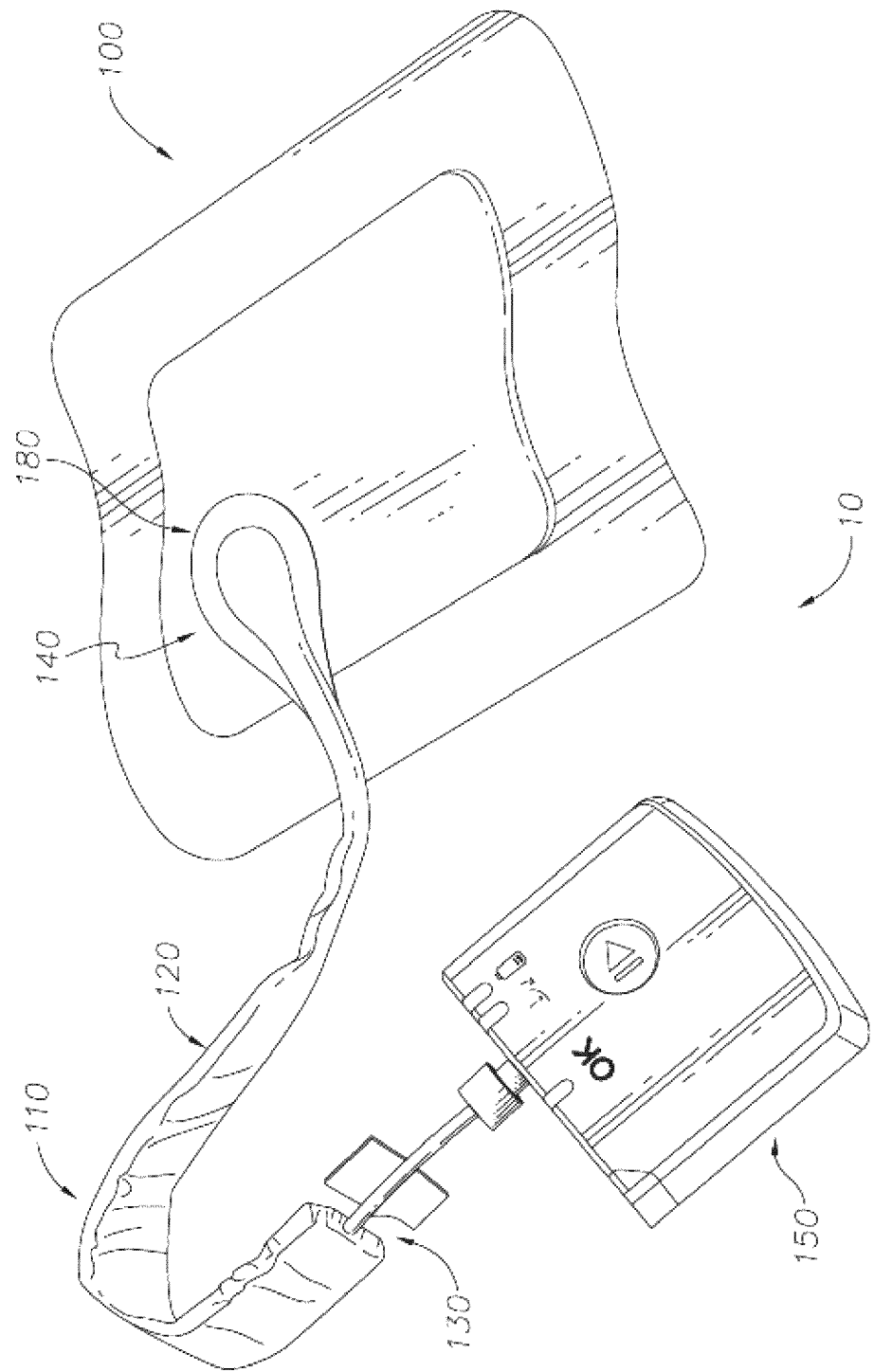
FIG. 5A illustrates an embodiment of a negative pressure wound treatment system employing a flexible fluidic connector and a wound dressing capable of absorbing and storing wound exudate.
Figure 5B:
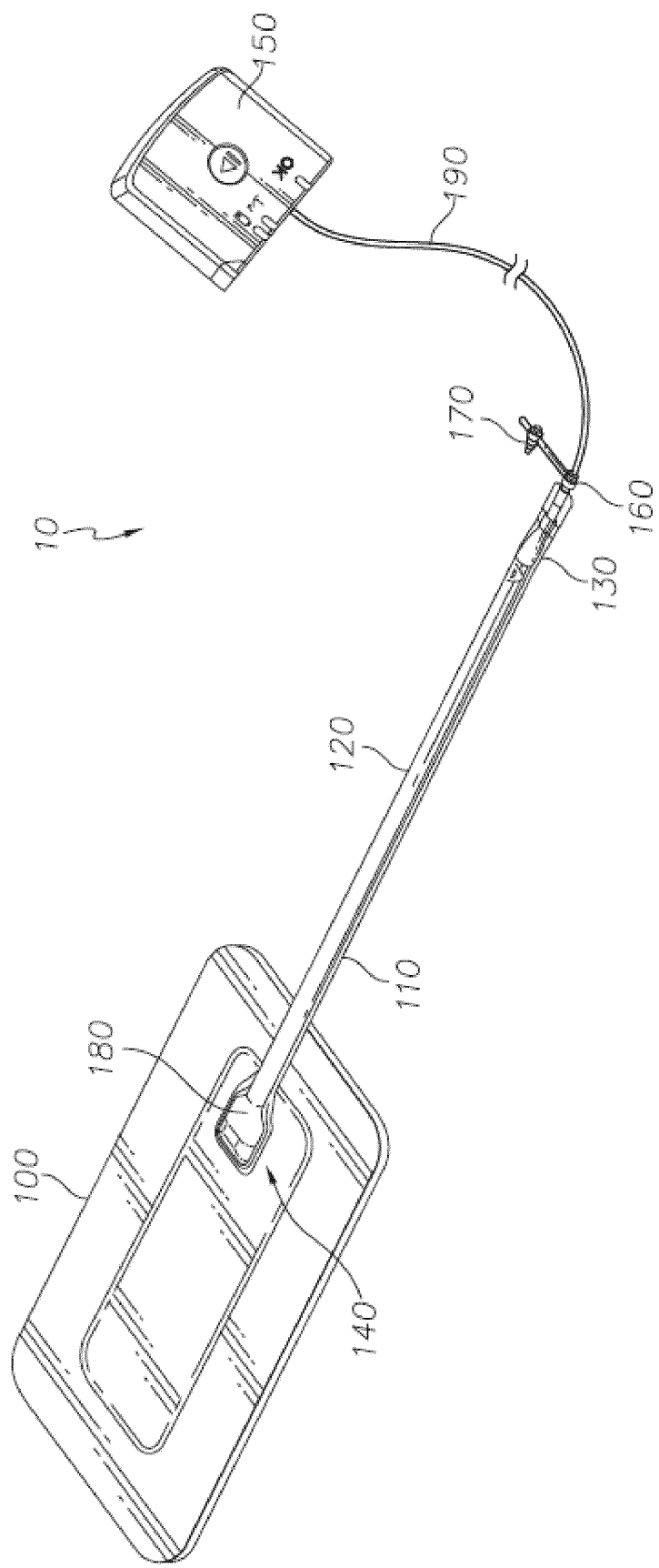
FIG. 5B illustrates an embodiment of a negative pressure wound treatment system employing a flexible fluidic connector and a wound dressing capable of absorbing and storing wound exudate.

In certain embodiments, NPWT may be applied to a wound through a self-contained wound dressing, such as a PICO™ wound dressing, as sold by Smith & Nephew. FIGS. 5A-B illustrate embodiments of a negative pressure wound treatment system 10 employing a wound dressing 100 in conjunction with a fluidic connector 110. Here, the fluidic connector 110 may comprise an elongate conduit, more preferably a bridge 120 having a proximal end 130 and a distal end 140, and an applicator 180 at the distal end 140 of the bridge 120. An optional coupling 160 is preferably disposed at the proximal end 130 of the bridge 120. A cap 170 may be provided with the system (and can in some cases, as illustrated, be attached to the coupling 160). The cap 170 can be useful in preventing fluids from leaking out of the proximal end 130. The system 10 may include a source of negative pressure such as a pump or negative pressure unit 150 capable of supplying negative pressure. The pump may comprise a canister or other container for the storage of wound exudates and other fluids that may be removed from the wound. A canister or container may also be provided separate from the pump. In some embodiments, such as illustrated in FIGS. 5A-5B, the pump 150 can be a canisterless pump such as the PICO™ pump, as sold by Smith & Nephew. The pump 150 may be connected to the coupling 160 via a tube 190, or the pump 150 may be connected directly to the coupling 160 or directly to the bridge 120. In use, the dressing 100 is placed over a suitably-prepared wound, which may in some cases be filled with a wound packing material such as foam or gauze. The applicator 180 of the fluidic connector 110 has a sealing surface that is placed over an aperture in the dressing 100 and is sealed to the top surface of the dressing 100. Either before, during, or after connection of the fluidic connector 110 to the dressing 100, the pump 150 is connected via the tube 190 to the coupling 160, or is connected directly to the coupling 160 or to the bridge 120. The pump is then activated, thereby supplying negative pressure to the wound. Application of negative pressure may be applied until a desired level of healing of the wound is achieved.

Figure 6A:
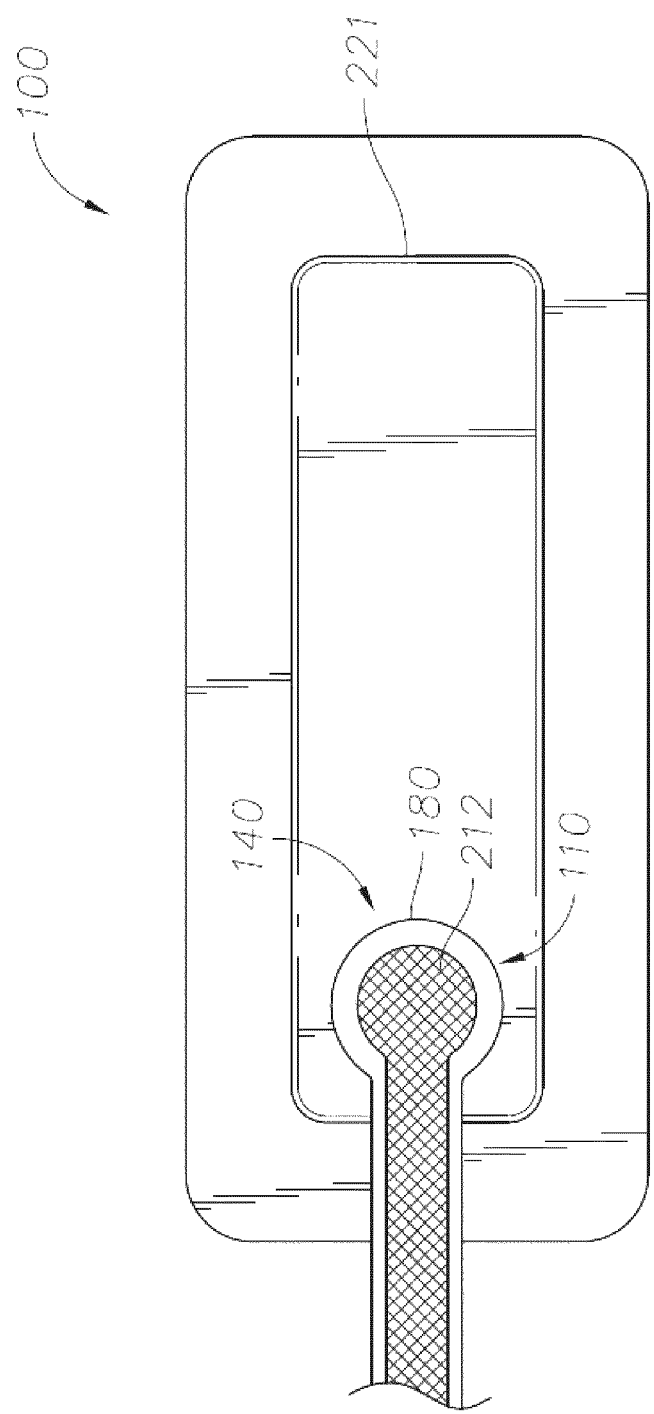
FIG. 6A illustrates an embodiment of a negative pressure wound treatment system employing a flexible fluidic connector and a wound dressing capable of absorbing and storing wound exudate.

As shown in FIG. 6A, the fluidic connector 110 preferably comprises an enlarged distal end, or head 140 that is in fluidic communication with the dressing 100 as will be described in further detail below. In one embodiment, the enlarged distal end has a round or circular shape. The head 140 is illustrated here as being positioned near an edge of the dressing 100, but may also be positioned at any location on the dressing. For example, some embodiments may provide for a centrally or off-centered location not on or near an edge or corner of the dressing 100. In some embodiments, the dressing 10 may comprise two or more fluidic connectors 110, each comprising one or more heads 140, in fluidic communication therewith. In a preferred embodiment, the head 140 may measure 30 mm along its widest edge. The head 140 forms at least in part the applicator 180, described above, that is configured to seal against a top surface of the wound dressing.

Figure 6B:
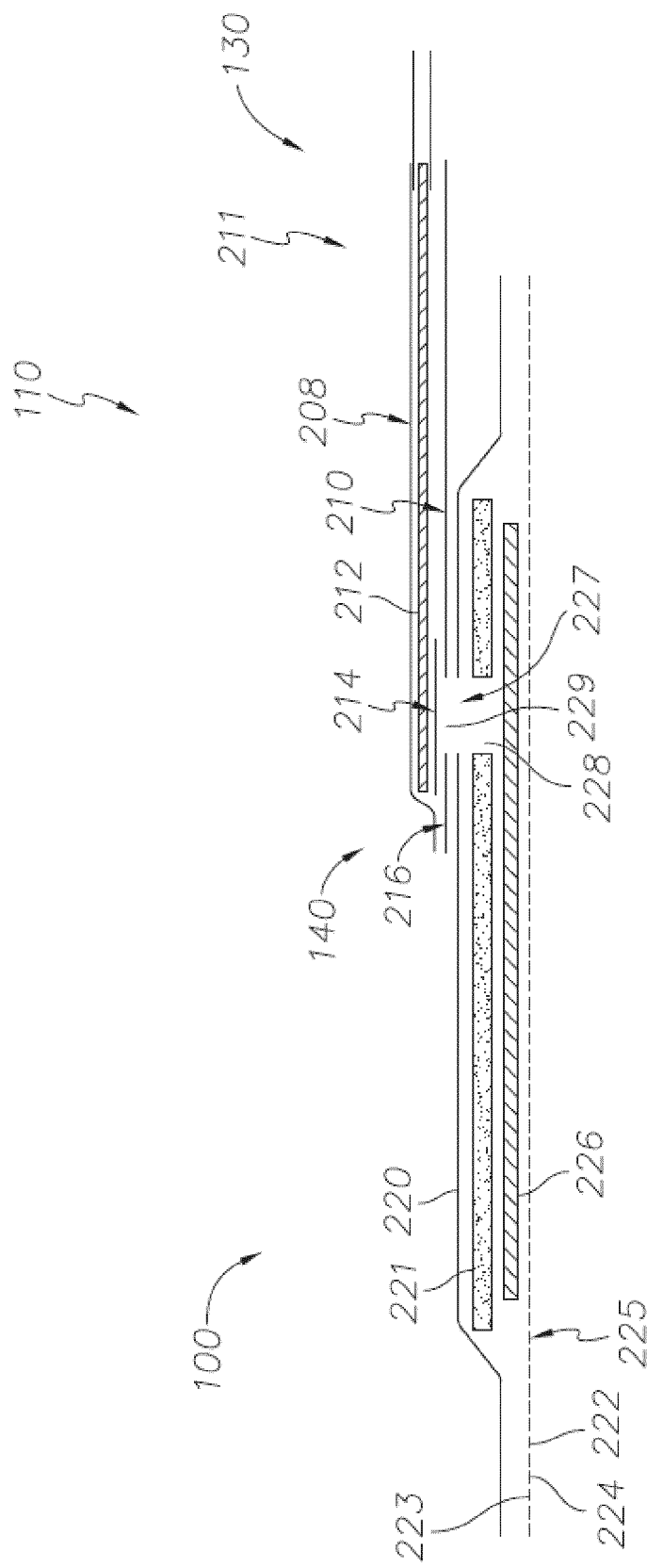
FIG. 6B illustrates a cross section of an embodiment of a fluidic connector connected to a wound dressing.

FIG. 6B illustrates a cross-section through a wound dressing 100 similar to the wound dressing 10 as shown in FIG. 5B and described in International Patent Publication WO2013175306 A2, which is incorporated by reference in its entirety, along with fluidic connector 110. The wound dressing 100, which can alternatively be any wound dressing embodiment disclosed herein or any combination of features of any number of wound dressing embodiments disclosed herein, can be located over a wound site to be treated. The dressing 100 may be placed as to form a sealed cavity over the wound site. In a preferred embodiment, the dressing 100 comprises a top or cover layer, or backing layer 220 attached to an optional wound contact layer 222, both of which are described in greater detail below. These two layers 220, 222 are preferably joined or sealed together so as to define an interior space or chamber. This interior space or chamber may comprise additional structures that may be adapted to distribute or transmit negative pressure, store wound exudate and other fluids removed from the wound, and other functions which will be explained in greater detail below. Examples of such structures, described below, include a transmission layer 226 and an absorbent layer 221.

As used herein the upper layer, top layer, or layer above refers to a layer furthest from the surface of the skin or wound while the dressing is in use and positioned over the wound. Accordingly, the lower surface, lower layer, bottom layer, or layer below refers to the layer that is closest to the surface of the skin or wound while the dressing is in use and positioned over the wound.

As illustrated in FIG. 6B, the wound contact layer 222 can be a polyurethane layer or polyethylene layer or other flexible layer which is perforated, for example via a hot pin process, laser ablation process, ultrasound process or in some other way or otherwise made permeable to liquid and gas. The wound contact layer 222 has a lower surface 224 and an upper surface 223. The perforations 225 preferably comprise through holes in the wound contact layer 222 which enable fluid to flow through the layer 222. The wound contact layer 222 helps prevent tissue ingrowth into the other material of the wound dressing. Preferably, the perforations are small enough to meet this requirement while still allowing fluid to flow therethrough. For example, perforations formed as slits or holes having a size ranging from 0.025 mm to 1.2 mm are considered small enough to help prevent tissue ingrowth into the wound dressing while allowing wound exudate to flow into the dressing. In some configurations, the wound contact layer 222 may help maintain the integrity of the entire dressing 100 while also creating an air tight seal around the absorbent pad in order to maintain negative pressure at the wound.

Some embodiments of the wound contact layer 222 may also act as a carrier for an optional lower and upper adhesive layer (not shown). For example, a lower pressure sensitive adhesive may be provided on the lower surface 224 of the wound dressing 100 whilst an upper pressure sensitive adhesive layer may be provided on the upper surface 223 of the wound contact layer. The pressure sensitive adhesive, which may be a silicone, hot melt, hydrocolloid or acrylic based adhesive or other such adhesives, may be formed on both sides or optionally on a selected one or none of the sides of the wound contact layer. When a lower pressure sensitive adhesive layer is utilized may be helpful to adhere the wound dressing 100 to the skin around a wound site. In some embodiments, the wound contact layer may comprise perforated polyurethane film. The lower surface of the film may be provided with a silicone pressure sensitive adhesive and the upper surface may be provided with an acrylic pressure sensitive adhesive, which may help the dressing maintain its integrity. In some embodiments, a polyurethane film layer may be provided with an adhesive layer on both its upper surface and lower surface, and all three layers may be perforated together.

A layer 226 of porous material can be located above the wound contact layer 222. This porous layer, or transmission layer, 226 allows transmission of fluid including liquid and gas away from a wound site into upper layers of the wound dressing. In particular, the transmission layer 226 preferably ensures that an open air channel can be maintained to communicate negative pressure over the wound area even when the absorbent layer has absorbed substantial amounts of exudates. The layer 226 should preferably remain open under the typical pressures that will be applied during negative pressure wound therapy as described above, so that the whole wound site sees an equalized negative pressure. The layer 226 may be formed of a material having a three dimensional structure. For example, a knitted or woven spacer fabric (for example Baltex 7970 weft knitted polyester) or a non-woven fabric could be used.

In some embodiments, the transmission layer 226 comprises a 3D polyester spacer fabric layer including a top layer (that is to say, a layer distal from the wound-bed in use) which is a 84/144 textured polyester, and a bottom layer (that is to say, a layer which lies proximate to the wound bed in use) which is a 10 denier flat polyester and a third layer formed sandwiched between these two layers which is a region defined by a knitted polyester viscose, cellulose or the like mono filament fiber. Other materials and other linear mass densities of fiber could of course be used.

Whilst reference is made throughout this disclosure to a monofilament fiber it will be appreciated that a multistrand alternative could of course be utilized. The top spacer fabric thus has more filaments in a yarn used to form it than the number of filaments making up the yarn used to form the bottom spacer fabric layer.

This differential between filament counts in the spaced apart layers helps control moisture flow across the transmission layer. Particularly, by having a filament count greater in the top layer, that is to say, the top layer is made from a yarn having more filaments than the yarn used in the bottom layer, liquid tends to be wicked along the top layer more than the bottom layer. In use, this differential tends to draw liquid away from the wound bed and into a central region of the dressing where the absorbent layer 221 helps lock the liquid away or itself wicks the liquid onwards towards the cover layer where it can be transpired.

Preferably, to improve the liquid flow across the transmission layer 226 (that is to say perpendicular to the channel region formed between the top and bottom spacer layers, the 3D fabric may be treated with a dry cleaning agent (such as, but not limited to, Perchloro Ethylene) to help remove any manufacturing products such as mineral oils, fats and/or waxes used previously which might interfere with the hydrophilic capabilities of the transmission layer. In some embodiments, an additional manufacturing step can subsequently be carried in which the 3D spacer fabric is washed in a hydrophilic agent (such as, but not limited to, Feran Ice 30 g/l available from the Rudolph Group). This process step helps ensure that the surface tension on the materials is so low that liquid such as water can enter the fabric as soon as it contacts the 3D knit fabric. This also aids in controlling the flow of the liquid insult component of any exudates.

A layer 221 of absorbent material is provided above the transmission layer 226. The absorbent material, which comprise a foam or non-woven natural or synthetic material, and which may optionally comprise a super-absorbent material, forms a reservoir for fluid, particularly liquid, removed from the wound site. In some embodiments, the layer 10 may also aid in drawing fluids towards the backing layer 220.

The material of the absorbent layer 221 may also prevent liquid collected in the wound dressing 100 from flowing freely within the dressing, and preferably acts so as to contain any liquid collected within the dressing. The absorbent layer 221 also helps distribute fluid throughout the layer via a wicking action so that fluid is drawn from the wound site and stored throughout the absorbent layer. This helps prevent agglomeration in areas of the absorbent layer. The capacity of the absorbent material must be sufficient to manage the exudates flow rate of a wound when negative pressure is applied. Since in use the absorbent layer experiences negative pressures the material of the absorbent layer is chosen to absorb liquid under such circumstances. A number of materials exist that are able to absorb liquid when under negative pressure, for example superabsorber material. The absorbent layer 221 may typically be manufactured from ALLEVYN™ foam, Freudenberg 114-224-4 and/or Chem-Posite™11C-450. In some embodiments, the absorbent layer 221 may comprise a composite comprising superabsorbent powder, fibrous material such as cellulose, and bonding fibers. In a preferred embodiment, the composite is an airlaid, thermally-bonded composite.

In some embodiments, the absorbent layer 221 is a layer of non-woven cellulose fibers having super-absorbent material in the form of dry particles dispersed throughout. Use of the cellulose fibers introduces fast wicking elements which help quickly and evenly distribute liquid taken up by the dressing. The juxtaposition of multiple strand-like fibers leads to strong capillary action in the fibrous pad which helps distribute liquid. In this way, the super-absorbent material is efficiently supplied with liquid. The wicking action also assists in bringing liquid into contact with the upper cover layer to aid increase transpiration rates of the dressing.

An aperture, hole, or orifice 227 is preferably provided in the backing layer 220 to allow a negative pressure to be applied to the dressing 100. The fluidic connector 110 is preferably attached or sealed to the top of the backing layer 220 over the orifice 227 made into the dressing 100, and communicates negative pressure through the orifice 227. A length of tubing may be coupled at a first end to the fluidic connector 110 and at a second end to a pump unit (not shown) to allow fluids to be pumped out of the dressing. Where the fluidic connector is adhered to the top layer of the wound dressing, a length of tubing may be coupled at a first end of the fluidic connector such that the tubing, or conduit, extends away from the fluidic connector parallel or substantially to the top surface of the dressing. The fluidic connector 110 may be adhered and sealed to the backing layer 220 using an adhesive such as an acrylic, cyanoacrylate, epoxy, UV curable or hot melt adhesive. The fluidic connector 110 may be formed from a soft polymer, for example a polyethylene, a polyvinyl chloride, a silicone or polyurethane having a hardness of 30 to 90 on the Shore A scale. In some embodiments, the fluidic connector 110 may be made from a soft or conformable material.

Preferably the absorbent layer 221 includes at least one through hole 228 located so as to underlie the fluidic connector 110. The through hole 228 may in some embodiments be the same size as the opening 227 in the backing layer, or may be bigger or smaller. As illustrated in FIG. 6B a single through hole can be used to produce an opening underlying the fluidic connector 110. It will be appreciated that multiple openings could alternatively be utilized. Additionally should more than one port be utilized according to certain embodiments of the present disclosure one or multiple openings may be made in the absorbent layer and the obscuring layer in registration with each respective fluidic connector. Although not essential to certain embodiments of the present disclosure the use of through holes in the super-absorbent layer may provide a fluid flow pathway which remains unblocked in particular when the absorbent layer is near saturation.

The aperture or through-hole 228 is preferably provided in the absorbent layer 221 beneath the orifice 227 such that the orifice is connected directly to the transmission layer 226 as illustrated in FIG. 6B. This allows the negative pressure applied to the fluidic connector 110 to be communicated to the transmission layer 226 without passing through the absorbent layer 221. This ensures that the negative pressure applied to the wound site is not inhibited by the absorbent layer as it absorbs wound exudates. In other embodiments, no aperture may be provided in the absorbent layer 221, or alternatively a plurality of apertures underlying the orifice 227 may be provided. In further alternative embodiments, additional layers such as another transmission layer or an obscuring layer such as described in International Patent Publication WO2014020440, the entirety of which is hereby incorporated by reference, may be provided over the absorbent layer 221 and beneath the backing layer 220.

The backing layer 220 is preferably gas impermeable, but moisture vapor permeable, and can extend across the width of the wound dressing 100. The backing layer 220, which may for example be a polyurethane film (for example, Elastollan SP9109) having a pressure sensitive adhesive on one side, is impermeable to gas and this layer thus operates to cover the wound and to seal a wound cavity over which the wound dressing is placed. In this way an effective chamber is made between the backing layer 220 and a wound site where a negative pressure can be established. The backing layer 220 is preferably sealed to the wound contact layer 222 in a border region around the circumference of the dressing, ensuring that no air is drawn in through the border area, for example via adhesive or welding techniques. The backing layer 220 protects the wound from external bacterial contamination (bacterial barrier) and allows liquid from wound exudates to be transferred through the layer and evaporated from the film outer surface. The backing layer 220 preferably comprises two layers; a polyurethane film and an adhesive pattern spread onto the film. The polyurethane film is preferably moisture vapor permeable and may be manufactured from a material that has an increased water transmission rate when wet. In some embodiments the moisture vapor permeability of the backing layer increases when the backing layer becomes wet. The moisture vapor permeability of the wet backing layer may be up to about ten times more than the moisture vapor permeability of the dry backing layer.

The absorbent layer 221 may be of a greater area than the transmission layer 226, such that the absorbent layer overlaps the edges of the transmission layer 226, thereby ensuring that the transmission layer does not contact the backing layer 220. This provides an outer channel of the absorbent layer 221 that is in direct contact with the wound contact layer 222, which aids more rapid absorption of exudates to the absorbent layer. Furthermore, this outer channel ensures that no liquid is able to pool around the circumference of the wound cavity, which may otherwise seep through the seal around the perimeter of the dressing leading to the formation of leaks. As illustrated in FIGS. 6A-6B, the absorbent layer 221 may define a smaller perimeter than that of the backing layer 220, such that a boundary or border region is defined between the edge of the absorbent layer 221 and the edge of the backing layer 220.

As shown in FIG. 6B, one embodiment of the wound dressing 100 comprises an aperture 228 in the absorbent layer 221 situated underneath the fluidic connector 110. In use, for example when negative pressure is applied to the dressing 100, a wound facing portion of the fluidic connector may thus come into contact with the transmission layer 226, which can thus aid in transmitting negative pressure to the wound site even when the absorbent layer 221 is filled with wound fluids. Some embodiments may have the backing layer 220 be at least partly adhered to the transmission layer 226. In some embodiments, the aperture 228 is at least 1-2 mm larger than the diameter of the wound facing portion of the fluidic connector 11, or the orifice 227.

In particular for embodiments with a single fluidic connector 110 and through hole, it may be preferable for the fluidic connector 110 and through hole to be located in an off-center position as illustrated in FIG. 6A. Such a location may permit the dressing 100 to be positioned onto a patient such that the fluidic connector 110 is raised in relation to the remainder of the dressing 100. So positioned, the fluidic connector 110 and the filter 214 may be less likely to come into contact with wound fluids that could prematurely occlude the filter 214 so as to impair the transmission of negative pressure to the wound site.

Turning now to the fluidic connector 110, preferred embodiments comprise a sealing surface 216, a bridge 211 (corresponding to bridge 120 in FIGS. 5A-5B) with a proximal end 130 and a distal end 140, and a filter 214. The sealing surface 216 preferably forms the applicator previously described that is sealed to the top surface of the wound dressing. In some embodiments a bottom layer of the fluidic connector 110 may comprise the sealing surface 216. The fluidic connector 110 may further comprise an upper surface vertically spaced from the sealing surface 216, which in some embodiments is defined by a separate upper layer of the fluidic connector. In other embodiments the upper surface and the lower surface may be formed from the same piece of material. In some embodiments the sealing surface 216 may comprise at least one aperture 229 therein to communicate with the wound dressing. In some embodiments the filter 214 may be positioned across the opening 229 in the sealing surface, and may span the entire opening 229. The sealing surface 216 may be configured for sealing the fluidic connector to the cover layer of the wound dressing, and may comprise an adhesive or weld. In some embodiments, the sealing surface 216 may be placed over an orifice in the cover layer with optional spacer elements 215 configured to create a gap between the filter 214 and the transmission layer 226. In other embodiments, the sealing surface 216 may be positioned over an orifice in the cover layer and an aperture in the absorbent layer 220, permitting the fluidic connector 110 to provide air flow through the transmission layer 226. In some embodiments, the bridge 211 may comprise a first fluid passage 212 in communication with a source of negative pressure, the first fluid passage 212 comprising a porous material, such as a 3D knitted material, which may be the same or different than the porous layer 226 described previously. The bridge 211 is preferably encapsulated by at least one flexible film layer 208, 210 having a proximal and distal end and configured to surround the first fluid passage 212, the distal end of the flexible film being connected the sealing surface 216. The filter 214 is configured to substantially prevent wound exudate from entering the bridge, and spacer elements 215 are configured to prevent the fluidic connector from contacting the transmission layer 226. These elements will be described in greater detail below.

Some embodiments may further comprise an optional second fluid passage positioned above the first fluid passage 212. For example, some embodiments may provide for an air leak may be disposed at the proximal end of the top layer that is configured to provide an air path into the first fluid passage 212 and dressing 100 similar to the suction adapter as described in U.S. Pat. No. 8,801,685, which is incorporated by reference herein in its entirety.

Preferably, the fluid passage 212 is constructed from a compliant material that is flexible and that also permits fluid to pass through it if the spacer is kinked or folded over. Suitable materials for the fluid passage 212 include without limitation foams, including open-cell foams such as polyethylene or polyurethane foam, meshes, 3D knitted fabrics, non-woven materials, and fluid channels. In some embodiments, the fluid passage 212 may be constructed from materials similar to those described above in relation to the transmission layer 226. Advantageously, such materials used in the fluid passage 212 not only permit greater patient comfort, but may also provide greater kink resistance, such that the fluid passage 212 is still able to transfer fluid from the wound toward the source of negative pressure while being kinked or bent.

In some embodiments, the fluid passage 212 may be comprised of a wicking fabric, for example a knitted or woven spacer fabric (such as a knitted polyester 3D fabric, Baltex 7970®, or Gehring 879®) or a nonwoven fabric. These materials selected are preferably suited to channeling wound exudate away from the wound and for transmitting negative pressure and/or vented air to the wound site, and may also confer a degree of kinking or occlusion resistance to the fluid passage 212. In some embodiments, the wicking fabric may have a three-dimensional structure, which in some cases may aid in wicking fluid or transmitting negative pressure. In certain embodiments, including wicking fabrics, these materials remain open and capable of communicating negative pressure to a wound area under the typical pressures used in negative pressure therapy, for example between 40 to 150 mmHg In some embodiments, the wicking fabric may comprise several layers of material stacked or layered over each other, which may in some cases be useful in preventing the fluid passage 212 from collapsing under the application of negative pressure. In other embodiments, the wicking fabric used in the fluid passage 212 may be between 1.5 mm and 6 mm; more preferably, the wicking fabric may be between 3 mm and 6 mm thick, and may be comprised of either one or several individual layers of wicking fabric. In other embodiments, the fluid passage 212 may be between 1.2-3 mm thick, and preferably thicker than 1.5 mm Some embodiments, for example a suction adapter used with a dressing which retains liquid such as wound exudate, may employ hydrophobic layers in the fluid passage 212, and only gases may travel through the fluid passage 212. Additionally, and as described previously, the materials used in the system are preferably conformable and soft, which may help to avoid pressure ulcers and other complications which may result from a wound treatment system being pressed against the skin of a patient.

Preferably, the filter element 214 is impermeable to liquids, but permeable to gases, and is provided to act as a liquid barrier and to ensure that no liquids are able to escape from the wound dressing 100. The filter element 214 may also function as a bacterial barrier. Typically the pore size is 0.2 µm. Suitable materials for the filter material of the filter element 214 include 0.2 micron Gore™ expanded PTFE from the MMT range, PALL Versapore™ 200R, and Donaldson™ TX6628. Larger pore sizes can also be used but these may require a secondary filter layer to ensure full bioburden containment. As wound fluid contains lipids it is preferable, though not essential, to use an oleophobic filter membrane for example 1.0 micron MMT-332 prior to 0.2 micron MMT-323. This prevents the lipids from blocking the hydrophobic filter. The filter element can be attached or sealed to the port and/or the cover film over the orifice. For example, the filter element 214 may be molded into the fluidic connector 110, or may be adhered to one or both of the top of the cover layer and bottom of the suction adapter 110 using an adhesive such as, but not limited to, a UV cured adhesive.

It will be understood that other types of material could be used for the filter element 214. More generally a microporous membrane can be used which is a thin, flat sheet of polymeric material, this contains billions of microscopic pores. Depending upon the membrane chosen these pores can range in size from 0.01 to more than 10 micrometers. Microporous membranes are available in both hydrophilic (water filtering) and hydrophobic (water repellent) forms. In some embodiments of the present disclosure, filter element 214 comprises a support layer and an acrylic co-polymer membrane formed on the support layer. Preferably the wound dressing 100 according to certain embodiments of the present disclosure uses microporous hydrophobic membranes (MHMs). Numerous polymers may be employed to form MHMs. For example, the MHMs may be formed from one or more of PTFE, polypropylene, PVDF and acrylic copolymer. All of these optional polymers can be treated in order to obtain specific surface characteristics that can be both hydrophobic and oleophobic. As such these will repel liquids with low surface tensions such as multi-vitamin infusions, lipids, surfactants, oils and organic solvents.

MHMs block liquids whilst allowing air to flow through the membranes. They are also highly efficient air filters eliminating potentially infectious aerosols and particles. A single piece of MHM is well known as an option to replace mechanical valves or vents. Incorporation of MHMs can thus reduce product assembly costs improving profits and costs/benefit ratio to a patient.

The filter element 214 may also include an odor absorbent material, for example activated charcoal, carbon fiber cloth or Vitec Carbotec-RT Q2003073 foam, or the like. For example, an odor absorbent material may form a layer of the filter element 214 or may be sandwiched between microporous hydrophobic membranes within the filter element. The filter element 214 thus enables gas to be exhausted through the orifice. Liquid, particulates and pathogens however are contained in the dressing.

The wound dressing 100 may comprise spacer elements 215 in conjunction with the fluidic connector 110 and the filter 214. With the addition of such spacer elements 215 the fluidic connector 110 and filter 214 may be supported out of direct contact with the absorbent layer 220 and/or the transmission layer 226. The absorbent layer 220 may also act as an additional spacer element to keep the filter 214 from contacting the transmission layer 226. Accordingly, with such a configuration contact of the filter 214 with the transmission layer 226 and wound fluids during use may thus be minimized.

Similar to the embodiments of wound dressings described above, some wound dressings comprise a perforated wound contact layer with silicone adhesive on the skin-contact face and acrylic adhesive on the reverse. Above this bordered layer sits a transmission layer or a 3D spacer fabric pad. Above the transmission layer, sits an absorbent layer. The absorbent layer can include a superabsorbent non-woven (NW) pad. The absorbent layer can over-border the transmission layer by approximately 5 mm at the perimeter. The absorbent layer can have an aperture or through-hole toward one end. The aperture can be about 10 mm in diameter. Over the transmission layer and absorbent layer lies a backing layer. The backing layer can be a high moisture vapor transmission rate (MVTR) film, pattern coated with acrylic adhesive. The high MVTR film and wound contact layer encapsulate the transmission layer and absorbent layer, creating a perimeter border of approximately 20 mm. The backing layer can have a 10 mm aperture that overlies the aperture in the absorbent layer. A fluidic connector can be bonded above the hole, the fluid connector comprising a liquid-impermeable, gas-permeable semi-permeable membrane (SPM) or filter that overlies the aforementioned apertures.

Treatment of Abdominal Wounds

Figure 7:
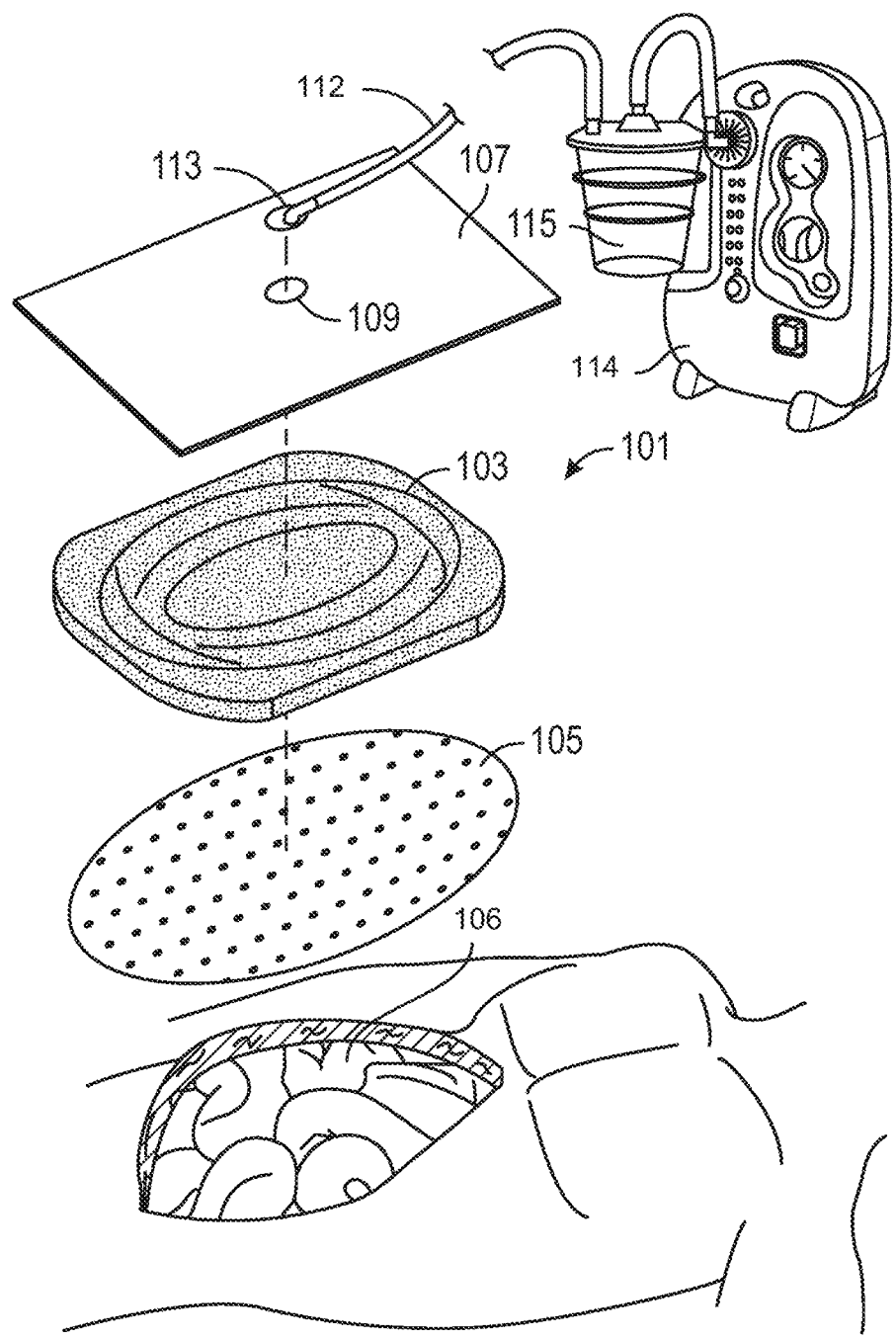
FIG. 7 illustrates an embodiment of a negative pressure wound therapy system.

Turning to FIG. 7, treatment of other wound types, such as larger abdominal wounds, with negative pressure in certain embodiments uses a negative pressure treatment system 101 as illustrated schematically here. In this embodiment, a wound site 106, illustrated here as an abdominal wound site, may benefit from treatment with negative pressure. Such abdominal wound sites may be a result of, for example, an accident or due to surgical intervention. In some cases, medical conditions such as abdominal compartment syndrome, abdominal hypertension, sepsis, or fluid edema may require decompression of the abdomen with a surgical incision through the abdominal wall to expose the peritoneal space, after which the opening may need to be maintained in an open, accessible state until the condition resolves. Other conditions may also necessitate that an opening—particularly in the abdominal cavity—remain open, for example if multiple surgical procedures are required (possibly incidental to trauma), or there is evidence of clinical conditions such as peritonitis or necrotizing fasciitis.

In cases where there is a wound, particularly in the abdomen, management of possible complications relating to the exposure of organs and the peritoneal space is desired, whether or not the wound is to remain open or if it will be closed. Therapy, preferably using the application of negative pressure, can be targeted to minimize the risk of infection, while promoting tissue viability and the removal of deleterious substances from the wound site. The application of reduced or negative pressure to a wound site has been found to generally promote faster healing, increased blood flow, decreased bacterial burden, increased rate of granulation tissue formation, to stimulate the proliferation of fibroblasts, stimulate the proliferation of endothelial cells, close chronic open wounds, inhibit burn penetration, and/or enhance flap and graft attachment, among other things. It has also been reported that wounds that have exhibited positive response to treatment by the application of negative pressure include infected open wounds, decubitus ulcers, dehisced incisions, partial thickness burns, and various lesions to which flaps or grafts have been attached. Consequently, the application of negative pressure to a wound site 106 can be beneficial to a patient.

Accordingly, certain embodiments provide for a wound contact layer 105 to be placed over the wound site 106. The wound contact layer can also be referred to as an organ protection layer and/or a tissue protection layer. Preferably, the wound contact layer 105 can be a thin, flexible material which will not adhere to the wound site or the exposed viscera in close proximity. For example, polymers such as polyurethane, polyethylene, polytetrafluoroethylene, or blends thereof may be used. In one embodiment, the wound contact layer is permeable. For example, the wound contact layer 105 can be provided with openings, such as holes, slits, or channels, to allow the removal of fluids from the wound site 106 or the transmittal of negative pressure to the wound site 106. Additional embodiments of the wound contact layer 105 are described in further detail below.

Certain embodiments of the negative pressure treatment system 101 may also use a porous wound filler 103, which can be disposed over the wound contact layer 105. This pad 103 can be constructed from a porous material, for example foam, that is soft, resiliently flexible, and generally conformable to the wound site 106. Such a foam can include an open-celled and reticulated foam made, for example, of a polymer. Suitable foams include foams composed of, for example, polyurethane, silicone, and polyvinyl alcohol. Preferably, this pad 103 can channel wound exudate and other fluids through itself when negative pressure is applied to the wound. Some pads 103 may include preformed channels or openings for such purposes. In certain embodiments, the pad 103 may have a thickness between about one inch and about two inches. The pad may also have a length of between about 16 and 17 inches, and a width of between about 11 and 12 inches. In other embodiments, the thickness, width, and/or length can have other suitable values. Other embodiments of wound fillers that may be used in place of or in addition to the pad 103 are discussed in further detail below.

Preferably, a drape 107 is used to seal the wound site 106. The drape 107 can be at least partially liquid impermeable, such that at least a partial negative pressure may be maintained at the wound site. Suitable materials for the drape 107 include, without limitation, synthetic polymeric materials that do not significantly absorb aqueous fluids, including polyolefins such as polyethylene and polypropylene, polyurethanes, polysiloxanes, polyamides, polyesters, and other copolymers and mixtures thereof. The materials used in the drape may be hydrophobic or hydrophilic. Examples of suitable materials include Transeal® available from DeRoyal and OpSite® available from Smith & Nephew. In order to aid patient comfort and avoid skin maceration, the drapes in certain embodiments are at least partly breathable, such that water vapor is able to pass through without remaining trapped under the dressing. An adhesive layer may be provided on at least a portion the underside of the drape 107 to secure the drape to the skin of the patient, although certain embodiments may instead use a separate adhesive or adhesive strip. Optionally, a release layer may be disposed over the adhesive layer to protect it prior to use and to facilitate handling the drape 107; in some embodiments, the release layer may be composed of multiple sections.

The negative pressure system 101 can be connected to a source of negative pressure, for example a pump 114. One example of a suitable pump is the Renasys EZ pump available from Smith & Nephew. The drape 107 may be connected to the source of negative pressure 114 via a conduit 112. The conduit 112 may be connected to a port 113 situated over an aperture 109 in the drape 107, or else the conduit 112 may be connected directly through the aperture 109 without the use of a port. In a further alternative, the conduit may pass underneath the drape and extend from a side of the drape. U.S. Pat. No. 7,524,315 discloses other similar aspects of negative pressure systems and is hereby incorporated by reference in its entirety and should be considered a part of this specification.

In many applications, a container or other storage unit 115 may be interposed between the source of negative pressure 114 and the conduit 112 so as to permit wound exudate and other fluids removed from the wound site to be stored without entering the source of negative pressure. Certain types of negative pressure sources—for example, peristaltic pumps—may also permit a container 115 to be placed after the pump 114. Some embodiments may also use a filter to prevent fluids, aerosols, and other microbial contaminants from leaving the container 115 and/or entering the source of negative pressure 114. Further embodiments may also include a shut-off valve or occluding hydrophobic and/or oleophobic filter in the container to prevent overflow; other embodiments may include sensing means, such as capacitive sensors or other fluid level detectors that act to stop or shut off the source of negative pressure should the level of fluid in the container be nearing capacity. At the pump exhaust, it may also be preferable to provide an odor filter, such as an activated charcoal canister.

Eulerian Video Magnification Wound Monitoring and NPWT Treatment

Novel techniques for the analysis of small changes in pixels over time have been developed using a technique called "Eulerian Video Magnification" (EVM). EVM can act to amplify these extremely small changes in pixels over time, therefore allowing detection of previously undetectable changes. For example, EVM may be applied to standard video such as those taken by an optical camera. Minute visual changes in the state of the object and/or person being videoed can then be amplified by EVM and therefore be detected. For example, EVM can detect blood flow under the skin or breathing, such as in neonatal infants. Additional details regarding EVM are provided in an article published by the Massachusetts Institute of Technology titled "Eulerian Video Magnification for Revealing Subtle Changes in the World" by Wu et al, hereby incorporated by reference in its entirety.

EVM serves to amplify subtle changes in any spatial location in a video (such as a pixel) over time. Such subtle changes may not be visible to the naked eye, therefore EVM allows for the detection of minute phenomena undetectable under normal viewing and monitoring. Such video can be collected via any suitable means and is not simply limited to video collected within the visible light spectra. For example, video may be collected via: camera, charge-coupled devices (CCDs), oxygen saturation (spO2) detector, magnetic resonance imaging, x-ray imaging, infrared imaging or any form of video data collection over time. The amplified change in a pixel value can be the result of changes due to variations in color, motion, or any other suitable change depending upon the type of video. For example, video of spO2 measurements in a particular area could output as a value, such as a color, therefore EVM applied to such a video could detect subtle changes in spO2. As described above, additional details regarding EVM are provided in an article published by the Massachusetts Institute of Technology titled "Eulerian Video Magnification for Revealing Subtle Changes in the World" by Wu et al.

As described by Wu et al, spatial and temporal processing can be used to emphasize subtle temporal changes in a video. An embodiment of this process is illustrated in FIG. 3. In brief, the EVM system 300 first decomposes 304 the input video sequence 302 into different spatial frequency bands 306, and applies the same temporal filter to all bands 308. The filtered spatial bands 310 are then amplified by a given factor α 312, added back to the original signal 314, and collapsed to generate the output video 316.

As described by Wu, first, the video sequence is decomposed into different spatial frequency bands. These bands might be magnified differently because (a) they might exhibit different signal-to-noise ratios or (b) they might contain spatial frequencies for which the linear approximation described later for motion magnification does not hold. In the latter case, amplification for these bands may be reduced to suppress artifacts. When the goal of spatial processing is simply to increase the temporal signal-to-noise ratio by pooling multiple pixels, the frames of the video may be subjected to a spatially low-pass filter and down sampled for computational efficiency. In the general case, however, a full Laplacian pyramid [Burt and Adelson 1983] may be performed, followed by temporal processing on each spatial band. The time series corresponding to the value of a pixel in a frequency band may be considered and a bandpass filter may be applied to extract the frequency bands of interest. For example, we might select frequencies within 0.4-4 Hz, corresponding to 24-240 beats per minute, if we wish to magnify a pulse. If we are able to extract the pulse rate, we can use a narrow band around that value. The temporal processing is uniform for all spatial levels, and for all pixels within each level. We then multiply the extracted bandpassed signal by a magnification factor. This factor can be specified by the user, and may be attenuated automatically according to guidelines described below. Possible temporal filters are also discussed below. Next, we add the magnified signal to the original and collapse the spatial pyramid to obtain the final output. Since natural videos are spatially and temporally smooth, and since our filtering is performed uniformly over the pixels, our method implicitly maintains spatiotemporal coherency of the results.

To explain the relationship between temporal processing and motion magnification, we consider the simple case of a 1D signal undergoing translational motion. This analysis generalizes directly to locally-translational motion in 2D. Let I(x; t) denote the image intensity at position x and time t. Since the image undergoes translational motion, we can express the observed intensities with respect to a displacement function δ(t), such that I(x; t)=f(x+δ(t)) and I(x; 0)=f(x). The goal of motion magnification is to synthesize the signal Î(x,t)=f(x+(1+α)δ(t)) for some amplification factor α.

Assuming the image can be approximated by a first-order Taylor series expansion, we write the image at time t, f(x+δ(t)) in a first-order Taylor expansion about x, as $$I(x, t) \approx f(x) + \delta(t)\frac{\partial f(x)}{\partial x}.$$

Let B(x; t) be the result of applying a broadband temporal bandpass filter to I(x; t) at every position x (picking out everything except f(x) in the above equation). For now, let us assume the motion signal, (t), is within the passband of the temporal bandpass filter (we will relax that assumption later). Then we have $$B(x, t) = \delta(t)\frac{\partial f(x)}{\partial x}.$$

In our process, we then amplify that bandpass signal by and add it back to I(x; t), resulting in the processed signal $$\tilde{I}(x,t)=I(x,t)+\alpha B(x,t).$$

Combining the previous equations, we now have $$\tilde{I}(x, t) \approx f(x) + (1 + \alpha)\delta(t)\frac{\partial f(x)}{\partial x}.$$

Assuming the first-order Taylor expansion holds for the amplified larger perturbation, $(1+\alpha)\delta(t)$, we can relate the amplification of the temporally bandpassed signal to motion magnification. The processed output is simply $$\tilde{I}(x,t) \approx f(x+(1+\alpha)\delta(t)).$$

This shows that the processing magnifies motions—the spatial displacement $\delta(t)$ of the local image f(x) at time t, has been amplified to a magnitude of $(1+\alpha)$. For a low frequency cosine wave and a relatively small displacement, (t), the first-order Taylor series expansion serves as a good approximation for the translated signal at time t+1. When boosting the temporal signal by and adding it back to I(x; t), we approximate that wave translated by $(1+\alpha)\delta$. For quickly changing image functions (i.e., high spatial frequencies), f(x), the first-order Taylor series approximations becomes inaccurate for large values of the perturbation, $1+\alpha\delta(t)$, which increases both with larger magnification and motion $\delta(t)$.

As a function of spatial frequency, $\omega$, we can derive a guide for how large the motion amplification factor, $\alpha$, can be, given the observed motion $\delta(t)$. For the processed signal, I (x, t) to be approximately equal to the true magnification motion, I(x,t), we seek the conditions under which:

$$\tilde{I}(x, t) \approx \hat{I}(x, t)$$
$$\Rightarrow f(x) + (1 + \alpha)\delta(t)\frac{\partial f(x)}{\partial x} \approx f(x + (1 + \alpha)\delta(t))$$

Further rearrangement via the addition law of cosines and use of the following approximation:

$$\cos(\beta\omega\delta(t))\approx 1$$

$$\sin(\beta\omega\delta(t))\approx\beta\delta(t)\omega$$

leads to the following guideline:

$$(1 + \alpha)\delta(t) < \frac{\lambda}{8}.$$

This guideline provides the largest motion amplification factor, $\alpha$, compatible with accurate motion magnification of a given video motion $\delta(t)$ and image structure spatial wavelength, $\lambda$. In some videos, violating the approximation limit can be perceptually preferred and we leave the $\lambda$ cutoff as a user-modifiable parameter in the multiscale processing.

In some embodiments, to process an input video by Eulerian video magnification, there are four steps a user needs to take: (1) select a temporal bandpass filter; (2) select an amplification factor, $\alpha$; (3) select a spatial frequency cutoff (specified by spatial wavelength, $\lambda c$) beyond which an attenuated version of $\alpha$ is used; and (4) select the form of the attenuation for $\alpha$, either force $\alpha$ to zero for all $\lambda<\lambda c$, or linearly scale $\alpha$ down to zero. The frequency band of interest can be chosen automatically in some cases, but it is often important for users to be able to control the frequency band corresponding to their application. In our real-time application, the amplification factor and cut-off frequencies are all customizable by the user.

One of skill in the art will understand that use of the term "color" as used herein this section and throughout the specification, may not only represent the optical spectrum. The word "color" may at times be used colloquially to identify a spectral frequency range (which may or may not be in the visible range). One of skill in the art will further understand that in embodiments, the techniques described herein may also function without the use of EVM, for example by detecting a change in green/red. However, such systems without EVM may have a significant reduction in sensitivity.

Of particular interest for the evaluation of wounds, in some embodiments, Eulerian Video Magnification may be used to amplify subtle changes in pixel values relating to color using video collected from a CCD camera or RGB color detector. In embodiments, a camera or RGB color detector may be combined with one or more standard LEDs to light the wound for visualization. For example, within a patch of skin or a wound bed, color changes may be indicative of favorable blood flow. For example, a value in the red spectrum via color detection may indicate blood flow, therefore, if the difference between the peak value and trough value of the color is small then it suggests that there is not much blood flow. Conversely, if the difference between the peak value and the trough value is relatively high, then this may indicate good blood flow to the tissue area.

Further, if the value is less red then there is likely to be insufficient oxygen. In embodiments, color could also be used to generate an indication of blood oxygen (or with the light source modified to sense SP02 directly), to minimize the likelihood of damage to the capillaries and to act as an alert if exsanguination does occur, potentially mitigating against potential harm that may be caused by NPWT. In some embodiments, EVM may be used on skin near a wound to monitor the motion of the adjacent skin due therefore identify whether the blood pulse is making it to the area of concern. Advantageously, absolute values need not be monitored to identify potential issues within the wound or tissue, instead monitoring of the difference in values is sufficient.

Figure 9:
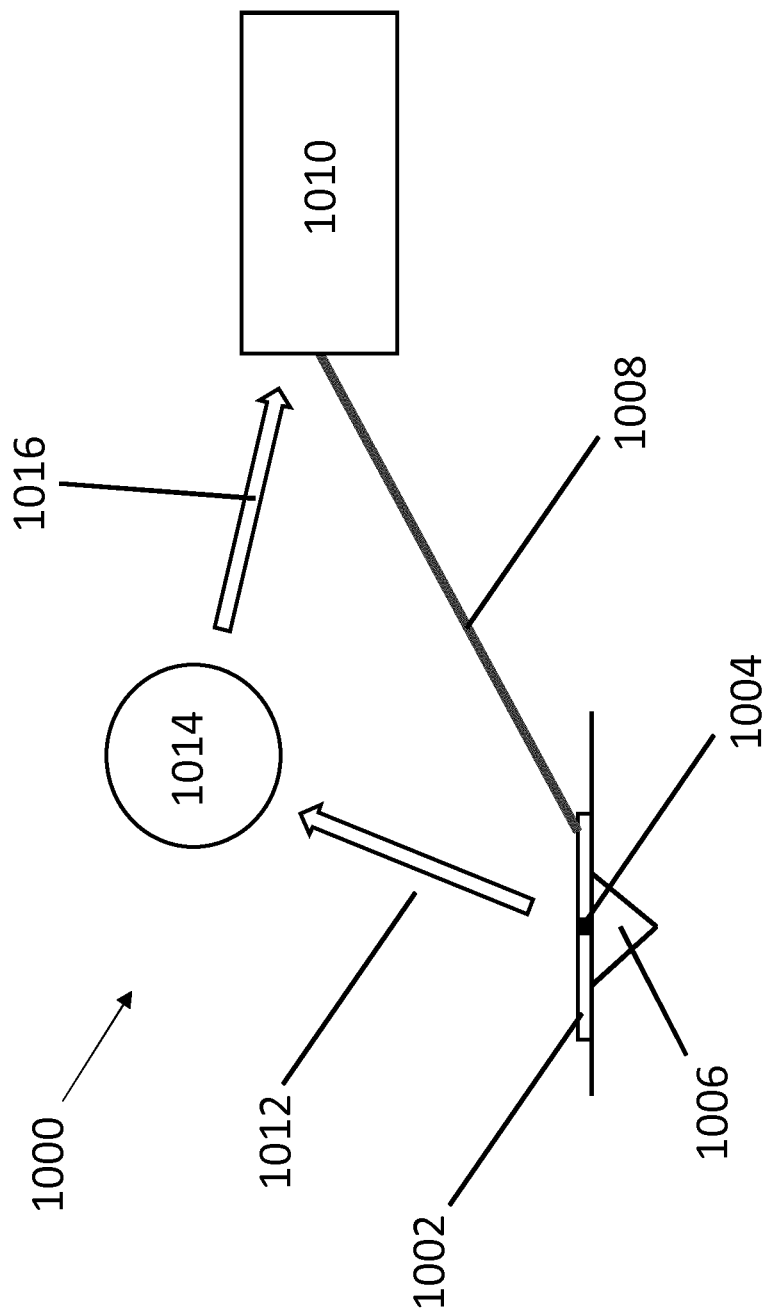
FIG. 9 illustrates an embodiment of a wound treatment system.

FIG. 9 depicts an embodiment of a NPWT system 1000 incorporating EVM. A dressing 1002, similar to the dressings disclosed previously with respect FIGS. 1 and 5A-7, may contain at least one sensor 1004. In embodiments, the dressing may contain one sensor, two sensors, three sensors, four sensors, five sensors, at least about 10 sensors, at least about 20 sensors, or more than 20 sensors. The sensors may be placed in any layer of the dressing, for example, the wound contact layer, the absorbent layer, the transmission layer, or the cover layer. The sensors may be distributed between multiple layers, such as in the wound contact layer and the absorbent layer, the wound contact layer and the cover layer, etc. The sensors may be in the form of an array. In embodiments, the sensor(s) may be separated by an air gap or coated with a barrier layer that is transparent in the wavelengths to be used. Additional layers, such as polyurethane foam, may be used behind the sensor(s) to provide cushioning to minimise the pressure focus generated by the sensor if a patient rests upon the sensor. The sensor(s) may further be encapsulated in silicone or polyurethane.

In embodiments, the sensor(s) may collect information such as: pH, temperature, light, conductivity, impedance, capacitance, or other characteristics of the wound. In some embodiments, the sensors can provide information about the blood flow, moistness or dryness of the wound, lactate levels, or other characteristics of the wound. In some embodiments, all manner of sensor(s) may be incorporated in the system and they may be configured to measure parameters such as temperature, pH, oxygen, carbon dioxide, conductivity, inductance, lactate, metallomatrix proteases, growth factors, optical absorption and reflectance including at infrared and UV frequencies and fluorescence, infection (level of bacterial burden and types of bacteria), or other characteristics of the wound environment. In certain embodiments, ultrasonic sensors with or without transducers may be used.

In some embodiments, thermistors or thermocouples may be used in place of the RGB sensor/CCD and light source described above. A grid or matrix of such sensors could be mounted and close-coupled to the tissue. These could be used in concert with other sensors (e.g. optical or EEG/ECG) to allow separation of the heart rate from the temperature noise of the environment (i.e. identifying the temperature changes that occur at the frequency of the heart pulse).

In embodiments, sensing coils may be placed within the dressing in place of or in addition to the CCD/RGB sensor. Coils may be mounted co-axially either nested or offset within the dressing. In some embodiments, a separate probe may be used to contain the coils, such a probe may be held against the tissue and transmit signals by wired or wireless connection.

As described above, optical sensors may be used to measure wound appearance using an RGB sensor with an illumination source. Both the RGB sensor and the illumination source may be pressed up against the skin, such that light would penetrate into the tissue and take on the spectral features of the tissue itself. Light propagation in tissue is dominated by two major phenomena, scattering and attenuation. For attenuation, as light passes through tissue, the intensity is lost due to absorption by various components of the tissue. Blue light tends to be attenuated heavily, whilst light at the red end of the spectrum tends to be attenuated least.

Scattering processes are more complex, and have various regimes which must be considered. The first aspect of scattering is based on the size of the scattering centre compared with the wavelength of incident light. If the scattering center is much smaller than the wavelength of light, then Rayleigh scattering can be assumed. If the scattering center is on the order of the wavelength of light, then a more detailed Mie scattering formulation must be considered. Another factor involved in scattering light is the distance between input and output of the scattering media. If the mean free path of the light (the distance between scattering events) is much larger than the distance travelled, then ballistic photon transport is assumed. In the case of tissue, scatting events are approximately 100 microns apart—so a 1 mm path distance would effectively randomise the photon direction and the system would enter a diffusive regime.

Ultra-bright light emitting diodes (LEDs), an RGB sensor, and polyester optical filters can be used as components of the optical sensors to measure tissue color differentiation. For example, because surface color can be measured from reflected light, a color can be measured from light which has passed through the tissue first for a given geometry. This can include color sensing from diffuse scattered light, from an LED in contact with the skin. In some embodiments, an LED can be used with an RGB sensor nearby to detect the light which has diffused through the tissue. The optical sensors can image with diffuse internal light or surface reflected light. Optical sensors can also be used to measure autoflorescence. Autoflourescense is used because the tissue is absorbing light at one wavelength, and emitting at another. Additionally, dead tissue may not auto-fluoresce and so this could be a very strong indication as to if the tissue is healthy or not. Due to blue light (or even UV light) having such a short penetration depth, it may be very useful for example to have a UV light with a red sensitive photodiode nearby (or some other wavelength shifted band) to act as a binary test for healthy tissue, which would auto-fluoresce at a very particular wavelength.

Returning to the embodiment of FIG. 9, dressing 1002 with sensor 1004 may be positioned over wound 1006. Similar to the systems depicted previously in FIGS. 1, 5A-B, and 7, the dressing may be connected to a source of negative pressure, the source of negative pressure configured to deliver negative pressure to the wound 1006. The sensor 1004 may be in communication 1012 with controller 1014, via any suitable wired or wireless means. In certain embodiments, the communication from the sensor to the controller may be one-way, with the controller only receiving information from the sensor. However, alternatively, the communication 1012 between the sensor and the controller may be two-way with the sensor sending information to the controller but also receiving instructions and/or information from the controller. Controller 1014 may then be in communication, via wired or wireless means, with negative pressure source 1010.

The controller may be any processing device capable of executing software. For example, the processing device may be a processor, PC, tablet, smartphone, or other computer capable of running host software. In embodiments, the controller may be attached to the dressing and/or the pump or it may be separate. When the system 1000 is operating, the sensor 1004 collects video data from the wound 1006 over time. This video data may be collected and stored to be transmitted to the controller 1014 at periodic intervals and/or the video data may be continuously transmitted to the controller. The wound video data collected by the sensor 1004 may be of any data potentially collected from any sensor disclosed herein this section or elsewhere in the specification, but suitably visible optical data or IR data. In embodiments, the sensor 1004 may detect the edge of the wound 1006 and then collect video of the edge of the wound, for example collecting optical data including motion and color information. Such information may then be transmitted to the controller 1014, whereby the controller applies EVM to the video. As described previously, EVM, can be used to detect very subtle changes in individual locations/pixels within a video. In certain embodiments, EVM may be applied to a single pixel. Such a single pixel may be from a single sensor or combined/averaged from multiple sensors. In some embodiments, multiple pixels may be drawn from a single sensor or form multiple sensors such as in an array. For motion detection (i.e. identification of tissue movement due to blood pulsing within it as described elsewhere), multiple, closely aligned pixels may be required. However, in embodiments, single pixels or multiple pixels from a single sensor may be used.

Changes in color and/or motion may be indicative of blood flow to the tissue surrounding the wound or to the wound itself. As will be described in greater detail below, change in color, motion, or another parameter may indicate that vacuum at the wound site should be increased, decreased, or remain the same. If an increase or decrease is merited, the controller may communicate 1016 with the source of negative pressure 1010 and direct the source of negative pressure 1010 to increase vacuum or decrease vacuum. Such communication may be in the form of a feed-back loop, allowing for the source of negative pressure to continue to increase or decrease the vacuum at the wound site until a desired level is reached, for example a desired treatment parameter. In embodiments, the source of negative pressure can be configured to deliver continuous negative pressure or intermittent negative pressure, depending on the desired wound treatment.

In some embodiments, time series analysis algorithms such Auto Regressive Integrated Moving Average (ARIMA), Generalized Autoregressive Conditional Heteroskedasticity (GARCH), or Cusum (or cumulative sum) can be used to determine changes in values between pixels locations in video frames over time, such as described herein this section or elsewhere in the specification. For example, indicative of blood flow or motion. Cusum can be defined as the running sum of the difference between each sample and the mean (e.g., in the absence of change, Cusum is zero). Cusum can be used to track variations in the underlying variable, including one or more of redness, delta-red, motion, or a calculated treatment parameter. Determined Cusum value or values can be compared to one or more thresholds to determine blood flow and/or motion and/or any suitable value disclosed herein this section or elsewhere in the specification.

In certain embodiments, a proportional integral derivative algorithm (PID) style loop may be used by the NPWT pump, to ensure that the integrated blood flow is suitable to maintain the tissue in an acceptable condition and optimal pressure may be used to ensure optimal blood flow without producing excessive blood flow. PID style loops are well-known in the art for adjusting the output of a pump as a process variable changes.

Advantageously, the use of EVM allows the source of negative pressure to be responsive to changes in the wound and surrounding tissue, rather than simply being responsive to detected levels of negative pressure in the wound bed as is known in the art. Further, NPWT utilizing EVM could be tailored to the desired result (the increased blood flow) rather than a nominal vacuum, potentially minimizing power consumption, pain and vacuum damage while generating the correct effect. Such a reactive system may also be pro-active in avoiding ischemia, as low blood flow could be detected early and treated before traditional detection. In embodiments, the vacuum may be increased to provide increased blood flow, then held at such a level as increased vacuum begins to restrict flow. Further, the system 1000 may allow for treatment of oedema by triggering an increase in NPWT upon the identification of areas of oedema, thereby minimizing oedema by increasing effective compression. In certain embodiments, a maximum value of color change may not be desirable because a high value may indicate that a large blood vessel is close to the surface and strained.

Figure 8:
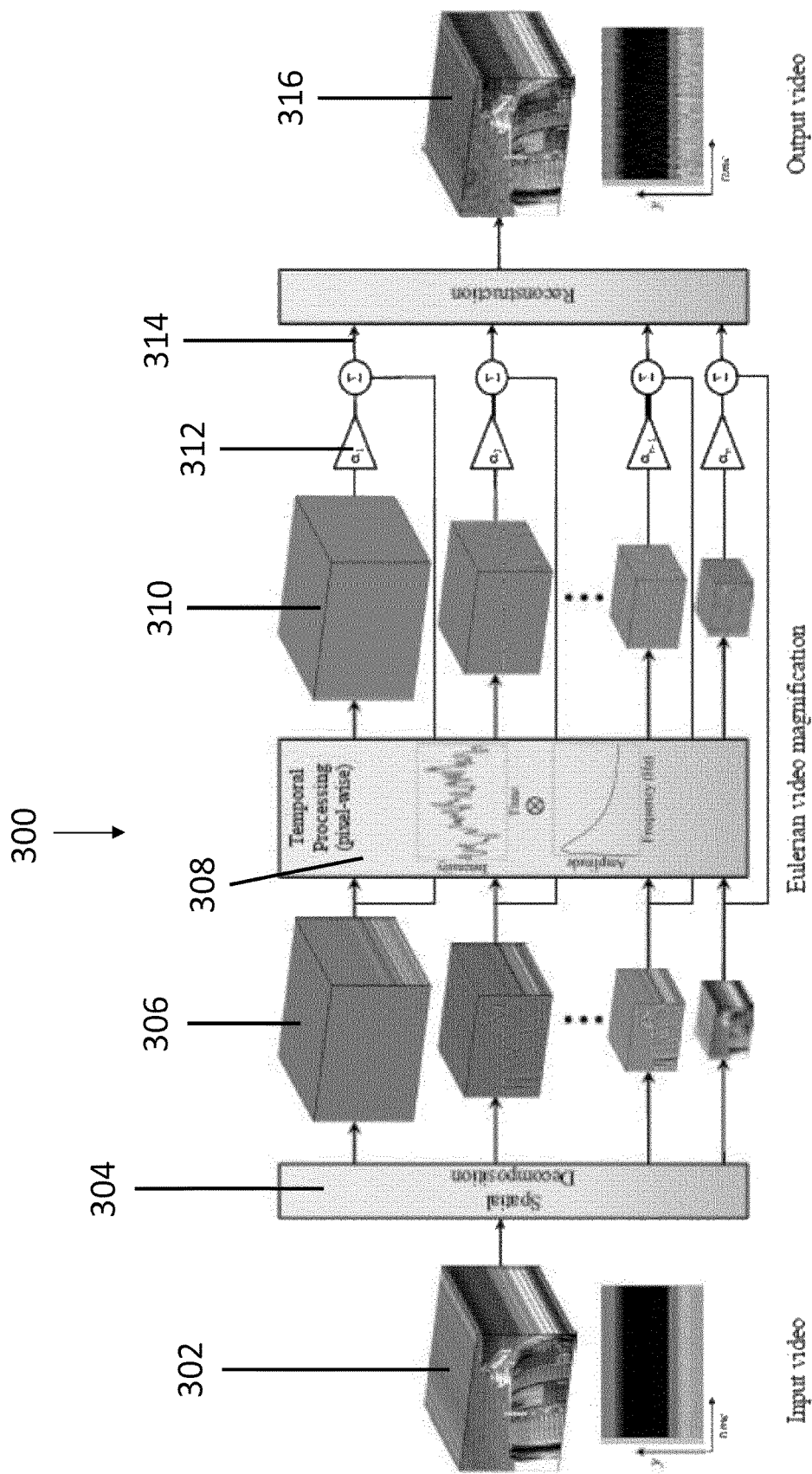
FIG. 8 illustrates an embodiment of a process for video amplification known as Eulerian video magnification.
Figure 10A:
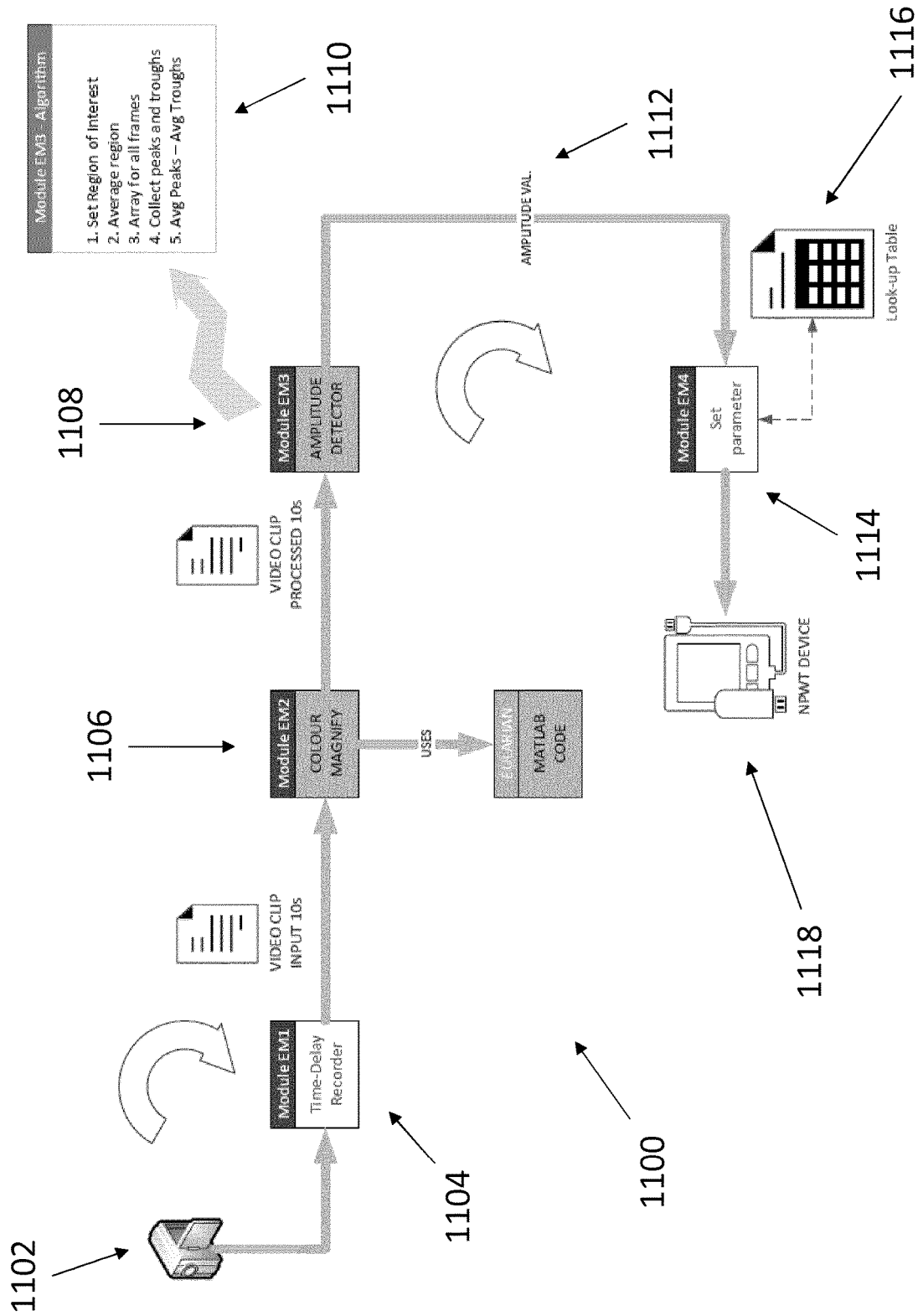
FIG. 10A illustrates an embodiment of a process for providing NPWT treatment.

FIG. 10A depicts an embodiment of a method of EVM processing in combination with NPWT 1100, providing greater detail on the steps taken from collection of video data to alteration in NPWT shown above in FIG. 9. Although FIG. 10A makes reference to "modules," one of skill in the art will understand that such modules may be software steps that may be completed on one or more computing devices, such as the controller described above in relation to FIG. 8.

Such computing devices may be any computing device disclosed herein this section or elsewhere in the specification, for example a controller, smartphone, server, or general computer such as a laptop or desktop. In the first step, a video capture device 1102, such as a camera or other sensor device, such as disclosed herein this section or elsewhere in the specification, collects video of a wound to be treated with NPWT. In the scenario of NPWT applied through a wound dressing, video may be taken from a sensor within the dressing, under the dressing, over the dressing, or any suitable location.

Next, a video clip of a desired length 1104, for example 10 seconds, is collected and stored 1104. It will be understood by one of skill in the art that the video clip may be of any suitable length, for example, about: 1 second, 5 seconds, 10 seconds, 15 seconds, 30 seconds, 60 seconds, 5 minutes, 1 hours, 12 hours, 24 hours, or more than 24 hours. Further, in certain embodiments, the video is continuously transmitted and continuously processed for analysis. The embodiment disclosed in FIG. 9 may be performed with clips of video or with continuously transmitted video. In some embodiments, the video may contain at least about: 5 frames per second, 10 frames per second, 20 frames per second, 30 frames per second, 45 frames per second, 60 frames per second, 75 frames per second, 90 frames per second, 120 frames per second, or more than 120 frames per second.

Once the video has been captured, the values of each location/pixel within the video are magnified via EVM 1106. Such an EVM algorithm may be executed within any suitable software medium, for example MATLAB code. In embodiments involving a video taken with a standard camera in the visible light spectrum, the EVM algorithm may serve to amplify the color values of the image. For example, the EVM algorithm may amplify the red color values within the video. As described above, redness may be an indicator of blood perfusion to a particular tissue. Once the video clip or continuously streamed video has been processed, a "treatment parameter" is determined. For example, if a change in redness is of interest, the change in redness or delta-red may be determined for every location and/or pixel of interest and used in the calculation of the treatment parameter. In some embodiments, the treatment parameter may be calculated by the following steps 1110. First, a region or regions of interest are set within a video frame, by selecting one or more pixels within a particular area of the video frame. In certain embodiments, this can be set by a user via selection of all pixels with a specific range of baseline colors and/or around a particular location on the tissue. In embodiments, the region may make use of all sensors and/or pixels that are collected Next, the pixels within the region are averaged to provide an average value per region per frame. The averaging process may incorporate sophistication to eliminate outliers that may be introduced in to the system. Then, an array is generated for the average values over time as additional data is collected with each consecutive frame of the video. From these consecutive frames, the highest values and lowest values may be collected, for example the highest and lowest red values. Then, the average peak value may be calculated for the highest values and the average trough value may be calculated from the lowest values. Subtracting this highest average peak value from the lowest average trough value then gives a single value. This value can then be calibrated 1112 to equate to a single parameter number, referred to as the "treatment parameter." As will be described below, the "treatment parameter" can be compared to a value in a lookup table 1116 to indicate whether a NPWT device should increase or decrease application of negative pressure. If the treatment parameter is determined from changes in red color within a video, then higher treatment parameters would tend to indicate good blood perfusion, while lower treatment parameters would tend to indicate poor blood flow.

Figure 10B:
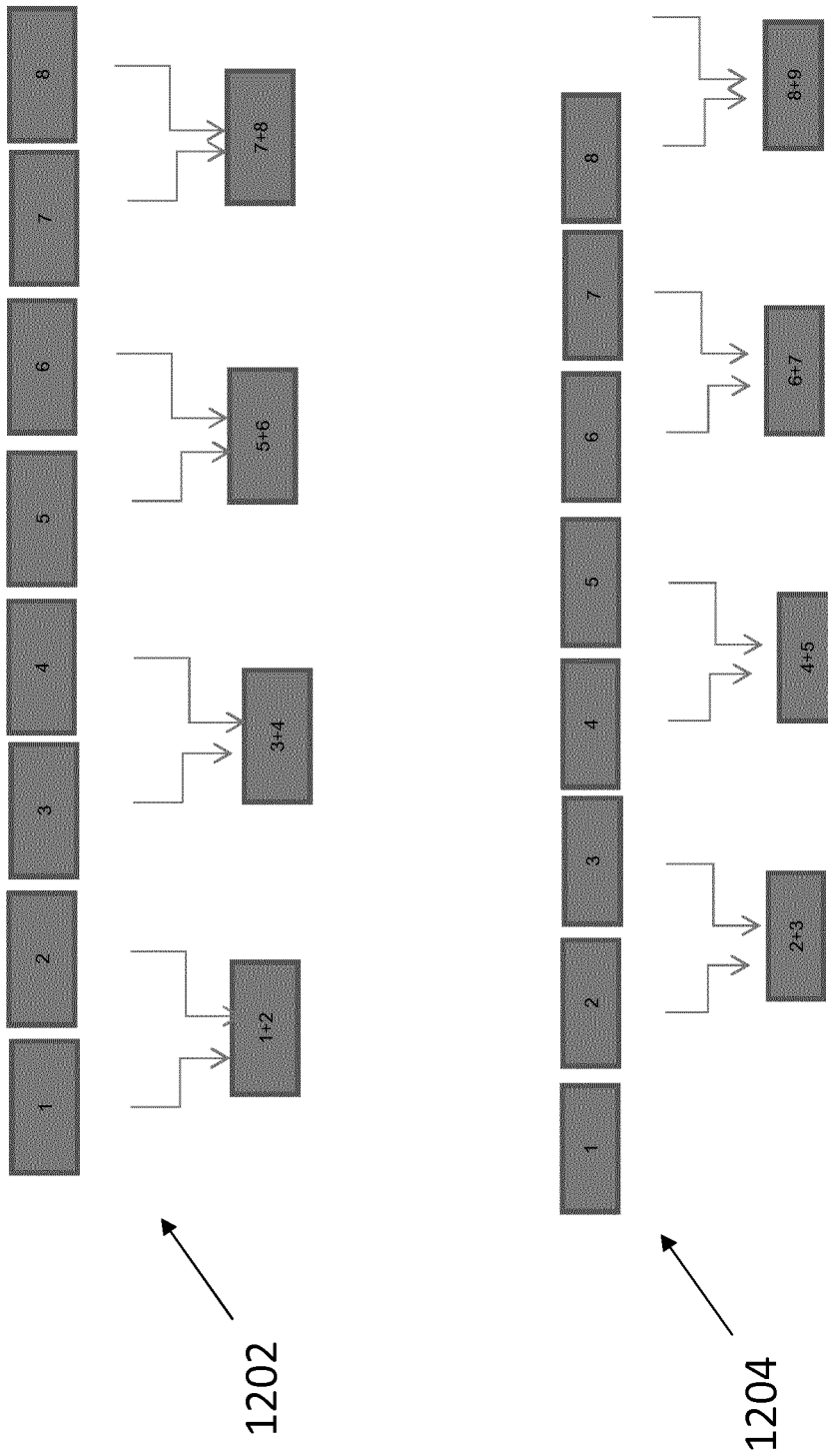
FIG. 10B illustrates an embodiment of a sampling method for sampling frames from a video.

As depicted in FIG. 10B, which can be implemented by a controller, in certain embodiments, to reduce the use of a high-rate sampling, multiple frames could be combined to provide a signal at a lower frame rate. For example, the values from frame 1 and frame 2 may be combined, along with the values from frame 3 and frame 4, and so on 1202. Then the combination of 1+2 may be compared with the value of 3+4 to identify both the highest and lowest signals for us in calculation of the treatment parameter. In some embodiments, the combined values could be calculated in a different manner 1204, for example, by combining frames 2 and 3, to be compared to a combination of frames 4 and 5, etc. Once the values within each frame are combined, then the amplitude of the change in values may be calculated, in a similar fashion as described above by subtraction the average trough value from the average peak value. The treatment parameter may be calculated from changes in red value in a video that has undergone EVM. However, in further embodiments, any particular color value may be used such as blue or green. Further, any particular value may be used that can be derived from video generated by any of the sensors disclosed herein this section or elsewhere in the specification, such as spO2 or infrared.

Returning to FIG. 10A, once the treatment parameter has been calculated, the controller may compare the treatment parameter 1114 to a pre-set desired value or range. Such a desired value or range may be pre-set by the controller or by a clinician. Such a desired value or range may be determined from literature, via experimentation, via algorithm, or via other suitable means. Regardless, the use of a desired value or range allows the controller to compare the calculated treatment parameter to the desired value or range in order to direct the NPWT device to apply more or less negative pressure. In embodiments, if the treatment parameter is below a desired value or range, then the controller may send a signal to the NPWT device to increase the amount of negative pressure at the wound. Conversely, if the treatment parameter is higher than a desired value or range, than the controller may send a signal to the NPWT device to decrease the amount of negative pressure at the wound. If the calculated treatment parameter is already at a desired value or within a desired range, then the controller may send no signal to the NPWT device or a signal to remain steady. In certain embodiments, if the treatment parameter remains at an undesired value or range for a period of time, then an alert may be generated.

In certain embodiments, the response to the treatment parameter measurements may be self-optimizing such the software may explore optimum responses, per a change in treatment parameter by examining the treatment/response curve. For example, if a particular change in NPWT results in a dramatic shift in treatment parameter, the system may adjust to only change NPWT for a desired amount. For example, NPWT may be adjusted until a maximum difference in the EVM output is achieved. In certain embodiments, it may be advantageous to build in a delay between therapy adjustments to allow time for the body to respond to the previous change in therapy.

In some embodiments, if a treatment parameter is above or at a desired value, then the controller may reduce the vacuum set point to −45 mmHg nominal (with +/−5 mmHg) unless the treatment parameter also reduces to an undesired level at which point the vacuum may be increased. At "low" difference (i.e. poor blood flow), the vacuum may be increased increase until the treatment parameter reaches a desired value or −125 mmHg whichever comes first. If the treatment parameter is too high then vacuum may be lowered to, for example, (or −45 mmHg min), however, if the treatment parameter is too low (i.e. poor blood flow) then vacuum could be moved to a higher level, increasing up to a −150 mmHg limit. In certainly embodiments, the vacuum limit may be adjusted for particular phsyiologies. In embodiments, the lower limit for vacuum may be set around about: −600 mmHg, −500 mmHg, −400 mmHg, −300 mmHg, −250 mmHg, 200 mmHg, 175 mm Hg, or about −235 mmHg.

In certain embodiments, potentially tailored for specific pumps, once the treatment parameter 1114 is calculated, the parameter may be compared to values within a 'lookup table' 1116 stored within the one or more computing devices (controller). FIG. 11A is a table of lookup values for use with the Pico pump system, described earlier in the specification in relation to FIGS. 5A-6B. The first column represents various settings associated with set points for the target negative pressure or vacuum. In certain embodiments, if the calculated treatment parameter is below a threshold or desired value or range, then the setting within the lookup table may be increased by +1, therefore causing the controller to increase the vacuum to the vacuum ranges dictated by the next setting. Conversely, if the treatment parameter is below a desired value or range, then the setting may be decreased by 1, thereby causing the controller to direct the NPWT device to decrease the setting to the next lower parameter setting. This process may be continued in cycles indefinitely until reaching setting 1 or setting 7. In embodiments, this process may also occur if increasing the vacuum decreases the treatment parameter.

In embodiments, if the device is already on parameter set 7 and treatment parameter is still below range then the NPWT device will remain on setting 7. Conversely, if the NPWT device is already on parameter set 1 and treatment parameter is above a desired range or parameter, then the NPWT device will remain at setting 1. In certain embodiments, if the treatment parameter reduces when the lookup table setting is increased, then the setting may revert back to the previous setting. FIG. 11B provides an embodiment of a lookup table for the RENASYS™ pump described above. The process for adjusting the vacuum based on the treatment parameter and comparing versus the lookup table may be substantially the same as that of FIG. 11A.

In some embodiments, the lookup table setting may instead be an equation, whereby the setting value may no longer only be confined to integral values, but may instead be the X-value and the Nominal set point [and pressure set points] on the Y-axis). The Parameter (X) value would then be set by a PI, PD or PID loop to match the optimal red-delta value. The acceptable red-delta value could be modified slightly (by the clinician) to allow for pain-susceptible patients where beneficial but sub-optimal therapy is preferable to pain. A continuous high-red value (with minimal red-delta) would also be an indicator of bleeding, one of the highest risks of NPWT. Such a control system, may also be suitable for pain management and bleeding-identification systems integrated into software packages, such as software systems associated with Renasys, described above. For example, while a specific location of bleeding may be detected as pulsatile, once blood flows away from the breach it will no longer have a pulse so the color maybe identified as red and not vary at the pulse rate Thus, such an indicator can be identified as bleeding and flagged as a cause for immediate intervention, therefore trigger the shut-down of NPWT to minimize exsanguination before the intervention is achieved.

In some embodiments, the computing systems described herein may include one or more computing devices, for example, a server, a laptop computer, a mobile device (for example, smart phone, smart watch, tablet, personal digital assistant), a kiosk, automobile console, or a media player, for example. In embodiments, the computing devices may include one or more central processing units (CPUs), which may each include a conventional or proprietary microprocessor. Computing devices may further includes one or more memory, such as random access memory (RAM) for temporary storage of information, one or more read only memory (ROM) for permanent storage of information, and one or more mass storage devices, such as a hard drive, diskette, solid state drive, or optical media storage device. In certain embodiments, the processing device, cloud server, server or gateway device, may be implemented as a computing system. In one embodiment, the modules of the computing systems are connected to the computer using a standard based bus system. In different embodiments, the standard based bus system could be implemented in Peripheral Component Interconnect (PCI), Microchannel, Small Computer computing system Interface (SCSI), Industrial Standard Architecture (ISA) and Extended ISA (EISA) architectures, for example. In addition, the functionality provided for in the components and modules of the computing devices disclosed herein may be combined into fewer components and modules or further separated into additional components and modules.

The computing devices disclosed herein may be controlled and coordinated by operating system software, for example, iOS, Windows XP, Windows Vista, Windows 7, Windows 8, Windows 10, Windows Server, Embedded Windows, Unix, Linux, Ubuntu Linux, SunOS, Solaris, Blackberry OS, Android, or other operating systems. In Macintosh systems, the operating system may be any available operating system, such as MAC OS X. In other embodiments, the computing device 13000 may be controlled by a proprietary operating system. Conventional operating systems control and schedule computer processes for execution, perform memory management, provide file system, networking, I/O services, and provide a user interface, such as a graphical user interface (GUI), among other things.

The computing devices disclosed herein may include one or more I/O interfaces and devices, for example, a touchpad or touchscreen, but could also include a keyboard, mouse, and printer. In one embodiment, the I/O interfaces and devices 13110 include one or more display devices (such as a touchscreen or monitor) that allow visual presentation of data to a user. More particularly, a display device may provide for the presentation of GUIs, application software data, and multimedia presentations, for example. The computing systems disclosed herein may also include one or more multimedia devices, such as cameras, speakers, video cards, graphics accelerators, and microphones, for example.

In general, the word "module," as used herein, refers to logic embodied in hardware or firmware, or to a collection of software instructions, possibly having entry and exit points, written in a programming language, such as, for example, Python, Java, Lua, C and/or C++. A software module may be compiled and linked into an executable program, installed in a dynamic link library, or may be written in an interpreted programming language such as, for example, BASIC, Perl, or Python. It will be appreciated that software modules may be callable from other modules or from themselves, and/or may be invoked in response to detected events or interrupts. Software modules configured for execution on computing devices may be provided on a computer readable medium, such as a compact disc, digital video disc, flash drive, or any other tangible medium. Such software code may be stored, partially or fully, on a memory device of the executing computing device, for execution by the computing device. Software instructions may be embedded in firmware, such as an EPROM. It will be further appreciated that hardware modules may be comprised of connected logic units, such as gates and flip-flops, and/or may be comprised of programmable units, such as programmable gate arrays or processors. The block diagrams disclosed herein may be implemented as modules. The modules described herein may be implemented as software modules, but may be represented in hardware or firmware. Generally, the modules described herein refer to logical modules that may be combined with other modules or divided into sub-modules despite their physical organization or storage.

Each of the processes, methods, and algorithms described in the preceding sections may be embodied in, and fully or partially automated by, code modules executed by one or more computer systems or computer processors comprising computer hardware. The code modules may be stored on any type of non-transitory computer-readable medium or computer storage device, such as hard drives, solid state memory, optical disc, and/or the like. The systems and modules may also be transmitted as generated data signals (for example, as part of a carrier wave or other analog or digital propagated signal) on a variety of computer-readable transmission mediums, including wireless-based and wired/cable-based mediums, and may take a variety of forms (for example, as part of a single or multiplexed analog signal, or as multiple discrete digital packets or frames). The processes and algorithms may be implemented partially or wholly in application-specific circuitry. The results of the disclosed processes and process steps may be stored, persistently or otherwise, in any type of non-transitory computer storage such as, for example, volatile or non-volatile storage.

All of the features disclosed in this specification (including any accompanying exhibits, claims, abstract and drawings), and/or all of the steps of any method or process so disclosed, may be combined in any combination, except combinations where at least some of such features and/or steps are mutually exclusive. The disclosure is not restricted to the details of any foregoing embodiments. The disclosure extends to any novel one, or any novel combination, of the features disclosed in this specification (including any accompanying claims, abstract and drawings), or to any novel one, or any novel combination, of the steps of any method or process so disclosed.

Various modifications to the implementations described in this disclosure may be readily apparent to those skilled in the art, and the generic principles defined herein may be applied to other implementations without departing from the spirit or scope of this disclosure. Thus, the disclosure is not intended to be limited to the implementations shown herein, but is to be accorded the widest scope consistent with the principles and features disclosed herein. Certain embodiments of the disclosure are encompassed in the claim set listed below or presented in the future.

What is claimed is:

1. A wound therapy system, comprising:
 a source of negative pressure configured to be in fluidic communication with a wound dressing placed over a wound, the source of negative pressure configured to provide negative pressure under the wound dressing;

a visualization sensor positioned above the wound, the visualization sensor configured to collect video data of the wound, the video data comprising a red color value; and a controller in communication with both the source of negative pressure and the visualization sensor, the controller configured to:
 amplify the red color value by Eulerian video magnification;
 determine a blood flow treatment factor from the amplified red color value, the blood flow treatment factor determined from the differences between region values measured in the video data;
 cause the source of negative pressure to increase or decrease a level of provided negative pressure if the blood flow treatment factor differs from a threshold, the threshold corresponding to a desired level of blood flow in the wound;
 cause the source of negative pressure to stop providing negative pressure in response to a change in the blood flow treatment factor; and
 increase the level of provided negative pressure if the amplified red color value shows a decrease from a baseline red color value, the baseline red color value collected at an earlier time than the red color value.

2. The wound therapy system of claim 1, wherein the video data comprises RGB color data.

3. The wound therapy system of claim 1, wherein the visualization sensor is configured to communicate wirelessly with the controller.

4. The wound therapy system of claim 1, wherein the controller is configured to communicate wirelessly with the source of negative pressure.

5. The wound therapy system of claim 1, wherein the controller is configured to transmit a signal to the source of negative pressure to increase negative pressure if the treatment parameter is below the desired value.

6. The wound therapy system of claim 1, wherein the controller is configured to cause the source of negative pressure to decrease the level of provided negative pressure if the treatment parameter is above the threshold.

7. The wound therapy system of claim 1, wherein the controller is configured to compare the treatment parameter to a plurality of thresholds.

8. The wound therapy system of claim 7, wherein the controller is configured to perform the comparison using a lookup table.

9. The wound therapy system of claim 1, wherein the controller is configured to decrease the level of provided negative pressure if the amplified red color value shows an increase from a baseline red color value, the baseline red color value collected at an earlier time than the red color value.

* * * * *